US011045484B2

(12) United States Patent
Wurz et al.

(10) Patent No.: US 11,045,484 B2
(45) Date of Patent: Jun. 29, 2021

(54) KRAS G12C INHIBITORS AND METHODS OF USING THE SAME

(71) Applicant: Amgen Inc., Thousand Oaks, CA (US)

(72) Inventors: Ryan Paul Wurz, Mewbury Park, CA (US); Victor J. Cee, Thousand Oaks, CA (US); Albert Amegadzie, Moorpark, CA (US); Ning Chen, Thousand Oaks, CA (US); Brian Alan Lanman, Woodland Hills, CA (US); Michael D. Bartberger, Sherman Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 16/402,589

(22) Filed: May 3, 2019

(65) Prior Publication Data
US 2019/0336514 A1 Nov. 7, 2019

Related U.S. Application Data

(60) Provisional application No. 62/667,314, filed on May 4, 2018.

(51) Int. Cl.
| A61K 31/675 | (2006.01) |
| A61P 35/00 | (2006.01) |
| A61K 31/167 | (2006.01) |
| A61K 31/553 | (2006.01) |
| C07K 16/30 | (2006.01) |
| A61K 45/06 | (2006.01) |

(52) U.S. Cl.
CPC .......... *A61K 31/675* (2013.01); *A61K 31/167* (2013.01); *A61K 31/553* (2013.01); *A61P 35/00* (2018.01); *C07K 16/30* (2013.01); *A61K 45/06* (2013.01)

(58) Field of Classification Search
CPC ..... C07F 9/6561; C07K 16/30; A61K 31/167; A61K 31/553; A61K 31/675; A61K 45/06
See application file for complete search history.

(56) References Cited

U.S. PATENT DOCUMENTS

| 4,232,027 A | 11/1980 | Turk et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,151,413 A | 9/1992 | Caufield et al. |
| 5,256,790 A | 10/1993 | Nelson |
| 5,258,389 A | 11/1993 | Goulet et al. |
| 5,521,184 A | 5/1996 | Zimmermann |
| 5,650,415 A | 7/1997 | Tang et al. |
| 5,656,643 A | 8/1997 | Spada et al. |
| 5,712,291 A | 1/1998 | D'Amato |
| 5,728,813 A | 3/1998 | Lyman et al. |
| 5,747,498 A | 5/1998 | Schnur et al. |
| 5,770,599 A | 6/1998 | Gibson |
| 5,789,427 A | 8/1998 | Chen et al. |
| 5,792,783 A | 8/1998 | Tang et al. |
| 5,861,510 A | 1/1999 | Piscopio et al. |
| 5,863,949 A | 1/1999 | Robinson et al. |
| 5,892,112 A | 4/1999 | Levy et al. |
| 5,969,110 A | 10/1999 | Beckmann et al. |
| 5,981,245 A | 11/1999 | Fox et al. |
| 5,990,141 A | 11/1999 | Hirth et al. |
| 6,057,124 A | 5/2000 | Bartley et al. |
| 6,111,090 A | 8/2000 | Gorman et al. |
| 6,232,447 B1 | 5/2001 | Cerretti |
| 6,235,764 B1 | 5/2001 | Larson et al. |
| 6,258,812 B1 | 7/2001 | Bold et al. |
| 6,413,932 B1 | 7/2002 | Cerretti et al. |
| 6,515,004 B1 | 2/2003 | Misra et al. |
| 6,596,852 B2 | 7/2003 | Cerretti et al. |
| 6,630,500 B2 | 10/2003 | Gingrich et al. |
| 6,656,963 B2 | 12/2003 | Firestone et al. |
| 6,713,485 B2 | 3/2004 | Carter et al. |
| 6,727,225 B2 | 4/2004 | Wiley |
| 7,025,962 B1 | 4/2006 | Gorman et al. |
| 7,361,760 B2 | 4/2008 | Sircar et al. |
| 7,618,632 B2 | 11/2009 | Collins et al. |
| 7,812,135 B2 | 10/2010 | Smith et al. |
| 8,388,967 B2 | 3/2013 | Smith et al. |
| 8,586,023 B2 | 11/2013 | Shiku et al. |
| 8,591,886 B2 | 11/2013 | Ponath et al. |
| 10,519,146 B2 | 12/2019 | Lanman et al. |
| 10,532,042 B2 | 1/2020 | Lanman et al. |
| 10,640,504 B2 | 5/2020 | Lanman et al. |
| 10,988,485 B2 | 4/2021 | Minatti et al. |
| 2002/0042368 A1 | 4/2002 | Fanslow, III et al. |
| 2003/0105091 A1 | 6/2003 | Riedl et al. |
| 2003/0162712 A1 | 8/2003 | Cerretti et al. |
| 2009/0012085 A1 | 1/2009 | Baum et al. |
| 2014/0288045 A1 | 9/2014 | Ren et al. |
| 2015/0239900 A1 | 8/2015 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2018/0015087 A1 | 1/2018 | Liu et al. |
| 2018/0072723 A1 | 3/2018 | Blake et al. |
| 2019/0343838 A1 | 11/2019 | Allen et al. |
| 2019/0345169 A1 | 11/2019 | Minatti et al. |
| 2019/0374542 A1 | 12/2019 | Allen et al. |
| 2019/0375749 A1 | 12/2019 | Chen et al. |

(Continued)

FOREIGN PATENT DOCUMENTS

| DE | 19629652 A1 | 1/1998 |
| EP | 0090505 A2 | 10/1983 |

(Continued)

OTHER PUBLICATIONS

The ASCO Post Staff, AACR-NCI-EORTC: Investigational KRAS G12C inhibitor for KRAS-Mutant Soild Tumors, 2 pages, Nov. 2019.*

(Continued)

*Primary Examiner* — Deepak R Rao
(74) *Attorney, Agent, or Firm* — Markus Bergauer

(57) ABSTRACT

Provided herein are KRAS G12C inhibitors, composition of the same, and methods of using the same. These inhibitors are useful for treating a number of disorders, including pancreatic, colorectal, and lung cancers.

34 Claims, No Drawings

(56) References Cited

U.S. PATENT DOCUMENTS

| | | | |
|---|---|---|---|
| 2020/0030324 A1 | 1/2020 | Booker et al. |
| 2020/0055845 A1 | 2/2020 | Lanman et al. |
| 2020/0069657 A1 | 3/2020 | Lanman et al. |
| 2020/0165231 A1 | 5/2020 | Shin et al. |
| 2020/0207766 A1 | 7/2020 | Lanman et al. |
| 2020/0216446 A1 | 7/2020 | Parsons et al. |
| 2020/0222407 A1 | 7/2020 | Lipford et al. |
| 2020/0360374 A1 | 11/2020 | Henary et al. |
| 2020/0369662 A1 | 11/2020 | Chaves et al. |
| 2021/0009577 A1 | 1/2021 | Lanman et al. |

FOREIGN PATENT DOCUMENTS

| | | |
|---|---|---|
| EP | 0520722 A1 | 12/1992 |
| EP | 0566226 A1 | 10/1993 |
| EP | 0606046 A1 | 7/1994 |
| EP | 0682027 A1 | 11/1995 |
| EP | 0407122 A1 | 10/1996 |
| EP | 0770622 A2 | 5/1997 |
| EP | 0780386 A1 | 6/1997 |
| EP | 0787772 A2 | 8/1997 |
| EP | 0818442 A2 | 1/1998 |
| EP | 0837063 A1 | 4/1998 |
| EP | 0931788 A2 | 7/1999 |
| EP | 0970070 B1 | 1/2000 |
| EP | 1004578 A2 | 5/2000 |
| EP | 1181017 B1 | 2/2002 |
| EP | 1786785 B9 | 5/2007 |
| EP | 1866339 B1 | 12/2007 |
| EP | 1947183 A1 | 7/2008 |
| EP | 3401314 A1 | 11/2019 |
| EP | 3055290 B1 | 12/2019 |
| JP | 02233610 A | 9/1990 |
| WO | 1990005719 A1 | 5/1990 |
| WO | 1992005179 A1 | 4/1992 |
| WO | 1992020642 A1 | 11/1992 |
| WO | 1993011130 A1 | 6/1993 |
| WO | 1994002136 A1 | 2/1994 |
| WO | 1994002485 A1 | 2/1994 |
| WO | 1994009010 A1 | 4/1994 |
| WO | 1995009847 A1 | 4/1995 |
| WO | 1995014023 A1 | 5/1995 |
| WO | 1995016691 A1 | 6/1995 |
| WO | 1995019774 A1 | 7/1995 |
| WO | 1995019970 A1 | 7/1995 |
| WO | 1996027583 A1 | 9/1996 |
| WO | 1996030347 A1 | 10/1996 |
| WO | 1996031510 A1 | 10/1996 |
| WO | 1996033172 A1 | 10/1996 |
| WO | 1996033980 A1 | 10/1996 |
| WO | 1996041807 A1 | 12/1996 |
| WO | 1997002266 A1 | 1/1997 |
| WO | 1997013771 A1 | 4/1997 |
| WO | 1997019065 A1 | 5/1997 |
| WO | 1997027199 A1 | 7/1997 |
| WO | 1997030034 A1 | 8/1997 |
| WO | 1997030044 A1 | 8/1997 |
| WO | 1997032880 A1 | 9/1997 |
| WO | 1997032881 A1 | 9/1997 |
| WO | 1997034895 A1 | 9/1997 |
| WO | 1997038983 A1 | 10/1997 |
| WO | 1997038994 A1 | 10/1997 |
| WO | 1997049688 A1 | 12/1997 |
| WO | 1998002434 A1 | 1/1998 |
| WO | 1998002437 A1 | 1/1998 |
| WO | 1998002438 A1 | 1/1998 |
| WO | 1998002441 A2 | 1/1998 |
| WO | 1998003516 A1 | 2/1998 |
| WO | 1998007697 A1 | 2/1998 |
| WO | 1998007726 A1 | 2/1998 |
| WO | 1998014449 A1 | 4/1998 |
| WO | 1998014450 A1 | 4/1998 |
| WO | 1998014451 A1 | 4/1998 |
| WO | 1998017662 A1 | 4/1998 |
| WO | 1998030566 A1 | 7/1998 |
| WO | 1998033768 A1 | 8/1998 |
| WO | 1998033798 A2 | 8/1998 |
| WO | 1998034915 A1 | 8/1998 |
| WO | 1998034918 A1 | 8/1998 |
| WO | 1999007675 A1 | 2/1999 |
| WO | 1999007701 A1 | 2/1999 |
| WO | 1999020758 A1 | 4/1999 |
| WO | 1999029667 A1 | 6/1999 |
| WO | 1999035132 A1 | 7/1999 |
| WO | 1999035146 A1 | 7/1999 |
| WO | 1999040196 A1 | 8/1999 |
| WO | 1999045009 A1 | 9/1999 |
| WO | 1999052889 A1 | 10/1999 |
| WO | 1999052910 A1 | 10/1999 |
| WO | 1999061422 A1 | 12/1999 |
| WO | 2000002871 A1 | 1/2000 |
| WO | 2000012089 A1 | 3/2000 |
| WO | 2000059509 A1 | 10/2000 |
| WO | 2001003720 A2 | 1/2001 |
| WO | 2001014387 A1 | 3/2001 |
| WO | 2001032651 A1 | 5/2001 |
| WO | 2001037820 A2 | 5/2001 |
| WO | 2002055501 A2 | 7/2002 |
| WO | 2002059110 A1 | 8/2002 |
| WO | 2002066470 A1 | 8/2002 |
| WO | 2002068406 A2 | 9/2002 |
| WO | 2004005279 A2 | 1/2004 |
| WO | 2004007458 A1 | 1/2004 |
| WO | 2004007481 A2 | 1/2004 |
| WO | 2004009784 A2 | 1/2004 |
| WO | 2005005434 A1 | 1/2005 |
| WO | 2005007190 A1 | 1/2005 |
| WO | 2005011700 A1 | 2/2005 |
| WO | 2005016252 A2 | 2/2005 |
| WO | 2005021546 A1 | 3/2005 |
| WO | 2005055808 A2 | 6/2005 |
| WO | 2005115451 A2 | 12/2005 |
| WO | 2006044453 A1 | 4/2006 |
| WO | 2006083289 A2 | 8/2006 |
| WO | 2006121168 A1 | 11/2006 |
| WO | 2006122806 A2 | 11/2006 |
| WO | 2007133822 A1 | 11/2007 |
| WO | 2008070740 A1 | 6/2008 |
| WO | 2009036082 A2 | 3/2009 |
| WO | 2009055730 A1 | 4/2009 |
| WO | 2010003118 A1 | 1/2010 |
| WO | 2011028683 A1 | 3/2011 |
| WO | 2011051726 A2 | 5/2011 |
| WO | 2011090754 A1 | 7/2011 |
| WO | 2012142498 A2 | 10/2012 |
| WO | 2013039954 A1 | 3/2013 |
| WO | 2013155223 A1 | 10/2013 |
| WO | 2014143659 A1 | 9/2014 |
| WO | 2014152588 A1 | 9/2014 |
| WO | 2015001076 A1 | 1/2015 |
| WO | 2015054572 A1 | 4/2015 |
| WO | 2015075483 A1 | 5/2015 |
| WO | 2016044772 A1 | 3/2016 |
| WO | 2016049524 A1 | 3/2016 |
| WO | 2016049565 A1 | 3/2016 |
| WO | 2016049568 A1 | 3/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017100546 A1 | 6/2017 |
| WO | 2017172979 A1 | 10/2017 |
| WO | 2017201161 A1 | 11/2017 |
| WO | 2018064510 A1 | 4/2018 |
| WO | 2018068017 A1 | 4/2018 |
| WO | 2018119183 A3 | 6/2018 |
| WO | 2018140598 A1 | 8/2018 |

(56) References Cited

FOREIGN PATENT DOCUMENTS

| | | | |
|---|---|---|---|
| WO | 2018217651 A1 | 11/2018 | |
| WO | 2018218069 A1 | 11/2018 | |
| WO | 2019051291 A1 | 3/2019 | |
| WO | 2019213516 A1 | 11/2019 | |
| WO | 2019213526 A1 | 11/2019 | |
| WO | 2019217691 A1 | 11/2019 | |
| WO | 2019232419 A1 | 12/2019 | |
| WO | 2019241157 A1 | 12/2019 | |
| WO | 2019243533 A1 | 12/2019 | |
| WO | 2019243535 A1 | 12/2019 | |
| WO | 2020050890 A2 | 3/2020 | |
| WO | 2020102730 A1 | 5/2020 | |
| WO | 2020106640 A1 | 5/2020 | |
| WO | 2020156285 A1 | 8/2020 | |
| WO | 2020232130 A1 | 11/2020 | |
| WO | 2020236947 A1 | 11/2020 | |
| WO | 2020236948 A1 | 11/2020 | |
| WO | 2021081212 A1 | 4/2021 | |

OTHER PUBLICATIONS

Hallin et al., The KRAS Inhibitor, MRTX849, Provides Insight Toward Therapeutic Susceptibility of KRAS Mutant Cancers in Mouse Models and Patients, 35 pages, Oct. 2019.*

Hichri et al., CAPLUS Abstract 162:245378 (2015).*

Acute Leukemia, Merck Manual (Online Edition) 6 pages, pp. 1-6 (2013).*

Simone, Oncology: Introduction, Cecil Textbook of Medicine, 20th Edition, vol. 1, pp. 1004-1010, 1996.*

Pearce et al., Failure modes in anticancer drug discovery and development, Cancer Drug Design and Discovery Edited by Stephen Neidle, Chapter 18, pp. 424-435 (2008).*

Gura, Systems for identifying New Drugs are Often Faulty, Cancer Models, Science, vol. 278, No. 5340, pp. 1041-1042, Nov. 1997.*

Johnson et al., Relationships between drug activity in NCI preclinical in vitro and in vivo models and early clinical trials, British Journal of Cancer (2001) 64(10): 1424-1431.*

"A Phase 1, Study Evaluating the Safety, Tolerability, PK, and Efficacy of AMG 510 in Subjects With Solid Tumors With a S Mutation." NCT03600883, comparison of version submitted Jul. 17, 2018 and Apr. 3, 2019 (update posted Apr. 5, 2019), https://www.clinicaltrials.gov/ct2/history/NCT03600883 (last accessed Apr. 25, 2020), pp. 1-7.

"KRASG12C Inhibitor," Mirati Therapeutics, retrieved on Nov. 27, 2018, from https://www.mirati.com/mrtx849/, 5 pages.

Ahmadian, et al., "Guanosine triphosphatase stimulation of oncogenic Ras mutants," PNAS, 96: 7065-7070, 1999.

Airoldi, et al., "Glucose-Derived Ras Pathway Inhibitors: Evidence of Ras-Ligand Binding and Ras-GEF (Cdc25) Interaction Inhibition," ChemBioChem, 8: 1376-1379 (2007).

ATTC "Organism: Mus musculus (B cell); Mus musculus (myeloma), mouse (B cell); mouse (myeloma)," Accession No. HB-8508, retrieved from https://www.atcc.org/~/media/0DF7351153724BD6A3E7D78D5BA2F933.ashx, on Nov. 29, 2018.

Barnett, et al., "Identification and characterization of pleckstrin-holomogy-domain-dependent and isoenzyme specific Akt inhibitors," Biochem. J.,385 (2): 399-408 (2005).

Bhatia, et al., "A Review on Bioisosterism: A Rational Approach for Drug Design and Molecular Modification," Pharmacologyonline, 1:272-299 (2011).

Bull, et al., "Isoquino[2,1-c][1,3,2] Benzodiazaphosphorine Derivatives: New Potential Agents for Cancer Chemotherapy," Phosphorus, Sulfur, and Silicon, 162:231-243 (2000).

Campillo, et al., "Novel Bronchodilators: Synthesis, Transamination Reactions, and Pharmacology of a Series of Pyrazino[2,3-c][1,2,6]thiadiazine 2,2-Dioxides," J. Med. Chem., 43: 4219-4227 (2000).

Canon, et al., "The clinical KRAS(G12C) inhibitor AMG 510 drives anti-tumour immunity," Nature, 575(7781): 217-223 (2019).

Cee, et al.,"Discovery of AMG 510, a first-in-humancovalent inhibitor of KRAS$^{G12C}$ for the treatment of solid tumors," Abstract and Presentation, ACS Spring Meeting, Orlando, FL, USA, Mar. 31-Apr. 4, 2019.

Cohen, "The development and therapeutic potential of protein kinase inhibitors," Current Opinion in Chemical Biology, 3:459-465 (1999).

Cowen Slide deck—Warp Drive Bio, slides 1-32, "Corporate Overview Exploiting the Molecules and Mechanisms of Nature to Create Transformative Medicines" http://www.warpdrivebio.com/news/cowen%202016.pdf (last visited Apr. 2016).

Dasmahapatra, et al., "In vitro Combination Treatment with Perifosine and UCN-01 Demonstrates Synergism Against Prostate (PC-3) and Lung (A549) Epithelial Adenocarcinoma Cell Lines," Clin. Cancer Res. 10(15): 5242-5252 (2004).

Dermer, et al., "Another Anniversary for the War on Cancer," Bio/Technology, 12: 320 (1994).

Douelle, et al., "Highly Diastereoselective Synthesis of vicinal Quaternary and Tertiary Stereocenters Using the Iodo-aldol Cyclization," Org. Lett., 9 (10): 1931-1934 (2007).

Erkkilä, et al., "Mild Organocatalytic α-Methylenation of Aldehydes," J. Org. Chem.,71 (6), 2538-2541 (2006).

Extended European Search Report for European Patent Application No. 19208193.2, dated Jun. 3, 2020, pp. 1-8.

Fakih, et al., "Phase 1 study evaluating the safety, tolerability, pharmacokinetics (PK), and efficacy of AMG 510, a novel small molecule KRASG12C inhibitor, in advanced solid tumors," Journal of Clinical Oncology, 37(15 suppl) (May 20, 2019) 3003, published online May 26, 2019.

Fakih, et al., "Phase 1 study evaluating the safety, tolerability, pharmacokinetics (PK), and efficacy of AMG 510, a novel small molecule KRASG12C inhibitor, in advanced solid tumors," Presentation, ASCO, Chicago, IL, USA, May 31-Jun. 4, 2019.

Final Office Action for U.S. Appl. No. 15/984,855, dated Mar. 28, 2019, 7 pages.

Final Office Action for U.S. Appl. No. 16/661,907, dated Mar. 27, 2020, 29 pages.

Freshney, et al., Culture of Animal Cells, A Manual of Basic Technique, Alan R. Liss, Inc, New York, p. 4 (1983).

Gentile, et al., "Discovery and Structural Investigation of Novel Binders to the Ras Switch II Pocket," NCI Initiative Symposium Poster (2015).

Gills and Dennis, "The development of phosphatidylinositol ether lipid analogues as inhibitors of the serine/threonine kinase, Akt," Expert. Opin. Investig. Drugs, 13: 787-797 (2004).

Goldberg, et al., "Role of PD-1 and its ligand, B7-H1, in early fate decisions of CD8 T cells," Blood,110(1): 186-192 (2007).

Goldstein, et al., "Biological efficacy of a chimeric antibody to the epidermal growth factor receptor in a human tumor xenograft model," Clin. Cancer Res., 1: 1311-1318 (1995).

Golub, et al., "Molecular Classification of Cancer: Class Discovery and Class Prediction by Gene Expression Monitoring," Science, 286: 531-537(1999).

Govindan, et al., "Safety, Efficacy, and Pharmacokinetics of AMG 510, a Novel KRASG12C Inhibitor, in Patients with Non-Small Cell Lung Cancer," Abstract and Presentation, North American Conference on Lung Cancer (NACLC), Chicago, IL, USA, Oct. 10-12, 2019.

Govindan, et al., "Phase 1 Study of AMG 510, a Novel KRAS G12C Inhibitor, in Advanced Solid Tumors with KRAS p.G12C Mutation," Abstract, ESMO Congress, Barcelona, Spain, Sep. 27-Oct. 1, 2019.

Govindan, et al., "Phase 1 Study of AMG 510, a Novel KRAS G12C Inhibitor, in Advanced Solid Tumors with KRAS p.G12C Mutation," Poster, ESMO Congress, Barcelona, Spain, Sep. 27, 2019-Oct. 1, 2019.

Govindan, et al., "Phase 1 Study of Safety, Tolerability, Pharmacokinetics, and Efficacy of AMG510, a Novel KRASG12C Inhibitor, in Non-Small Cell Lung Cancer," Abstract and Presentation, World Conference on Lung Cancer (WCLC), Barcelona, Spain, Sep. 7-10, 2019.

Halford, "Amgen unveils its Kras covalent inhibitor AMG 510," Chemical & Engineering News 97(14):4 (2019).

(56) References Cited

OTHER PUBLICATIONS

Hallin, et al., "The KRAS$^{G12C}$ Inhibitor MRTX849 Provides Insight toward Therapeutic Susceptibility of KRAS-Mutant Cancers in Mouse Models and Patients," *Cancer Discov.*, 10: 54-71 (2020).
Hansen, et al., "Abstract 686: Drugging an undruggable pocket: the biochemical mechanism of covalent KRAS$^{G12C}$ inhibitors," Proceedings of the American Association for Cancer Research Annual Meeting 2018; Apr. 14-18, 2018; Chicago, IL; AACR; Cancer Res., 78(13 Suppl): Abstract 686 (2018).
Hichri, et al., "A Convenient Synthesis of 1,3,2-Benzodiazaphophorine-2-Oxide," *Phosphorus, Sulfur, and Silicon*, 190: 29-35 (2015).
Hocker, et al., "Andrographolide derivatives inhibit guanine nucleotide exchange and abrogate oncogenic Ras function," *PNAS*, 110(25): 10201-10206 (2013).
Huang, et al., "Epidermal Growth Factor Receptor Blockade with C225 Modulates Proliferation, Apoptosis, and Radiosensitivity in Squamous Cell Carcinomas of the Head and Neck," *Cancer Res.*, 59(8): 1935-1940 (1999).
International Search Report for PCT/US2017/067801, dated Jul. 25, 2018, 6 pages.
International Search Report for PCT/US2018/033714, dated Jul. 17, 2018, 3 pages.
International Search Report for PCT/US2018/050044, dated Oct. 30, 2018, 7 pages.
International Search Report for PCT/US2019/030593, dated Aug. 6, 2019, 4 pages.
International Search Report for PCT/US2019/030606, dated Jul. 23, 2019, 5 pages.
International Search Report for PCT/US2019/031535, dated Jul. 25, 2019, 7 pages.
International Search Report for PCT/US2019/034974, dated Aug. 9, 2019, 5 pages.
International Search Report for PCT/US2019/036397, dated Aug. 26, 2019, 5 pages.
International Search Report for PCT/US2019/036626, dated Jun. 2, 2020, 5 pages.
International Search Report for PCT/US2019/061815, dated Mar. 5, 2020, 6 pages.
International Search Report for PCT/US2019/062051, dated Mar. 2, 2020, 3 pages.
International Search Report for PCT/US2020/032686, dated Aug. 14, 2020, 5 pages.
International Search Report for PCT/US2020/033831, dated Jul. 9, 2020, 6 pages.
International Search Report for PCT/US2020/033832, dated Jul. 8, 2020, 4 pages.
Janes, et al., "Targeting KRAS Mutant Cancers with a Covalent G12C-Specific Inhibitor," *Cell*, 172: 578-589 (2018).
Janeway et al., "Immunobiology: The Immune System in Health and Disease", Elsevier Science Ltd./Garland Publishing, 4th ed. (1999). Table of contents.
Jarvis, "Notorious KRAS: Taking down cancer researchers' biggest foe," *Chemical & Engineering News*, 97(37), 9 pages (2019).
Jin, et al., "Inhibition of AKT survival pathway by a small molecule inhibitor in human endometrial cancer cells," *Br. J. Cancer*, 91: 1808-1812 (2004).
Lanman, et al., "Abstract 4455: Discovery of AMG 510, a first-in-human covalent inhibitor of KRAS$^{G12C}$ for the treatment of solid tumors," Presentation, American Association for Cancer Research (AACR) Annual Meeting, Atlanta, GA, USA, Mar. 29-Apr. 3, 2019.
Lanman, et al., "Abstract 4455: Discovery of AMG 510, a first-in-human covalent inhibitor of KRAS$^{G12C}$ for the treatment of solid tumors," Proceedings of the American Association for Cancer Research Annual Meeting 2019; Mar. 29-Apr. 3, 2019; Atlanta, GA, USA, AACR, *Cancer Res*. 79(13 Suppl): Abstract nr 4455 (2019).
Lanman, et al., "Discovery of a Covalent Inhibitor of KRAS$^{G12C}$ (AMG 510) for the Treatment of Solid Tumors," *J. Med. Chem.*, 63: 52-65 (2020).
Li, et al., "Targeting Protein-Protein Interaction with Covalent Small-Molecule Inhibitors," *Current Topics in Medicinal Chemistry*, 19(21): 1872-1876 (2019).
Lim, et al., "Therapeutic Targeting of Oncogenic K-Ras by a Covalent Catalytic Site Inhibitor," *Angew. Chem. Int. Ed*, 53: 199-204 (2014).
Lipford, et al., "Pre-Clinical Development of AMG 510: The First Inhibitor of KRAS$^{G12C}$ in Clinical Testing," Presentation, American Association for Cancer Research (AACR) Annual Meeting, Atlanta, GA, USA, Mar. 29-Apr. 3, 2019.
Liu, Y., "Session SY28—Transformative Small Molecule Therapies—Targeting KRAS mutant cancers with a covalent G12C—specific inhibitor," Presentation on Apr. 4, 2017, AACR Annual Meeting Presentation, Apr. 1-5, 2017, Washington, D.C. (2017).
Lopez, et al.,"Optimization of quinazolinone-based covalent inhibitors of KRAS$^{G12C}$ in the discovery of AMG 510," Abstract and Poster, ACS Fall Meeting, San Diego, CA, USA, Aug. 25-29, 2019.
Lu, et al., "KRAS G12C Drug Development: Discrimination between Switch II Pocket Configurations Using Hydrogen/Deuterium-Exchange Mass Spectrometry," *Structure*, 25: 1-7 (2017).
Maurer, et al., "Small-molecule ligands bind to a distinct pocket in Rad and inhibit SOS-mediated nucleotide exchange activity," *PNAS*, 109(14): 5299-5304 (2012).
McGregor, et al., "Expanding the Scope of Electrophiles Capable of Targeting K-Ras Oncogenes," *ACS Bio. Chem.*, 56: 3179-3183 (2017).
Mirati Therapeutics, "Corporate Presentation Nov. 2017," Slides 1-41 (2017).
Modjtahedi, et al., "The human Egf receptor as a target for cancer therapy: six new rat mAbs AGainst the receptor on the breast carcinoma MDA-MB 468," *Br. J. Cancer*, 67(2): 247-253 (1993).
Morrissey et al., "Immunotherapy and Novel Combinations in Oncology: Current Landscape, Challenges, and Opportunities," *Clin. Transl. Sci.*, 9(2):89-104 (2016).
National Cancer Institute identifier: NSC 154020, retrieved on Nov. 29, 2018, from https://cactus.nci.nih.gov/ncidb2.2/.
NCBI Reference Sequence, "GTPase KRas isoform a [*Homo sapiens*]," GenBank Accession No. NM_203524.1, Retrieved on Nov. 29, 2018 from https://www.ncbi.nlm.nih.gov/protein/15718763?sat=4&satkey=234448549, 4 pages.
Non-Final Office Action (Corrected) for U.S. Appl. No. 16/125,359, dated Apr. 8, 2019, 13 pages.
Non-Final Office Action for U.S. Appl. No. 15/849,905, dated Mar. 20, 2019, 18 pages.
Non-Final Office Action for U.S. Appl. No. 15/984,855, dated Sep. 27, 2018, 25 pages.
Non-Final Office Action for U.S. Appl. No. 16/125,359, dated Apr. 5, 2019, 13 pages.
Non-Final Office Action for U.S. Appl. No. 16/402,538, dated Oct. 30, 2019, 12 pages.
Non-Final Office Action for U.S. Appl. No. 16/402,589, dated Mar. 6, 2020, 17 pages.
Non-Final Office Action for U.S. Appl. No. 16/407,889, dated Jul. 1, 2020, 6 pages.
Non-Final Office Action for U.S. Appl. No. 16/436,647, dated Aug. 7, 2020, 19 pages.
Non-Final Office Action for U.S. Appl. No. 16/438,349, dated Dec. 13, 2019, 15 pages.
Non-Final Office Action for U.S. Appl. No. 16/661,907, dated Nov. 18, 2019, 20 pages.
Notice of Allowance dated Jul. 24, 2020 for U.S. Appl. No. 16/402,538, 8 pages.
Ostrem, et al., "Development of mutant-specific small molecule inhibitors of K-Ras," Poster, AACR 104th Annual Meeting 2013; Apr. 6-10, 2013; Washington, D.C. (2013).
Ostrem, et al., "K-Ras(G12C) inhibitors allosterically control GTP affinity and effector interactions," *Nature*, 503: 548-551 (2013).
Paez, et al., "EGFR Mutations in Lung Cancer Correlation with Clinical Response to Gefitinib Therapy," *Science,* 304(5676): 1497-500 (2004).
Palmioli, et al., "First experimental identification of Ras-inhibitor binding interface using a water-soluble Ras ligand," *Bioorg. Med. Chem. Lett.*, 19: 4217-4222 (2009).

(56) References Cited

OTHER PUBLICATIONS

Patricelli, et al., "Selective Inhibition of Oncogenic KRAS Output with Small Molecules Targeting the Inactive State," *Cancer Discov*, 6 (3): 316-329 (2016).
Peri, et al., "Design, Synthesis and Biological Evaluation of Sugar-Derived Ras Inhibitors," *ChemBioChem*, 6: 1839-1848 (2005).
Peri, et al., "Sugar-Derived Ras Inhibitors: Group Epitope Mapping by NMR Spectroscopy and Biological Evaluation," *Eur. J. Org. Chem.*, 16: 3707-3720 (2006).
Peters, et al., "Selective inhibition of K-Ras G12C through allosteric control of GTP affinity and effector interactions," EORTC Poster (2013).
Remington's Pharmaceutical Sciences, 1435-1712 (18th ed., Mack Publishing Co, Easton, Pennsylvania, 1990 (Table of Contents Only).
Rex et al., "KRAS—AACR 2018," Amgen Collection of Information published at Proceedings of the American Association for Cancer Research Annual Meeting 2018; Apr. 14-18, 2018; Chicago, IL; AACR; slides 1-24 (2018).
Rex, et al., "Abstract 3090: In vivo characterization of AMG 510—a potent and selective KRAS$^{G12C}$ covalent small molecule inhibitor in preclinical KRAS$^{G12C}$ cancer models," Poster, American Association for Cancer Research (AACR) Annual Meeting, Atlanta, GA, USA, Mar. 29-Apr. 3, 2019.
Rex, et al., "Abstract 3090: In vivo characterization of AMG 510—a potent and selective KRAS$^{G12C}$ covalent small molecule inhibitor in preclinical KRAS$^{G12C}$ cancer models," Proceedings of the American Association for Cancer Research Annual Meeting 2019; Mar. 29-Apr. 3, 2019; Atlanta, GA, USA, AACR, *Cancer Res.* 79(13 Suppl): Abstract nr 3090 (2019).
Saiki, et al., "Abstract 4484: Discovery and in vitro characterization of AMG 510—a potent and selective covalent small-molecule inhibitor of KRAS$^{G12C}$," Presentation, American Association for Cancer Research (AACR) Annual Meeting, Atlanta, GA, USA, Mar. 29-Apr. 3, 2019.
Saiki, et al., "Abstract 4484: Discovery and in vitro characterization of AMG 510—a potent and selective covalent small-molecule inhibitor of KRAS$^{G12C}$," Proceedings of the American Association for Cancer Research Annual Meeting 2019; Mar. 29-Apr. 3, 2019; Atlanta, GA, USA, AACR, *Cancer Res.* 79(13 Suppl): Abstract nr 4484 (2019).
Sarkar, et al., "Indole-3-Carbinol and Prostate Cancer[1,2]," *J. Nutr.*, 134(12 Suppl): 3493S-3498S (2004).
Shima, et al., "In silico discovery of small-molecule Ras inhibitors that display antitumor activity by blocking the Ras-effector interaction," *PNAS*, 110(20): 8182-8187 (2013).
Singh, et al., "Improving Prospects for Targeting RAS," *J. Clinc. Oncl*, 33(31): 3650-3660 (2015).
Statsyuk, "Let K-Ras activate its own inhibitor," *Nature Structural & Molecular Biology*, 25:435-439 (2018).
Sun, et al., "Discovery of Small Molecules that Bind to K-Ras and Inhibit Sos-Mediated Activation," *Angew. Chem. Int. Ed.*, 51: 6140-6143 (2012).
Taveras, et al., "Ras Oncoprotein Inhibitors: The Discovery of Potent, Ras Nucleotide Exchange Inhibitors and the Structural Determination of a Drug-Protein Complex," *Biorg. Med. Chem. Lett.,*, 5(1): 125-133 (1997).
Teraivioto, et al., 1996, Cancer 77 (4):639-645.
Thompson, et al., "PD-1 Is Expressed by Tumor-Infiltrating Immune Cells and Is Associated with Poor Outcome for Patients with Renal Cell Carcinoma," *Clin. Cancer Res.*, 13(6): 1757-1761 (2007).
Traxler, "Tyrosine kinase inhibitors in cancer treatment (Part II)," *Exp. Opin. Ther. Patents*, 8(12): 1599-1625 (1998).
U.S. Appl. No. 60/528,340, filed Dec. 9, 2003.
Wang, et al., "Ras inhibition via direct Ras binding—is there a path forward?," *Bioorg. Med. Chem. Lett.*, 22: 5766-5776 (2012).
Written Opinion for PCT/US2017/067801, dated Jul. 25, 2018, 10 pages.
Written Opinion for PCT/US2018/033714, dated Jul. 17, 2018, 5 pages.
Written Opinion for PCT/US2018/050044, dated Oct. 30, 2018, 7 pages.
Written Opinion for PCT/US2019/030593, dated Aug. 6, 2019, 5 pages.
Written Opinion for PCT/US2019/030606, dated Jul. 23, 2019, 6 pages.
Written Opinion for PCT/US2019/031535, dated Jul. 25, 2019, 7 pages.
Written Opinion for PCT/US2019/034974, dated Aug. 9, 2019, 5 pages.
Written Opinion for PCT/US2019/036397, dated Aug. 26, 2019, 5 pages.
Written Opinion for PCT/US2019/036626, dated Jun. 2, 2020, 12 pages.
Written Opinion for PCT/US2019/061815, dated Mar. 5, 2020, 4 pages.
Written Opinion for PCT/US2019/062051, dated Mar. 2, 2020, 5 pages.
Written Opinion for PCT/US2020/032686, dated Aug. 14, 2020, 6 pages.
Written Opinion for PCT/US2020/033831, dated Jul. 9, 2020, 7 pages.
Written Opinion for PCT/US2020/033832, dated Jul. 8, 2020, 6 pages.
Xiong, et al., "Covalent Guanosine Mimetic Inhibitors of G12C KRAS," *ACS Med. Chem. Lett.*, 8: 61-66 (2017).
Yan, et al., "Pharmacogenetics and pharmacogenomics in oncology therapeutic antibody development," *BioTechniques*, 29(4): 565-568 (2005).
Yang, et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).
Yang, et al., "Eradication of Established Tumors by a Fully Human Monoclonal Antibody to the Epidermal Growth Factor Receptor without Concomitant Chemotherapy," *Cancer Res.*, 59: 1236-1243 (1999).
Zeng, et al., "Potent and Selective Covalent Quinazoline Inhibitors of KRAS G12C," *Cell Chemical Biology*, 24: 1-12 (2017).
Zimmerman, et al., "Small molecule inhibition of the KRAS—PDEδ interaction impairs oncogenic KRAS signaling," *Nature*, 1-5 (2017).
International Search Report for PCT/US2019/62064, dated Oct. 29, 2020, 9 pages.
Non-Final Office Action for U.S. Appl. No. 16/428,163, dated Sep. 15, 2020, 6 pages.
Notice of Allowance dated Nov. 16, 2020 for U.S. Appl. No. 16/402,538, 8 pages.
Notice of Allowance dated Sep. 9, 2020 for U.S. Appl. No. 16/438,349, 9 pages.
Written Opinion for PCT/US2019/62064, dated Oct. 29, 2020, 13 pages.
AMG-510; CS-0081316; Source: AbaChemScene (CS-0081316); Deposit Date: May 13, 2019 Available Date: May 13, 2019; SID: 384060804[CID: 137278711] (available at https://pubchem.ncbi.nlm.nih.gov/substance/384060804/).
AMG-510; HY-114277; Source: MedChemexpress MCE (HY-114277); Deposit Date: May 13, 2019 Available Date: May 13, 2019; SID: 384060569[CID: 137278711] (available at https://pubchem.ncbi.nlm.nih.gov/substance/384060569).
Canon, et al., "The clinical KRAS(G12C) inhibitor AMG 510 drives anti-tumour immunity," *Nature*, 575(7781): 217-223 (2019) (Supplementary Material, pp. 1-55).
Database Registry [Online], Chemical Abstracts Service, Columbus, Ohio, US; Jul. 31, 2017 (Jul. 31, 2017), XP002801805, retrieved from STN Database accession No. 2105944-09-8.
Final Office Action for U.S. Appl. No. 16/436,647, dated Mar. 24, 2021, 7 pages.
Non-Final Office Action for U.S. Appl. No. 16/675,121, dated Feb. 2, 2021, 10 pages.
Non-Final Office Action for U.S. Appl. No. 16/817,109, dated Mar. 3, 2021, 12 pages.

(56) References Cited

OTHER PUBLICATIONS

Notice of Allowance, dated Dec. 21, 2020, for U.S. Appl. No. 16/407,889, 5 pages.
Notice of Allowance, dated Feb. 18, 2021, for U.S. Appl. No. 16/687,546, 9 pages.
Notice of Allowance, dated Jan. 26, 2021, for U.S. Appl. No. 16/438,349, 9 pages.
Notice of Allowance, dated Jan. 27, 2021, for U.S. Appl. No. 16/428,163, 9 pages.
Notice of Allowance, dated Mar. 30, 2021, for U.S. Appl. No. 16/402,538, 8 pages.
Meanwell, "Synopsis of Some Recent Tactical Application of Bioisosteres in Drug Design," *J. Med Chem.* 54:2529-2591 (2011).
Shibata et al., "A Convenient Synthesis of 3-Cyano-2-methylpyridines under Ultrasonic Irradiation," *Bull. Chem. Soc. Jpn.*, 61:2199-2200 (1988).
Stanetty et al., "Synthesis of Aza Analogs of the Herbicide Sindone B," *Monatshefte Fuer Chemie*, 130:441-450 (1999).
Third Party Observation filed for PCT/US2020/033831, submitted Jan. 15, 2021, 2 pages.

\* cited by examiner

KRAS G12C INHIBITORS AND METHODS OF USING THE SAME

CROSS REFERENCE TO RELATED APPLICATION

This application claims priority to U.S. Provisional Application No. 62/667,314, filed on May 4, 2018, which specification is hereby incorporated herein by reference in its entirety.

FIELD OF THE INVENTION

The present invention relates to compounds that inhibit the KRAS G12C protein; methods of treating diseases or conditions, such as cancer, using the compounds; and pharmaceutical compositions containing the compounds.

BACKGROUND

KRAS gene mutations are common in pancreatic cancer, lung adenocarcinoma, colorectal cancer, gall bladder cancer, thyroid cancer, and bile duct cancer. KRAS mutations are also observed in about 25% of patients with NSCLC, and some studies have indicated that KRAS mutations are a negative prognostic factor in patients with NSCLC. Recently, V-Ki-ras2 Kirsten rat sarcoma viral oncogene homolog (KRAS) mutations have been found to confer resistance to epidermal growth factor receptor (EGFR) targeted therapies in colorectal cancer; accordingly, the mutational status of KRAS can provide important information prior to the prescription of TKI therapy. Taken together, there is a need for new medical treatments for patients with pancreatic cancer, lung adenocarcinoma, or colorectal cancer, especially those who have been diagnosed to have such cancers characterized by a KRAS mutation, and including those who have progressed after chemotherapy.

The compounds disclosed herein can be in the form of a pharmaceutically acceptable salt. The compounds provided can be formulated into a pharmaceutical formulation comprising a compound disclosed herein and a pharmaceutically acceptable excipient.

Also provided is a method of inhibiting KRAS G12C in a cell, comprising contacting the cell with a compound or composition disclosed herein. Further provided is a method of treating cancer in a subject comprising administering to the subject a therapeutically effective amount of a compound or composition disclosed herein. In some embodiments, the cancer is lung cancer, pancreatic cancer, or colorectal cancer.

SUMMARY

In one aspect of the present invention, the invention provides a compound having a structure of formula (I)

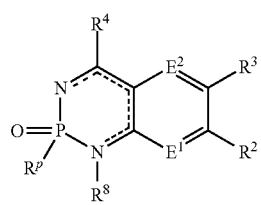

(I)

wherein $E^1$ and $E^2$ are each independently N or $CR^1$;

≡≡≡ is a single or double bond as necessary to give every atom its normal valence;

$R^p$ is independently H, hydroxy, —$C_{1-6}$alkyl, halo, —$C_{1-4}$haloalkyl, —$C_{1-4}$alkoxy, —NH—$C_{1-4}$alkyl, —N($C_{1-4}$alkyl)$_2$, cyano, —$C_{2-3}$alkenyl, —$C_{2-3}$alkynyl, —$C_{3-14}$cycloalkyl, —$C_{2-14}$heterocycloalkyl, aryl, or heteroaryl;

$R^1$ is independently H, hydroxy, —$C_{1-6}$alkyl, —$C_{1-6}$haloalkyl, —$C_{1-6}$alkoxy, —NH—$C_{1-6}$alkyl, —N($C_{1-4}$alkyl)$_2$, cyano, or halo;

$R^2$ is halo, —$C_{1-6}$alkyl, —$C_{1-6}$haloalkyl, —$OR^{2a}$, —$N(R^{2a})_2$, —$C_{2-6}$alkenyl, —$C_{2-6}$alkynyl, —$C_{0-3}$alkylene-$C_{3-14}$cycloalkyl, —$C_{0-3}$alkylene-$C_{2-14}$heterocycloalkyl, aryl, heteroaryl, —$C_{0-3}$alkylene-$C_{6-14}$aryl, or —$C_{0-3}$alkylene-$C_{2-14}$heteroaryl, and each $R^{2a}$ is independently H, —$C_{1-6}$alkyl, —$C_{1-6}$haloalkyl, —$C_{3-14}$cycloalkyl, —$C_{2-14}$heterocycloalkyl, —$C_{2-6}$alkenyl, —$C_{2-6}$alkynyl, aryl, or heteroaryl, or two $R^{2a}$ substituents, together with the nitrogen atom to which they are attached, form a 3-7-membered ring;

$R^3$ is halo, —$C_{1-6}$alkyl, —$C_{1-6}$haloalkyl, —$C_{1-6}$alkoxy, $C_{3-6}$cycloalkyl, —$C_{2-14}$heterocycloalkyl, —$C_{2-6}$alkenyl, —$C_{2-6}$alkynyl, aryl, or heteroaryl;

$R^4$ is

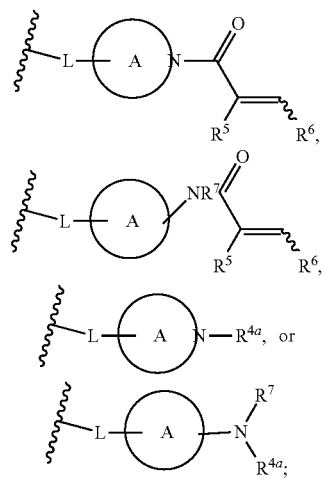

ring A is a monocyclic 4-7 membered ring or a bicyclic, bridged, fused, or spiro 6-11 membered ring;

L is a bond, —$C_{1-6}$alkylene, —O—$C_{0-6}$alkylene, —S—$C_{0-6}$alkylene, or —NH—$C_{0-6}$alkylene, and for —$C_{2-6}$alkylene, —O—$C_{2-6}$alkylene, —S—$C_{2-6}$alkylene, and NH—$C_{2-6}$ alkylene, one carbon atom of the alkylene group can optionally be replaced with O, S, or NH;

$R^{4a}$ is H, $C_{1-6}$alkyl, $C_{2-6}$alkynyl, $C_{1-6}$alkylene-O—$C_{1-4}$alkyl, $C_{1-6}$alkylene-OH, $C_{1-6}$haloalkyl, cycloalkyl, heterocycloalkyl, $C_{0-3}$alkylene-$C_{3-14}$cycloalkyl, $C_{0-3}$alkylene-$C_{2-14}$heterocycloalkyl, aryl, heteroaryl, $C_{0-3}$alkylene-$C_{6-14}$aryl, or selected from

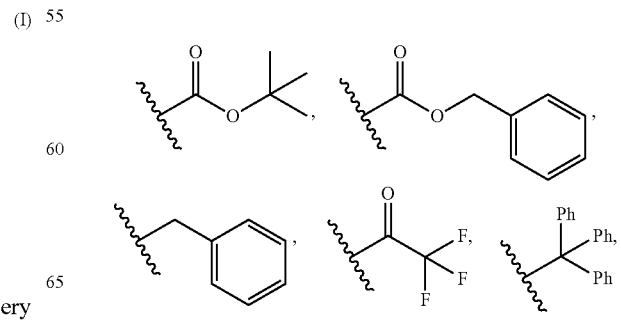

-continued

[Chemical structures shown]

$R^5$ and $R^6$ are each independently H, halo, —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —$C_{0-3}$alkylene-C(O)OH, —$C_{0-3}$alkylene-C(O)O$C_{1-4}$alkyl, —$C_{1-6}$ alkylene-O-aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, —$C_{0-3}$alkylene-$C_{2-14}$heteroaryl, or cyano, or $R^5$ and $R^6$, together with the atoms to which they are attached, form a 4-6 membered ring;

$R^7$ is H or $C_{1-6}$alkyl, or $R^7$ and $R^5$, together with the atoms to which they are attached, form a 4-6 membered ring;

$R^8$ is —$C_{1-6}$alkyl, —$C_{0-3}$alkylene-$C_{6-14}$aryl, —$C_{0-3}$alkylene-$C_{3-14}$heteroaryl, —$C_{0-3}$ alkylene-$C_{3-14}$cycloalkyl, —$C_{0-3}$alkylene-$C_{2-14}$heterocycloalkyl, —$C_{1-6}$alkoxy, —O—$C_{0-3}$ alkylene-$C_{6-14}$aryl, —O—$C_{0-3}$alkylene-$C_{3-14}$heteroaryl, —O—$C_{0-3}$ alkylene-$C_{3-14}$cycloalkyl, —O—$C_{0-3}$ alkylene-$C_{2-14}$heterocycloalkyl, —NH—$C_{1-8}$alkyl, —N($C_{1-8}$alkyl)$_2$, —NH—$C_{0-3}$alkylene-$C_{6-14}$aryl, —NH—$C_{0-3}$alkylene-$C_{2-14}$heteroaryl, —NH—$C_{0-3}$alkylene-$C_{3-14}$cycloalkyl, —NH—$C_{0-3}$ alkylene-$C_{2-14}$heterocycloalkyl, halo, cyano, or $C_{1-6}$alkylene-amine;

wherein the heteroaryl, spiroheterocycloalkyl and heterocycloalkyl groups of any of the $R^p$, $R^2$, $R^{2a}$, $R^3$, $R^4$, $R^{4a}$, $R^5$, $R^6$, $R^7$, and $R^8$ substituents have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or SO$_2$;

wherein the —$C_{1-6}$alkyl, —$C_{2-6}$alkenyl, —$C_{2-6}$alkynyl and the —O$C_{1-6}$alkyl of any of the $R^p$, $R^1$, $R^2$, $R^{2a}$, $R^3$, $R^4$, $R^{4a}$, L, $R^5$, $R^6$, $R^7$, and $R^8$ substituents is unsubstituted or substituted by 1, 2 or 3 $R^9$ substituents independently selected from OH, —O$C_{1-6}$alkyl, —$C_{1-6}$alkyl-O—$C_{1-6}$alkyl, halo, —O-halo$C_{1-6}$alkyl, —CN, —NR$^a$R$^b$. —(NR$^a$R$^b$R$^c$)$_n$, —OSO$_2$R$^a$, —SO$_2$R$^a$, —(CH$_2$CH$_2$O)$_n$CH$_3$, —(=O), —C(=O), —C(=O)R$^a$, —OC(=O)R$^a$, —C(=O)OR$^a$, —C(=O)NR$^a$R$^b$, —SiR$^a$R$^b$R$^c$, —SiR$^a$R$^b$R$^c$, —O-(3- to 10-membered heterocycloakyl), a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or SO$_2$;

wherein the aryl, heteroaryl, cycloalkyl, and heterocycloalkyl group of any of the $R^p$, $R^1$, $R^2$, $R^{2a}$, $R^3$, $R^4$, $R^{4a}$, $R^5$, $R^6$, $R^7$, $R^8$ and $R^9$ substituents can be unsubstituted or substituted with 1, 2, 3 or 4 $R^{10}$ substituents independently selected from OH, halo, —NR$^c$R$^d$, —$C_{1-6}$alkyl, —O$C_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups of $R^{10}$ have 1, 2, 3 or 4 heteroatoms independently selected from O, N or S, wherein the cycloalkyl, spirocycloalkyl, and spiroheterocycloalkyl groups of $R^{10}$ or the heterocycloalkyl group of $R^{10}$ may include a C=O group, and further wherein the spiroheterocycloalkyl and heterocycloalkyl groups may include a S=O or SO$_2$;

wherein each R$^a$, R$^b$, R$^c$ and R$^d$ is independently hydrogen, OH, —$C_{1-6}$alkyl, —(CH$_2$CH$_2$O)$_n$CH$_3$, —NR$^{11}$R$^{11}$, —$C_{1-6}$alkyl-NR$^{11}$R$^{11}$, phenyl, —$C_{1-6}$alkyl-C(=O)OH, —$C_{1-6}$alkyl-C(=O)—O—$C_{1-6}$alkyl, —$C_{1-6}$alkyl-3- to 12-membered cycloalkyl, —$C_{1-6}$alkyl-3- to 12-membered heterocycloalkyl, —$C_{1-6}$alkyl-6- to 12-membered heteroaryl, a 6- to 12-membered aryl or heteroaryl, a 3- to 12-membered monocyclic or bicyclic cycloalkyl, or a 3- to 12-membered monocyclic or bicyclic heterocycloalkyl group, wherein the heteroaryl group, heterocycloalkyl group of R$^a$, R$^b$, R$^c$, and R$^d$ or the heterocycloalkyl group of the —$C_{1-6}$alkyl-heterocycloalkyl group of R$^a$, R$^b$, R$^c$, and R$^d$ has from 1, 2, 3, or 4 heteroatoms independently selected from O, N or S, wherein the cycloalkyl and heterocycloalkyl groups of R$^a$, R$^b$, R$^c$, and R$^d$ and the heterocycloalkyl group of the —$C_{1-6}$alkyl-heterocycloalkyl groups of R$^a$, R$^b$, R$^c$, and R$^d$ may include a double bond, and further wherein the cycloalkyl and heterocycloalkyl groups of R$^a$, R$^b$, R$^c$, and R$^d$ and the heterocycloalkyl group of the —$C_{1-6}$alkyl-heterocycloalkyl groups of R$^a$, R$^b$, R$^c$, and R$^d$ may contain a C=O group; and the alkyl, aryl, heteroaryl, cycloalkyl, heterocycloalkyl groups of R$^a$, R$^b$, R$^c$, and R$^d$ or the heterocycloalkyl groups of the —$C_{1-6}$alkyl-heterocycloalkyl groups of R$^a$, R$^b$, R$^c$, and R$^d$ can be unsubstituted or substituted with from 1, 2, 3, or 4 R$^{12}$ substituents, wherein each R$^{12}$ is independently selected from H, OH, halo, —$C_{1-6}$alkyl, N(CH$_3$)$_2$, —$C_{1-6}$haloalkyl, C(=O)CH$_3$, —C(=O)OCH$_3$, or —$C_{1-6}$alkyl-O—$C_{1-6}$alkyl; or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Another aspect of the present invention provides a having a structure of formula (Ia)

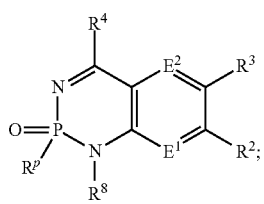

(Ia)

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

One aspect of the present invention provides various compounds, stereoisomers, atropisomers, pharmaceutically acceptable salts, pharmaceutically acceptable salts of the stereoisomers, and pharmaceutically acceptable salts of the atropisomers as described in the embodiments set forth below.

Another aspect of the present invention provides a pharmaceutical composition that includes the compound of any of the embodiments or the pharmaceutically acceptable salt thereof, and a pharmaceutically acceptable carrier or diluent.

Another aspect of the present invention provides a method of treating cancer. Such methods include: administering to a patient in need thereof a therapeutically effective amount of the compound of any of the embodiments or a pharmaceutically acceptable salt thereof. In some such methods, the cancer is a hematologic malignancy. In some such methods, the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia. In some other such methods, the cancer is multiple myeloma. In some other such methods, the cancer is acute myelogenous leukemia. In some other such methods, the cancer is non-Hodgkin's lymphoma. In another aspect, the method further includes administering to a patient in need thereof a therapeutically effective amount of an additional pharmaceutically active compound. For example, in some such methods the additional pharmaceutically active compound is carfilzomib. In others, the additional pharmaceutically active compound is venetoclax. In still other such methods, the additional pharmaceutically active compound is cytarabine. In still other such methods, the additional pharmaceutically active compound is daratumumab. In still other such methods, the additional pharmaceutically active compound is an MCl-1 inhibitor. In still other such methods, the MCl-1 inhibitor is AMG-176. In still other such methods, the additional pharmaceutically active compound is an IMiD.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the Claims.

DETAILED DESCRIPTION

| | |
|---|---|
| AcOH | acetic acid |
| aq or aq | aqueous |
| BOC or Boc | tert-butyloxycarbonyl |
| DCM | dichloromethane |
| DIPEA or Hunig's Base | N,N-diisopropylethylamine |
| DMAP | 4-dimethylaminopyridine |

-continued

| | |
|---|---|
| DME | 1,2-dimethoxyethane |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | equivalent |
| ESI or ES | electrospray ionization |
| Et | ethyl |
| Et$_2$O | diethyl ether |
| EtOAc | ethyl acetate |
| g | gram(s) |
| h or hr | hour(s) |
| HPLC | high pressure liquid chromatography |
| iPr | isopropyl |
| iPr$_2$NEt or DIPEA | N-ethyl diisopropylamine (Hunig's base) |
| KHMDS | potassium hexamethyldisilazide |
| KOAc | potassium acetate |
| LC MS, LCMS, LC-MS or LC/MS | liquid chromatography mass spectroscopy |
| LHMDS or LiHMDS | lithium hexamethyldisilazide |
| m/z | mass divided by charge |
| Me | methyl |
| MeCN | acetonitrile |
| MeOH | methanol |
| mg | milligrams |
| min | minutes |
| mL | milliliters |
| MS | mass spectra |
| NaHMDS | sodium hexamethyldisilazide |
| NBS | N-bromosuccinimide |
| n-BuLi | n-butyllithium |
| NCS | N-chlorosuccinimide |
| NMR | nuclear magnetic resonance |
| Pd$_2$(dba)$_3$ | tris(dibenzylidencacetone)dipalladium(0) |
| Pd(dppf)Cl$_2$•DCM, Pd(dppf)Cl$_2$ | [1,1'-bis(diphenylphosphino)ferrocene] dichloropalladium(II), complex with dichloromethane |
| Pd(PPh$_3$)$_4$ | tetrakis(triphenylphosphine)palladium(0) |
| Ph | phenyl |
| PR or PG or Prot. group | protecting group |
| rbf | round-bottom flask |
| RP-HPLC | reverse phase high pressure liquid chromatography |
| RT or rt or r.t. | room temperature |
| sat. or sat'd | saturated |
| SFC | supercritical fluid chromatography |
| TBAF | tetra-n-butylammonium fluoride |
| TEA or Et$_3$N | triethylamine |
| TFA | trifluoroacetic acid |
| THF | tetrahydrofuran |
| UV | ultraviolet |

Definitions

Abbreviations: The Following Abbreviations May be Used Herein

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched C1-C$_8$ hydrocarbon groups, including but not limited to, methyl, ethyl, n-propyl, i-propyl, n-butyl, sec-butyl, t-butyl, n-pentyl, 2-methylbutyl, 3-methylbutyl, 2,2- dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term $C_{m-n}$ means the alkyl group has "m" to "n" carbon atoms. The term "alkylene" refers to an alkyl group having a substituent. An alkyl (e.g., methyl), or alkylene (e.g., —CH$_2$—), group can be substituted with one or more, and typically one to three, of independently selected, for example, halo, trifluoromethyl, trifluoromethoxy, hydroxy, alkoxy, nitro, cyano, alkylamino, $C_{1-6}$alkyl, $C_{2-6}$alkenyl, $C_{2-6}$alkynyl, —NC, amino, —CO$_2$H, —CO$_2$C$_1$-C$_6$alkyl, —OCOC$_1$-C$_6$alkyl, $C_3$-C$_{10}$ cycloalkyl, $C_3$-C$_{10}$ heterocycloalkyl, $C_5$-C$_{10}$aryl, and $C_5$-C$_{10}$ heteroaryl. The term "haloalkyl" specifically refers to an alkyl group wherein at least one, e.g., one to six, or all of the hydrogens of the alkyl group are substituted with halo atoms.

The terms "alkenyl" and "alkynyl" indicate an alkyl group that further includes a double bond or a triple bond, respectively.

As used herein, the term "halo" refers to fluoro, chloro, bromo, and iodo. The term "alkoxy" is defined as —OR, wherein R is alkyl.

As used herein, the term "amino" or "amine" interchangeably refers to a —NR$_2$ group, wherein each R is, e.g., H or a substituent. In some embodiments, the amino group is further substituted to form an ammonium ion, e.g., NR$_3^+$. Ammonium moieties are specifically included in the definition of "amino" or "amine." Substituents can be, for example, an alkyl, alkoxy, cycloalkyl, heterocycloalkyl, amide, or carboxylate. An R group may be further substituted, for example, with one or more, e.g., one to four, groups selected from halo, cyano, alkenyl, alkynyl, alkyl, cycloalkyl, heterocycloalkyl, aryl, heteroaryl, urea, carbonyl, carboxylate, amine, and amide. An "amide" or "amido" group interchangeably refers to a group similar to an amine or amino group but further including a C(O), e.g., —C(O)NR$_2$. Some contemplated amino or amido groups (some with optional alkylene groups, e.g., alkylene-amino, or alkylene-amido) include CH$_2$NH$_2$, CH(CH$_3$)NH$_2$, CH(CH$_3$)$_2$NH$_2$, CH$_2$CH$_2$NH$_2$, CH$_2$CH$_2$N(CH$_3$)$_2$, CH$_2$NHCH$_3$, C(O)NHCH$_3$, C(O)N(CH$_3$)$_2$, CH$_2$C(O)NHphenyl, CH$_2$NHC(O)CH$_3$, CH$_2$NHCH$_2$CH$_2$OH, CH$_2$NHCH$_2$CO$_2$H, CH$_2$NH(CH$_3$)CH$_2$CO$_2$CH$_3$, CH$_2$NHCH$_2$CH$_2$OCH$_3$, CH$_2$NH(CH$_3$)CH$_2$CH$_2$OCH$_3$, CH$_2$NH(CH$_3$)CH$_2$C(O)N(CH$_3$)$_2$, CH$_2$NH(CH$_3$)CH$_2$C(O)NHCH$_3$, CH$_2$CH$_2$CCH, CH$_2$NMe$_2$, CH$_2$NH(CH$_3$)CH$_2$CH$_2$OH, CH$_2$NH(CH$_3$)CH$_2$CH$_2$F, CH$_2$N$^+$(CH$_3$)$_3$, CH$_2$NHCH$_2$CHF$_2$, CH$_2$NHCH$_2$CH$_3$,

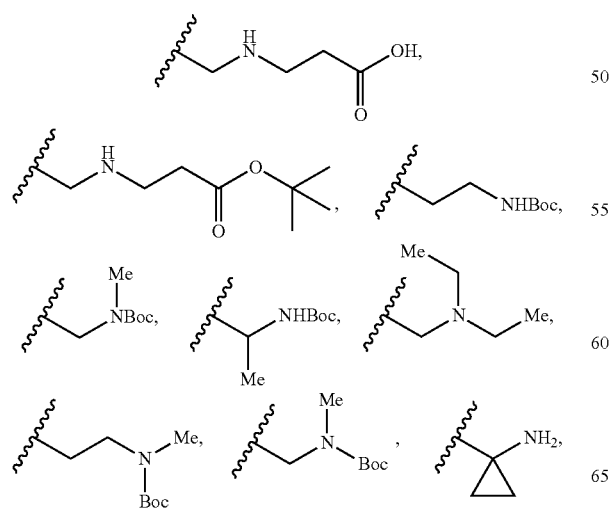

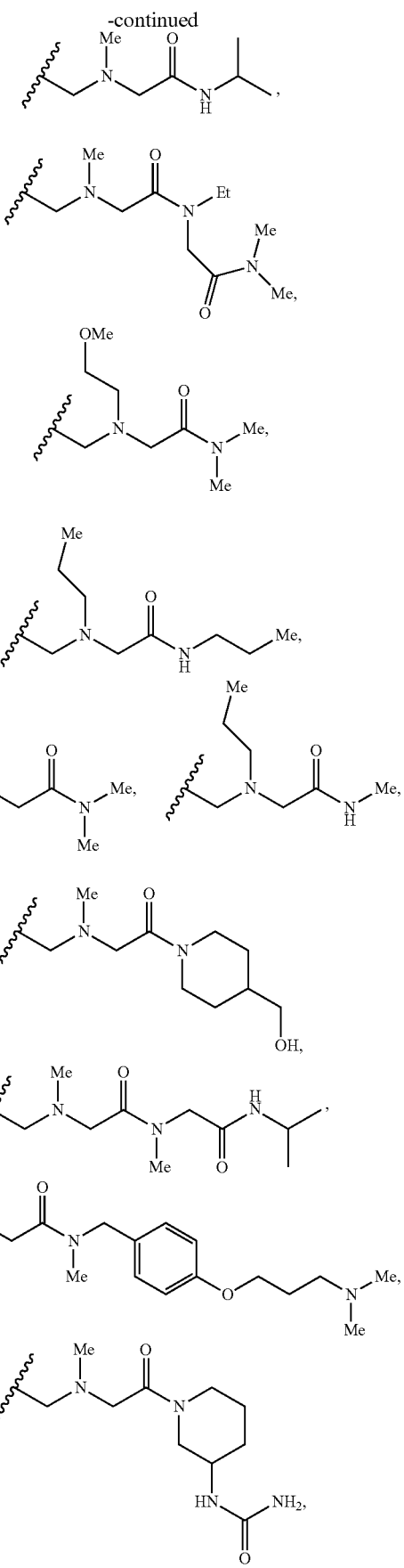

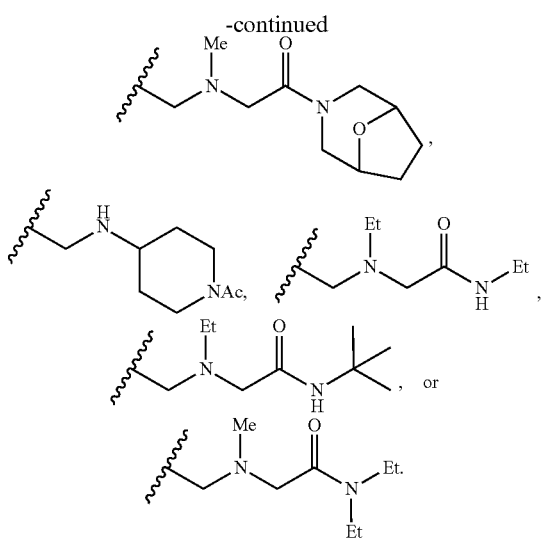

As used herein, the term "aryl" refers to a $C_{6-14}$ monocyclic or polycyclic aromatic group, preferably a $C_{6-10}$ monocyclic or bicyclic aromatic group, or $C_{10-14}$ polycyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to $C_{10-14}$ bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, $C_{1-6}$alkyl, $C_{2-6}$alkenyl, $C_{2-6}$alkynyl, —$CF_3$, —$OCF_3$, —$NO_2$, —CN, —NC, —OH, alkoxy, amino, —$CO_2H$, —$CO_2C_1$-$C_6$alkyl, —$OCOC_1$-$C_6$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term "cycloalkyl" refers to a monocyclic or polycyclic non-aromatic carbocyclic ring, where the polycyclic ring can be fused, bridged, or spiro. The carbocyclic ring can have 3 to 10 carbon ring atoms. Contemplated carbocyclic rings include, but are not limited to, cyclopropyl, cyclobutyl, cyclopentyl, cyclohexyl, cycloheptyl, cyclooctyl, and cyclononyl.

As used herein, the term "heterocycloalkyl" means a monocyclic or polycyclic (e.g., bicyclic), saturated or partially unsaturated, ring system containing 3 or more (e.g., 3 to 12, 4 to 10, 4 to 8, or 5 to 7) total atoms, of which one to five (e.g., 1, 2, 3, 4, or 5) of the atoms are independently selected from nitrogen, oxygen, and sulfur. Nonlimiting examples of heterocycloalkyl groups include azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, and diazacycloheptyl.

Unless otherwise indicated, a cycloalkyl or heterocycloalkyl group can be unsubstituted or substituted with one or more, and in particular one to four, groups. Some contemplated substituents include halo, $C_{1-6}$alkyl, $C_{2-6}$alkenyl, $C_{2-6}$alkynyl, —$OCF_3$, —$NO_2$, —CN, —NC, —OH, alkoxy, amino, —$CO_2H$, —$CO_2C_1$-$C_6$alkyl, —$OCOC_1$-$C_8$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term "heteroaryl" refers to a monocyclic or polycyclic ring system (for example, bicyclic) containing one to three aromatic rings and containing one to four (e.g., 1, 2, 3, or 4) heteroatoms selected from nitrogen, oxygen, and sulfur in an aromatic ring. In certain embodiments, the heteroaryl group has from 5 to 20, from 5 to 15, from 5 to 10 ring, or from 5 to 7 atoms. Heteroaryl also refers to $C_{10-14}$ bicyclic and tricyclic rings, where one ring is aromatic and the others are saturated, partially unsaturated, or aromatic. Examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four or one or two, substituents. Contemplated substituents include halo, $C_{1-6}$alkyl, $C_{2-6}$alkenyl, $C_{2-6}$alkynyl, —$OCF_3$, —$NO_2$, —CN, —NC, —OH, alkoxy, amino, —$CO_2H$, —$CO_2C_1$-$C_6$alkyl, —$OCOC_1$-$C_6$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term Boc refers to the structure

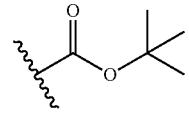

As used herein, the term Cbz refers to the structure

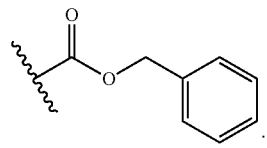 [SMILES: *C(=O)OCc1ccccc1]

As used herein, the term Bn refers to the structure

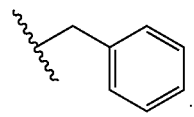

As used herein, the term trifluoroacetamide refers to the structure

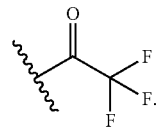

As used herein, the term trityl refers to the structure

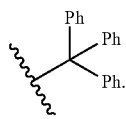

As used herein, the term tosyl refers to the structure

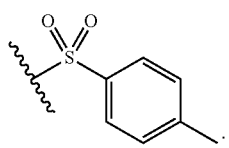 [SMILES: *S(=O)(=O)c1ccc(C)cc1]

As used herein, the term Troc refers to the structure

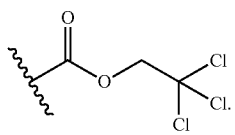 [SMILES: *C(=O)OCC(Cl)(Cl)Cl]

As used herein, the term Teoc refers to the structure

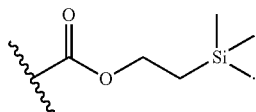

As used herein, the term Alloc refers to the structure

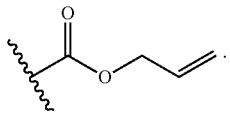 [SMILES: *C(=O)OCC=C ; "."]

As used herein, the term Fmoc refers to the structure

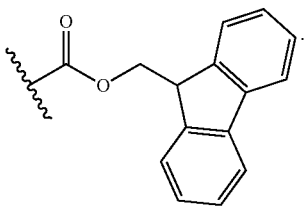 [SMILES: *C(=O)OCC1c2ccccc2-c2ccccc21 ; "."]

Compounds of the Disclosure

The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labeled compounds of the disclosure, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Isotopically-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

Certain of the compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a nonspecific mixture of each. Where the rotational barrier about the single bond is high enough, and interconversion between conformations is slow enough, separation and isolation of the isomeric species may be permitted. For example, groups such as, but not limited to, the following $R^{8}$ groups,

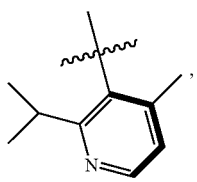 , and 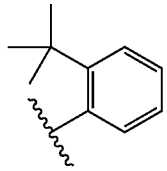

may exhibit restricted rotation.

$E^1$ and $E^2$ are each independently N or $CR^1$;

$\text{---}$ is a single or double bond as necessary to give every atom its normal valence;

$R^p$ is independently H, hydroxy, —$C_{1-6}$alkyl, halo, —$C_{1-4}$haloalkyl, —$C_{1-4}$alkoxy, —NH—$C_{1-4}$alkyl, —N($C_{1-4}$alkyl)$_2$, cyano, —$C_{2-3}$alkenyl, —$C_{2-3}$alkynyl, —$C_{3-14}$cycloalkyl, —$C_{2-14}$heterocycloalkyl, aryl, or heteroaryl;

$R^1$ is independently H, hydroxy, —$C_{1-6}$alkyl, —$C_{1-6}$haloalkyl, —$C_{1-6}$alkoxy, —NH—$C_{1-4}$alkyl, —N($C_{1-4}$alkyl)$_2$, cyano, or halo;

$R^2$ is halo, —$C_{1-6}$alkyl, —$C_{1-6}$haloalkyl, —$OR^{2a}$, —$N(R^{2a})_2$, —$C_{2-6}$alkenyl, —$C_{2-6}$alkynyl, —$C_{0-3}$alkylene-$C_{3-14}$cycloalkyl, —$C_{0-3}$alkylene-$C_{2-14}$heterocycloalkyl, aryl, heteroaryl, —$C_{0-3}$alkylene-$C_{6-14}$aryl, or —$C_{0-3}$alkylene-$C_{2-14}$heteroaryl, and each $R^{2a}$ is independently H, —$C_{1-6}$alkyl, —$C_{1-6}$haloalkyl, —$C_{3-14}$cycloalkyl, —$C_{2-14}$heterocycloalkyl, —$C_{2-6}$alkenyl, —$C_{2-6}$alkynyl, aryl, or heteroaryl, or two $R^{2a}$ substituents, together with the nitrogen atom to which they are attached, form a 3-7-membered ring;

$R^3$ is halo, —$C_{1-6}$alkyl, —$C_{1-6}$haloalkyl, —$C_{1-6}$alkoxy, $C_{3-6}$cycloalkyl, —$C_{2-14}$heterocycloalkyl, —$C_{2-6}$alkenyl, —$C_{2-6}$alkynyl, aryl, or heteroaryl;

$R^4$ is

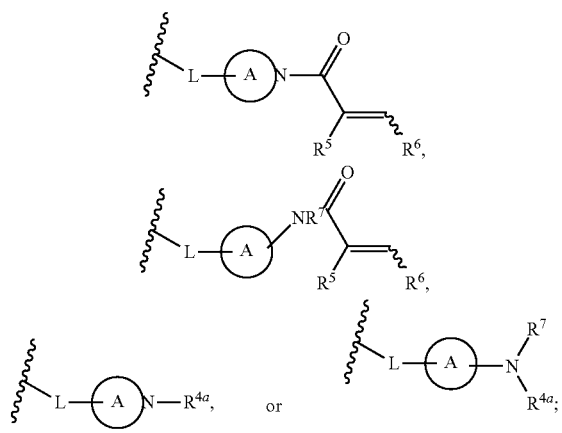

ring A is a monocyclic 4-7 membered ring or a bicyclic, bridged, fused, or spiro 6-11 membered ring;

L is a bond, —$C_{1-6}$alkylene, —O—$C_{0-6}$alkylene, —S—$C_{0-6}$alkylene, or —NH—$C_{0-6}$alkylene, and for —$C_{2-6}$alkylene, —O—$C_{2-6}$alkylene, —S—$C_{2-6}$alkylene, and NH—$C_{2-6}$ alkylene, one carbon atom of the alkylene group can optionally be replaced with O, S, or NH;

$R^{4a}$ is H, $C_{1-6}$alkyl, $C_{2-6}$alkynyl, $C_{1-6}$alkylene-O—$C_{1-4}$alkyl, $C_{1-6}$alkylene-OH, $C_{1-6}$ haloalkyl, cycloalkyl, heterocycloalkyl, $C_{0-3}$alkylene-$C_{3-14}$cycloalkyl, $C_{0-3}$alkylene-$C_{2-14}$heterocycloalkyl, aryl, heteroaryl, $C_{0-3}$alkylene-$C_{6-14}$aryl, or selected from

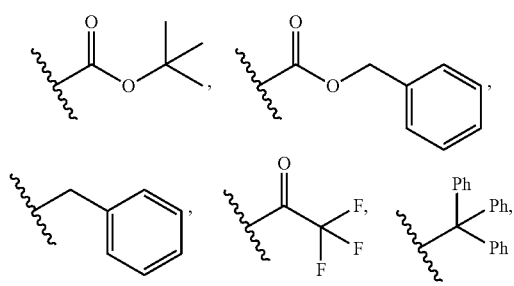

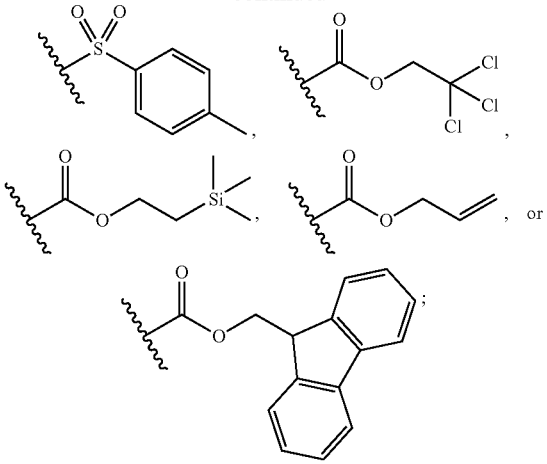

$R^5$ and $R^6$ are each independently H, halo, —$C_{1-6}$alkyl, —$C_{2-6}$alkynyl, —$C_{1-6}$alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —$C_{0-3}$alkylene-C(O)OH, —$C_{0-3}$alkylene-C(O)O$C_{1-4}$alkyl, —$C_{1-6}$ alkylene-O-aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, —$C_{0-3}$alkylene-$C_{2-14}$heteroaryl, or cyano, or $R^5$ and $R^6$, together with the atoms to which they are attached, form a 4-6 membered ring;

$R^7$ is H or $C_{1-6}$alkyl, or $R^7$ and $R^5$, together with the atoms to which they are attached, form a 4-6 membered ring;

$R^8$ is —$C_{1-6}$alkyl, —$C_{0-3}$alkylene-$C_{6-14}$aryl, —$C_{0-3}$alkylene-$C_{3-14}$heteroaryl, —$C_{0-3}$ alkylene-$C_{3-14}$cycloalkyl, —$C_{0-3}$alkylene-$C_{2-14}$heterocycloalkyl, —$C_{1-6}$alkoxy, —O—$C_{0-3}$ alkylene-$C_{6-14}$aryl, —O—$C_{0-3}$alkylene-$C_{3-14}$heteroaryl, —O—$C_{0-3}$ alkylene-$C_{3-14}$cycloalkyl, —O—$C_{0-3}$ alkylene-$C_{2-14}$heterocycloalkyl, —NH—$C_{1-8}$alkyl, —N($C_{1-8}$alkyl)$_2$, —NH—$C_{0-3}$alkylene-$C_{6-14}$aryl, —NH—$C_{0-3}$alkylene-$C_{2-14}$heteroaryl, —NH—$C_{0-3}$alkylene-$C_{3-14}$cycloalkyl, —NH—$C_{0-3}$ alkylene-$C_{2-14}$heterocycloalkyl, halo, cyano, or $C_{1-6}$alkylene-amine;

wherein the heteroaryl, spiroheterocycloalkyl and heterocycloalkyl groups of any of the $R^p$, $R^2$, $R^{2a}$, $R^3$, $R^4$, $R^{4a}$, $R^5$, $R^6$, $R^7$, and $R^8$ substituents have 1, 2, 3 or 4 heteroatoms independently selected from O, N or S, wherein the cycloalkyl, spirocycloalkyl, spiroheterocycloalkyl, and heterocycloalkyl groups may include a C═O group, and further wherein the spiroheterocycloalkyl, and heterocycloalkyl groups may include a S═O or $SO_2$;

wherein the —$C_{1-6}$alkyl, —$C_{2-6}$alkenyl, —$C_{2-6}$alkynyl and the —$OC_{1-6}$alkyl of any of the $R^p$, $R^1$, $R^2$, $R^{2a}$, $R^3$, $R^4$, $R^{4a}$, L, $R^5$, $R^6$, $R^7$, and $R^8$ substituents is unsubstituted or substituted by 1, 2 or 3 $R^9$ substituents independently selected from OH, —$OC_{1-6}$alkyl, —$C_{1-6}$alkyl-O—$C_{1-6}$alkyl, halo, —O-halo$C_{1-6}$alkyl, —CN, —$NR^aR^b$, —$(NR^aR^bR^c)_n$, —$OSO_2R^a$, —$SO_2R^a$, —$(CH_2CH_2O)_nCH_3$, —(═O), —C(═O), —C(═O)$R^a$, —OC(═O)$R^a$, —C(═O)$OR^a$, —C(═O)$NR^aR^b$, —O—$SiR^aR^bR^c$, —$SiR^aR^bR^c$, —O-(3- to 10-membered heterocycloakyl), a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or SO$_2$;

wherein the aryl, heteroaryl, cycloalkyl, and heterocycloalkyl group of any of the R$^p$, R$^1$, R$^2$, R$^{2a}$, R$^3$, R$^4$, R$^{4a}$, R$^5$, R$^6$, R$^7$, R$^8$ and R$^9$ substituents can be unsubstituted or substituted with 1, 2, 3 or 4 R$^{10}$ substituents independently selected from OH, halo, —NR$^c$R$^d$, —C$_{1-6}$alkyl, —OC$_{1-6}$alkyl, —C$_{1-6}$alkyl-OH, —C$_{1-6}$alkyl-O—C$_{1-6}$alkyl, C$_{1-6}$haloalkyl, —O-haloC$_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups of R$^{10}$ have 1, 2, 3 or 4 heteroatoms independently selected from O, N or S, wherein the cycloalkyl, spirocycloalkyl, and spiroheterocycloalkyl groups of R$^{10}$ or the heterocycloalkyl group of R$^{10}$ may include a C=O group, and further wherein the spiroheterocycloalkyl and heterocycloalkyl groups may include a S=O or SO$_2$;

wherein each R$^a$, R$^b$, R$^c$ and R$^d$ is independently hydrogen, OH, —C$_{1-6}$alkyl, —(CH$_2$CH$_2$O)$_n$CH$_3$, —NR$^{11}$R$^{11}$, —C$_{1-6}$alkyl-NR$^{11}$R$^{11}$, phenyl, —C$_{1-6}$alkyl-C(=O)OH, —C$_{1-6}$alkyl-C(=O)—O—C$_{1-6}$alkyl, —C$_{1-6}$alkyl-3- to 12-membered cycloalkyl, —C$_{1-6}$alkyl-3- to 12-membered heterocycloalkyl, —C$_{1-6}$alkyl-6- to 12-membered heteroaryl, a 6- to 12-membered aryl or heteroaryl, a 3- to 12-membered monocyclic or bicyclic cycloalkyl, or a 3- to 12-membered monocyclic or bicyclic heterocycloalkyl group, wherein the heteroaryl group, heterocycloalkyl group of R$^a$, R$^b$, R$^c$, and R$^d$ or the heterocycloalkyl group of the —C$_{1-6}$alkyl-heterocycloalkyl group of R$^a$, R$^b$, R$^c$, and R$^d$ has from 1, 2, 3, or 4 heteroatoms independently selected from O, N or S, wherein the cycloalkyl and heterocycloalkyl groups of R$^a$, R$^b$, R$^c$, and R$^d$ and the heterocycloalkyl group of the —C$_{1-6}$alkyl-heterocycloalkyl groups of R$^a$, R$^b$, R$^c$, and R$^d$ may include a double bond, and further wherein the cycloalkyl and heterocycloalkyl groups of R$^a$, R$^b$, R$^c$, and R$^d$ and the heterocycloalkyl group of the —C$_{1-6}$alkyl-heterocycloalkyl groups of R$^a$, R$^b$, R$^c$, and R$^d$ may contain a C=O group; and the alkyl, aryl, heteroaryl, cycloalkyl, heterocycloalkyl groups of R$^a$, R$^b$, R$^c$, and R$^d$ or the heterocycloalkyl groups of the —C$_{1-6}$alkyl-heterocycloalkyl groups of R$^a$, R$^b$, R$^c$, and R$^d$ can be unsubstituted or substituted with from 1, 2, 3, or 4 R$^{12}$ substituents, wherein each R$^{12}$ is independently selected from H, OH, halo, —C$_{1-6}$alkyl, N(CH$_3$)$_2$, —C$_{1-6}$haloalkyl, C(=O)CH$_3$, —C(=O)OCH$_3$, or —C$_{1-6}$alkyl-O—C$_{1-6}$alkyl;

a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

EMBODIMENTS

Embodiment 1

In a first embodiment, the invention provides a compound having a structure of formula (I)

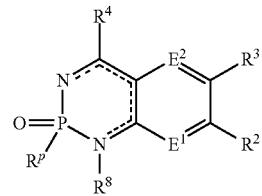

(I)

wherein

E$^1$ and E$^2$ are each independently N or CR$^1$;

--- is a single or double bond as necessary to give every atom its normal valence;

R$^p$ is independently H, hydroxy, —C$_{1-6}$alkyl, halo, —C$_{1-4}$haloalkyl, —C$_{1-4}$alkoxy, —NH—C$_{1-4}$alkyl, —N(C$_{1-4}$alkyl)$_2$, cyano, —C$_{2-3}$alkenyl, —C$_{2-3}$alkynyl, —C$_{3-14}$cycloalkyl, —C$_{2-14}$heterocycloalkyl, aryl, or heteroaryl;

R$^1$ is independently H, hydroxy, —C$_{1-6}$alkyl, —C$_{1-6}$haloalkyl, —C$_{1-6}$alkoxy, —NH—C$_{1-6}$alkyl, —N(C$_{1-4}$alkyl)$_2$, cyano, or halo;

R$^2$ is halo, —C$_{1-6}$alkyl, —C$_{1-6}$haloalkyl, —OR$^{2a}$, —N(R$^{2a}$)$_2$, —C$_{2-6}$alkenyl, —C$_{2-6}$alkynyl, —C$_{0-3}$alkylene-C$_{3-14}$cycloalkyl, —C$_{0-3}$alkylene-C$_{2-14}$heterocycloalkyl, aryl, heteroaryl, —C$_{0-3}$alkylene-C$_{6-14}$aryl, or —C$_{0-3}$alkylene-C$_{2-14}$heteroaryl, and each R$^{2a}$ is independently H, —C$_{1-6}$alkyl, —C$_{1-6}$haloalkyl, —C$_{3-14}$cycloalkyl, —C$_{2-14}$heterocycloalkyl, —C$_{2-6}$alkenyl, —C$_{2-6}$alkynyl, aryl, or heteroaryl, or two R$^{2a}$ substituents, together with the nitrogen atom to which they are attached, form a 3-7-membered ring;

R$^3$ is halo, —C$_{1-6}$alkyl, —C$_{1-6}$haloalkyl, —C$_{1-6}$alkoxy, C$_{3-6}$cycloalkyl, —C$_{2-14}$heterocycloalkyl, —C$_{2-6}$alkenyl, —C$_{2-6}$alkynyl, aryl, or heteroaryl;

R$^4$ is

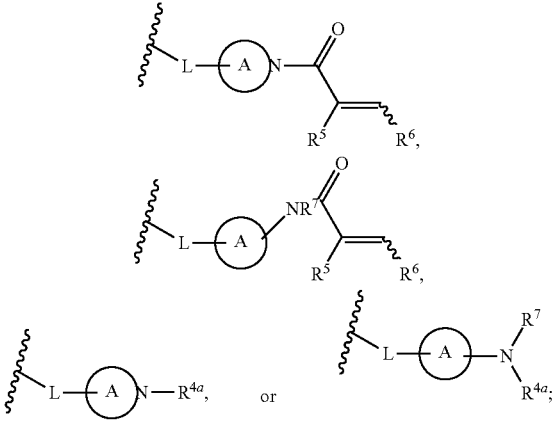

ring A is a monocyclic 4-7 membered ring or a bicyclic, bridged, fused, or spiro 6-11 membered ring;

L is a bond, —C$_{1-6}$alkylene, —O—C$_{0-6}$alkylene, —S—C$_{0-6}$alkylene, or —NH—C$_{0-6}$alkylene, and for —C$_{2-6}$alkylene, —O—C$_{2-6}$alkylene, —S—C$_{2-6}$alkylene, and NH—C$_{2-6}$ alkylene, one carbon atom of the alkylene group can optionally be replaced with O, S, or NH;

R$^{4a}$ is H, C$_{1-6}$alkyl, C$_{2-6}$alkynyl, C$_{1-6}$alkylene-O—C$_{1-4}$alkyl, C$_{1-6}$alkylene-OH, C$_{1-6}$haloalkyl, cycloalkyl, heterocycloalkyl, C$_{0-3}$alkylene-C$_{3-14}$cycloalkyl, C$_{0-3}$alkylene-$C_{2-14}$ heterocycloalkyl, aryl, heteroaryl, $C_{0-3}$alkylene-$C_{6-14}$aryl, or selected from

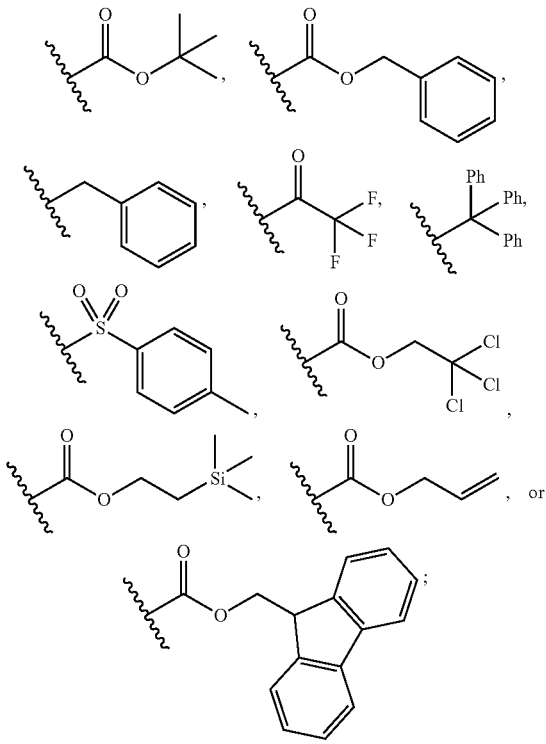

$R^5$ and $R^6$ are each independently H, halo, —$C_{1-6}$alkyl, —$C_{2-6}$alkynyl, —$C_{1-6}$alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —$C_{0-3}$alkylene-C(O)OH, —$C_{0-3}$alkylene-C(O)O$C_{1-4}$alkyl, —$C_{1-6}$ alkylene-O-aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, —$C_{0-3}$alkylene-$C_{2-14}$heteroaryl, or cyano, or $R^5$ and $R^6$, together with the atoms to which they are attached, form a 4-6 membered ring;

$R^7$ is H or $C_{1-6}$alkyl, or $R^7$ and $R^5$, together with the atoms to which they are attached, form a 4-6 membered ring;

$R^8$ is —$C_{1-6}$alkyl, —$C_{0-3}$alkylene-$C_{6-14}$aryl, —$C_{0-3}$alkylene-$C_{3-14}$heteroaryl, —$C_{0-3}$ alkylene-$C_{3-14}$cycloalkyl, —$C_{0-3}$alkylene-$C_{2-14}$heterocycloalkyl, —$C_{1-6}$alkoxy, —O—$C_{0-3}$ alkylene-$C_{6-14}$aryl, —O—$C_{0-3}$alkylene-$C_{3-14}$heteroaryl, —O—$C_{0-3}$ alkylene-$C_{3-14}$cycloalkyl, —O—$C_{0-3}$ alkylene-$C_{2-14}$heterocycloalkyl, —NH—$C_{1-8}$alkyl, —N($C_{1-8}$alkyl)$_2$, —NH—$C_{0-3}$alkylene-$C_{6-14}$aryl, —NH—$C_{0-3}$alkylene-$C_{2-4}$heteroaryl, —NH—$C_{0-3}$alkylene-$C_{3-14}$cycloalkyl, —NH—$C_{0-3}$ alkylene-$C_{2-14}$heterocycloalkyl, halo, cyano, or $C_{1-6}$alkyleneamine;

wherein the heteroaryl, spiroheterocycloalkyl and heterocycloalkyl groups of any of the $R^p$, $R^2$, $R^{2a}$, $R^3$, $R^4$, $R^{4a}$, $R^5$, $R^6$, $R^7$, and $R^8$ substituents have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or SO$_2$;

wherein the —$C_{1-6}$alkyl, —$C_{2-6}$alkenyl, —$C_{2-6}$alkynyl and the —O$C_{1-6}$alkyl of any of the $R^p$, $R^1$, $R^2$, $R^{2a}$, $R^3$, $R^4$, $R^{4a}$, L, $R^5$, $R^6$, $R^7$, and $R^8$ substituents is unsubstituted or substituted by 1, 2 or 3 $R^9$ substituents independently selected from OH, —O$C_{1-6}$alkyl, —$C_{1-6}$alkyl-O—$C_{1-6}$alkyl, halo, —O-halo$C_{1-6}$alkyl, —CN, —NR$^a$R$^b$, —(NR$^a$R$^b$R$^c$)$_n$, —OSO$_2$R$^a$, —SO$_2$R$^a$, —(CH$_2$CH$_2$O)$_n$CH$_3$, —(=O), —C(=O), —C(=O)R$^a$, —OC(=O)R$^a$, —C(=O)OR$^a$, —C(=O)NR$^a$R$^b$, —O—SiR$^a$R$^b$R$^c$, —SiR$^a$R$^b$R$^c$, —O-(3- to 10-membered heterocycloakyl), a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or SO$_2$;

wherein the aryl, heteroaryl, cycloalkyl, and heterocycloalkyl group of any of the $R^p$, $R^1$, $R^2$, $R^{2a}$, $R^3$, $R^4$, $R^{4a}$, $R^5$, $R^6$, $R^7$, $R^8$ and $R^9$ substituents can be unsubstituted or substituted with 1, 2, 3 or 4 $R^{10}$ substituents independently selected from OH, halo, —NR$^c$R$^d$, —$C_{1-6}$alkyl, —O$C_{1-6}$ alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups of $R^{10}$ have 1, 2, 3 or 4 heteroatoms independently selected from O, N or S, wherein the cycloalkyl, spirocycloalkyl, and spiroheterocycloalkyl groups of $R^{10}$ or the heterocycloalkyl group of $R^{10}$ may include a C=O group, and further wherein the spiroheterocycloalkyl and heterocycloalkyl groups may include a S=O or SO$_2$;

wherein each R$^a$, R$^b$, R$^c$ and R$^d$ is independently hydrogen, OH, —$C_{1-6}$alkyl, —(CH$_2$CH$_2$O)$_n$CH$_3$, —NR$^{11}$R$^{11}$, —$C_{1-6}$alkyl-NR$^{11}$R$^{11}$, phenyl, —$C_{1-6}$alkyl-C(=O)OH, —$C_{1-6}$alkyl-C(=O)—O—$C_{1-6}$alkyl, —$C_{1-6}$alkyl-3- to 12-membered cycloalkyl, —$C_{1-6}$alkyl-3- to 12-membered heterocycloalkyl, —$C_{1-6}$alkyl-6- to 12-membered heteroaryl, a 6- to 12-membered aryl or heteroaryl, a 3- to 12-membered monocyclic or bicyclic cycloalkyl, or a 3- to 12-membered monocyclic or bicyclic heterocycloalkyl group, wherein the heteroaryl group, heterocycloalkyl group of R$^a$, R$^b$, R$^c$, and R$^d$ or the heterocycloalkyl group of the —$C_{1-6}$alkyl-heterocycloalkyl group of R$^a$, R$^b$, R$^c$, and R$^d$ has from 1, 2, 3, or 4 heteroatoms independently selected from O, N or S, wherein the cycloalkyl and heterocycloalkyl groups of R$^a$, R$^b$, R$^c$, and R$^d$ and the heterocycloalkyl group of the —$C_{1-6}$alkyl-heterocycloalkyl groups of R$^a$, R$^b$, R$^c$, and R$^d$ may include a double bond, and further wherein the cycloalkyl and heterocycloalkyl groups of R$^a$, R$^b$, R$^c$, and R$^d$ and the heterocycloalkyl group of the —$C_{1-6}$alkyl-heterocycloalkyl groups of R$^a$, R$^b$, R$^c$, and R$^d$ may contain a C=O group; and the alkyl, aryl, heteroaryl, cycloalkyl, heterocycloalkyl groups of R$^a$, R$^b$, R$^c$, and R$^d$ or the heterocycloalkyl groups of the —$C_{1-6}$alkyl-heterocycloalkyl groups of R$^a$, R$^b$, R$^c$, and R$^d$ can be unsubstituted or substituted with from 1, 2, 3, or 4 $R^{12}$ substituents, wherein each $R^{12}$ is independently selected from H, OH, halo, —$C_{1-6}$alkyl, $N(CH_3)_2$, —$C_{1-6}$haloalkyl, $C(=O)CH_3$, —$C(=O)OCH_3$, or —$C_{1-6}$alkyl-O—$C_{1-6}$alkyl; or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 2

A compound of embodiment 1 having a structure of formula (Ia)

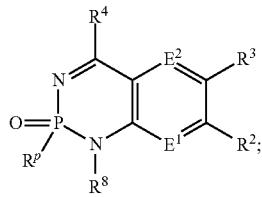

(Ia)

or
a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 3

The compound of any of one of embodiments 1 or 2 wherein $R^p$ is —$C_{1-6}$alkyl.

Embodiment 4

The compound of embodiment 3 wherein $R^p$ is —$CH_3$.

Embodiment 5

The compound of any of one of embodiments 1-4 wherein $R^1$ is H.

Embodiment 6

The compound of any of one of embodiments 1-5 wherein $R^2$ is an unsubstituted or substituted aryl.

Embodiment 7

The compound of embodiment 6 wherein $R^2$ is a substituted aryl.

Embodiment 8

The compound of embodiment 7 wherein $R^2$ is a fluorinated phenyl.

Embodiment 9

The compound of any of one of embodiments 1-8 wherein $R^3$ is halo.

Embodiment 10

The compound of embodiment 9 wherein $R^3$ is Cl.

Embodiment 11

The compound of any of one of embodiments 1-10 wherein $R^4$ is

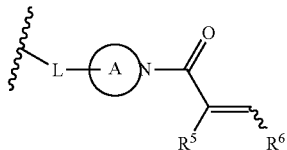

Embodiment 12

The compound of embodiment 11 wherein L is a bond.

Embodiment 13

The compound of embodiment 11 wherein ring A is a monocyclic 4-7 membered ring.

Embodiment 14

The compound of embodiment 13 wherein A is an unsubstituted or substituted heterocycle.

Embodiment 15

The compound of any one of embodiments 1 to 14, wherein R4 is selected from the group consisting of

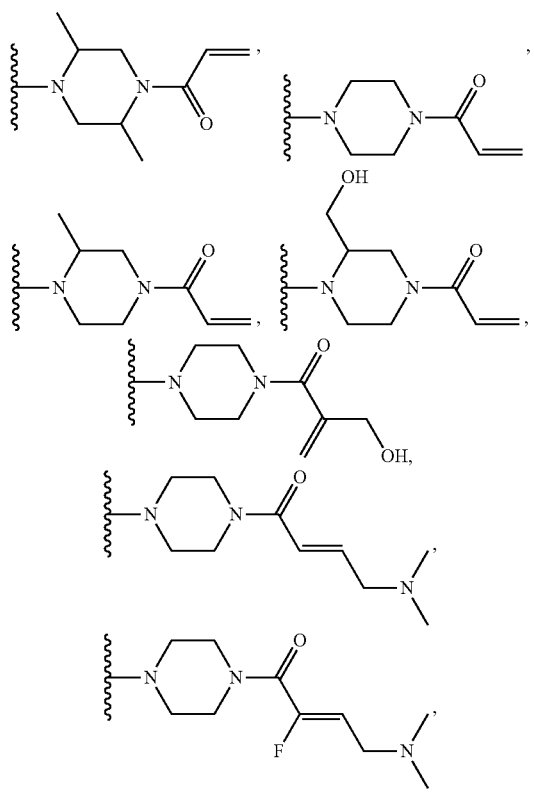

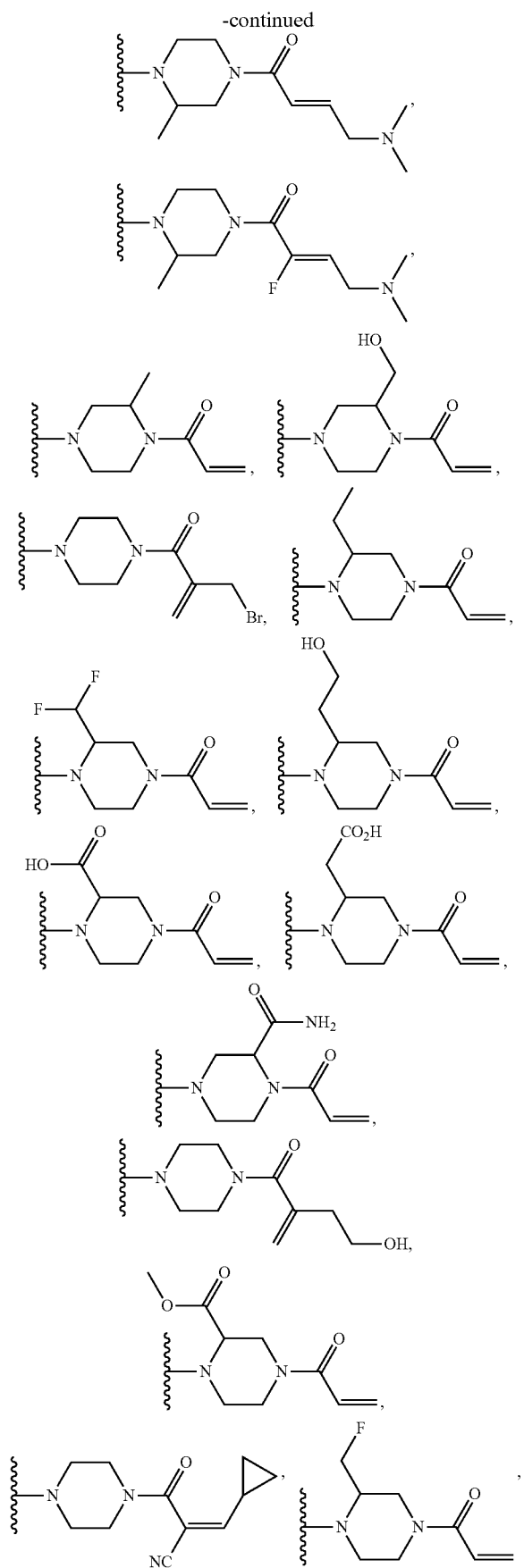
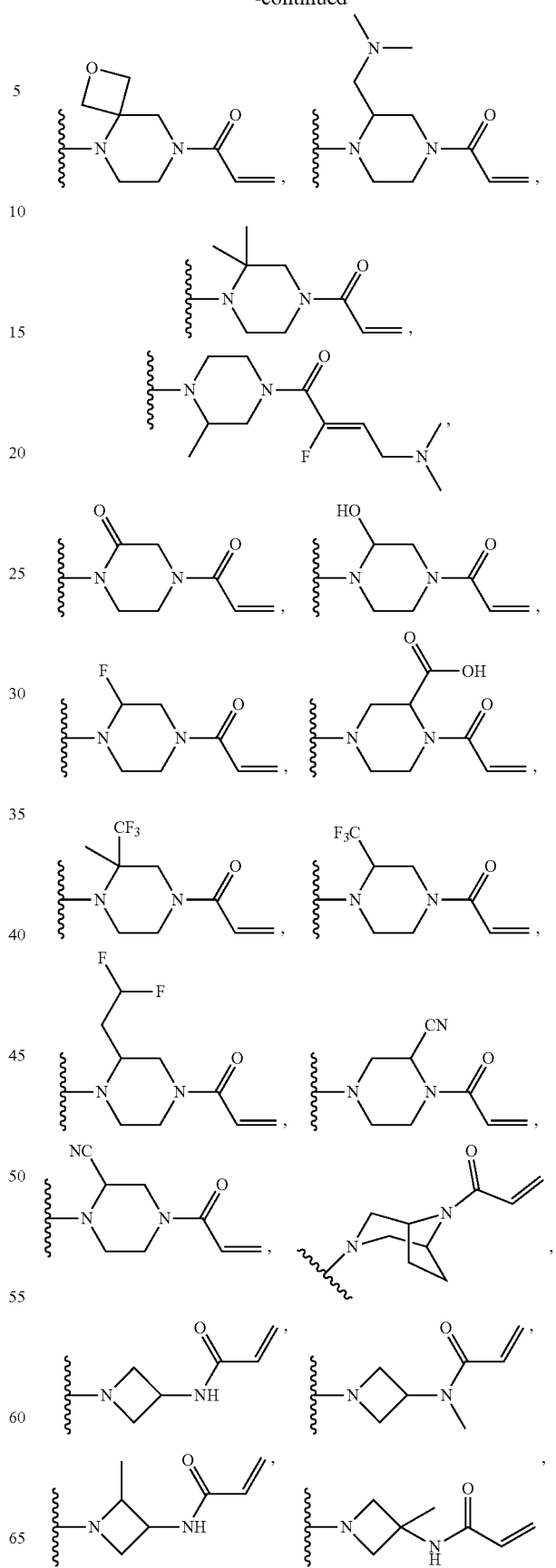

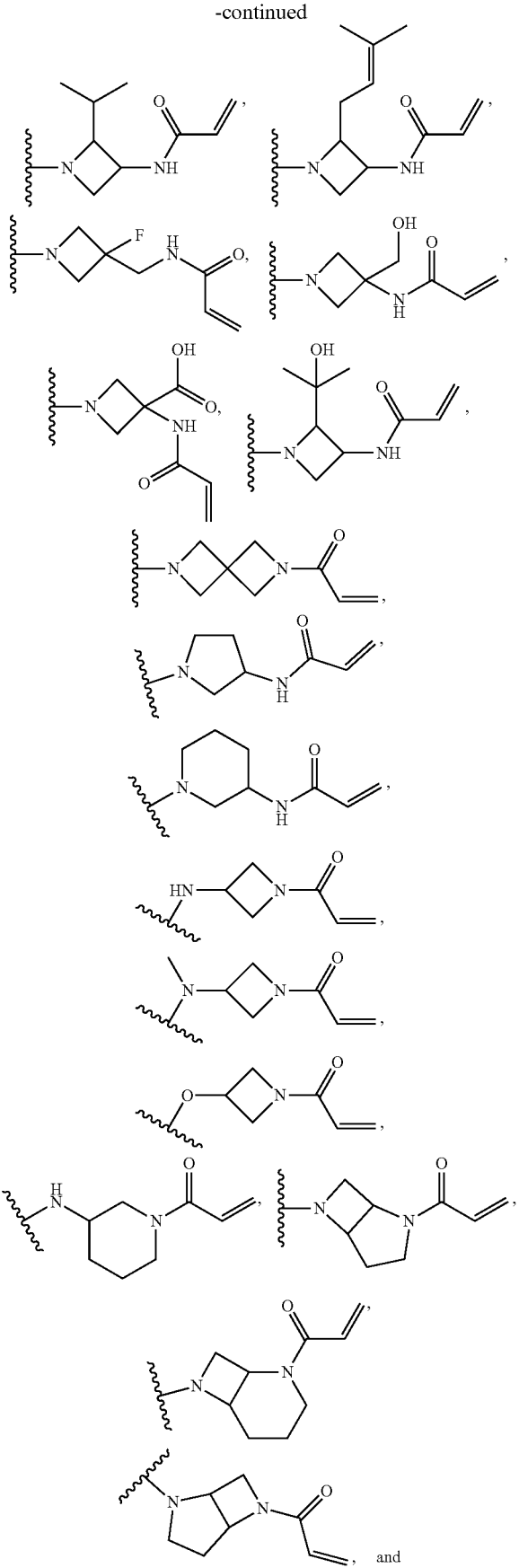

and

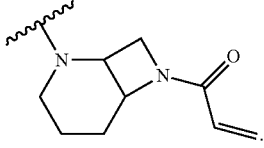

Embodiment 16

The compound of embodiment 15, wherein $R^4$ is

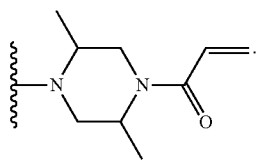 [SMILES: *N1CC(C)N(C(=O)C=C)CC1C]

Embodiment 17

The compound of embodiment 10 wherein $R^5$ is H.

Embodiment 18

The compound of embodiment 10 wherein $R^6$ is H.

Embodiment 19

The compound of any of one of embodiments 1-18 wherein $R^8$ is —$C_{1-6}$alkyl, —$C_{0-3}$alkylene-$C_{6-14}$aryl, or —$C_{0-3}$alkylene-$C_{3-14}$heteroaryl.

Embodiment 20

The compound of embodiment 19 wherein $R^8$ is —$C_{1-6}$alkyl.

Embodiment 21

The compound of embodiment 19 wherein $R^8$ is —$C_{6-14}$aryl.

Embodiment 22

The compound of embodiment 19 wherein $R^8$ is —$C_{3-14}$heteroaryl.

Embodiment 23

The compound of any one of embodiments 1 to 19, wherein $R^8$ is selected from the group consisting of i-Pr, t-Bu, phenyl, benzyl, $OCH_3$, Cl, cyclopropyl, cyclobutyl, cyclopentyl, cyclohexyl,

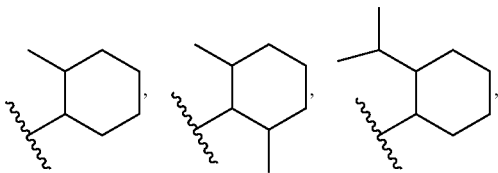

-continued
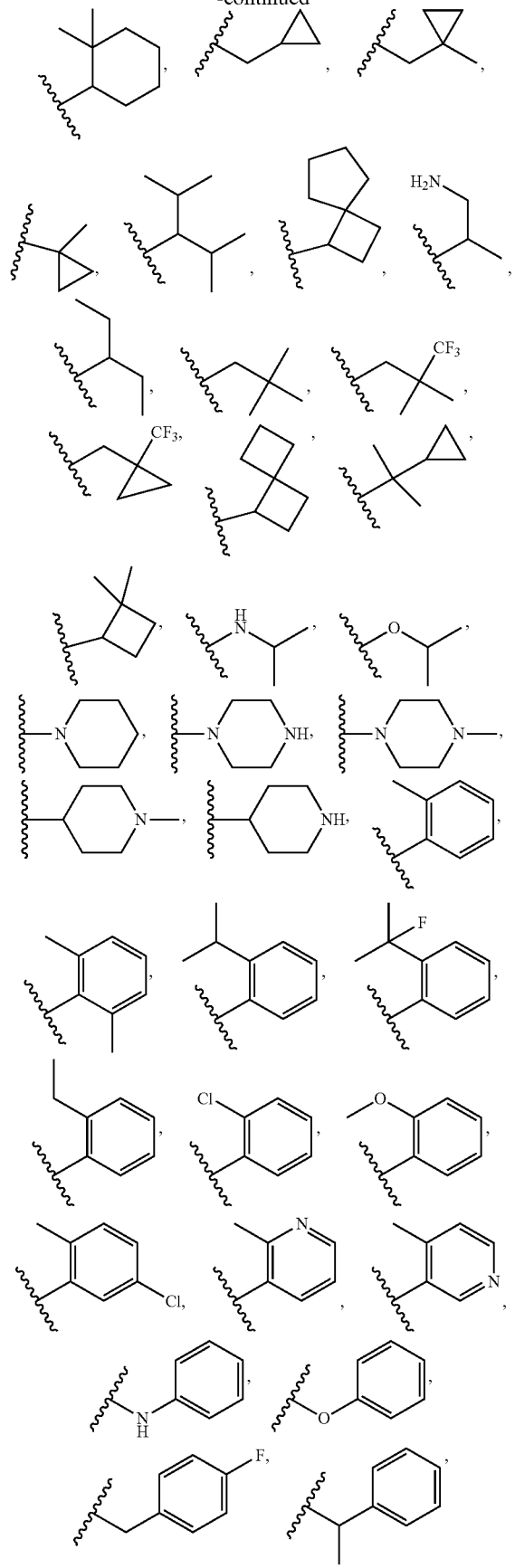
-continued
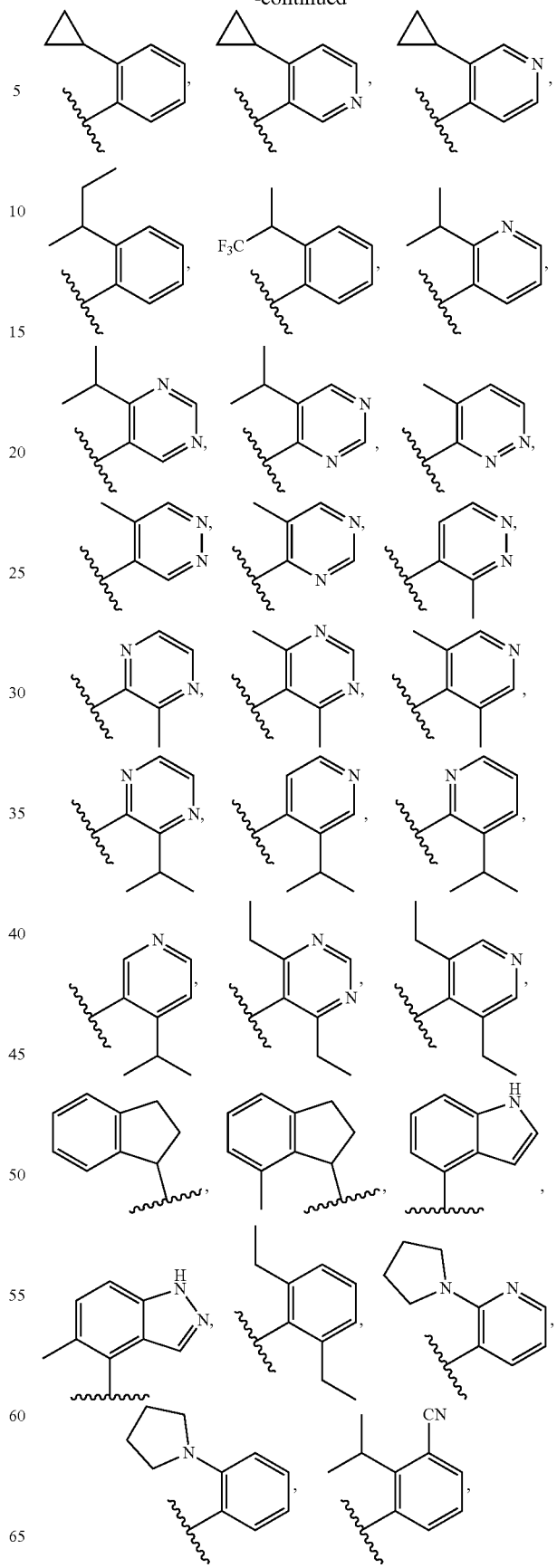

-continued
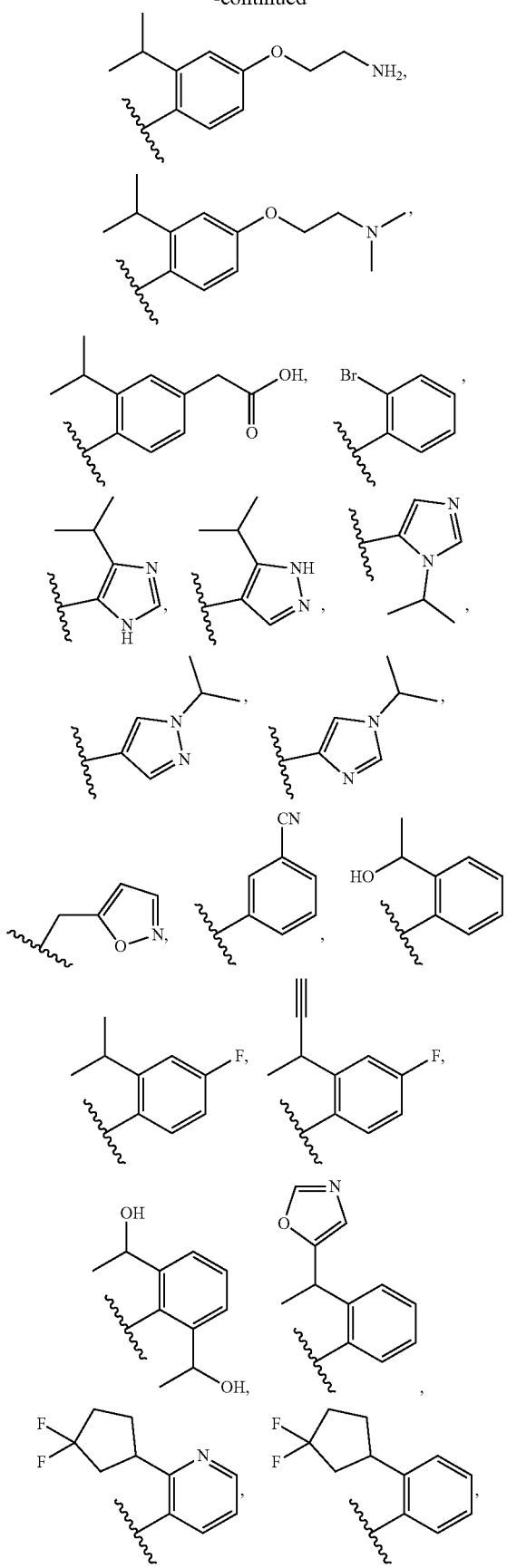
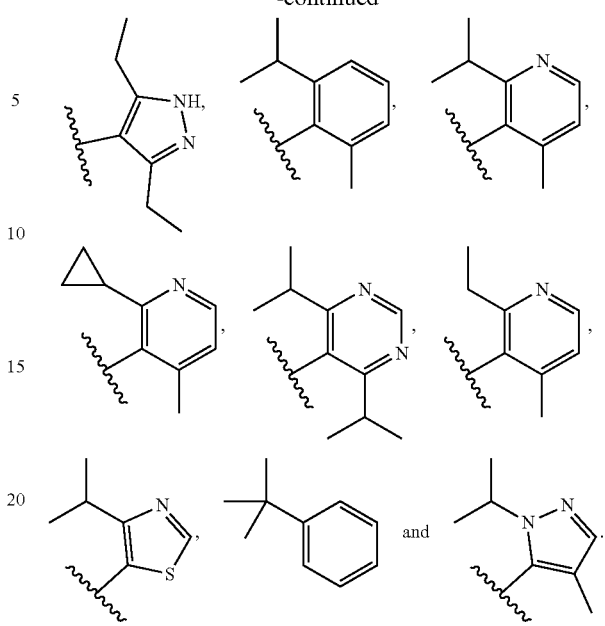
Embodiment 24
The compound of embodiment 23, wherein $R^8$ is selected from the group consisting of
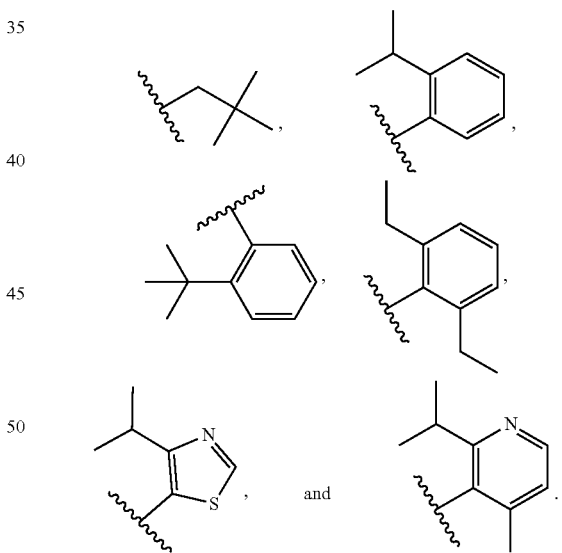
Embodiment 25
The compound of embodiment 23, wherein $R^8$ is

Embodiment 26
The compound of embodiment 23, wherein $R^8$ is
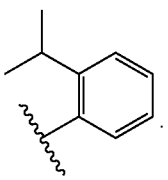 [SMILES: *c1ccccc1C(C)C]
Embodiment 27
The compound of embodiment 23, wherein $R^8$ is
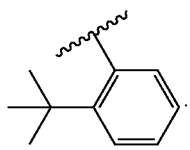 [SMILES: *c1ccccc1C(C)(C)C]
Embodiment 28
The compound of embodiment 23, wherein $R^8$ is
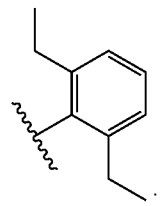 [SMILES: *c1c(CC)cccc1CC]
Embodiment 29
The compound of embodiment 23, wherein $R^8$ is
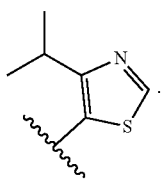 [SMILES: *c1scnc1C(C)C]
Embodiment 30
The compound of embodiment 23, wherein $R^8$ is
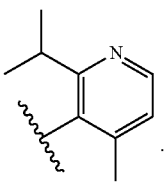 [SMILES: *c1c(C)ccnc1C(C)C]
Embodiment 31
A compound having a structure selected from the formula
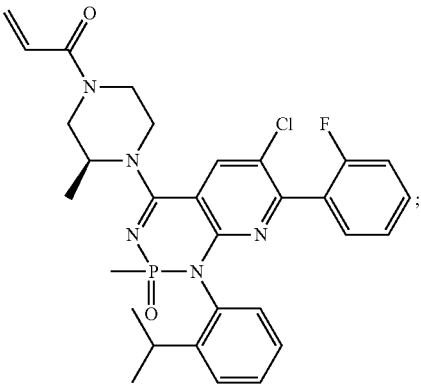
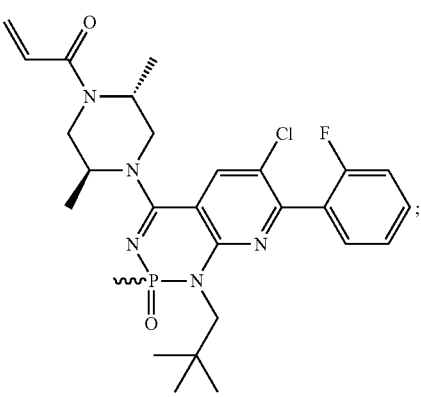
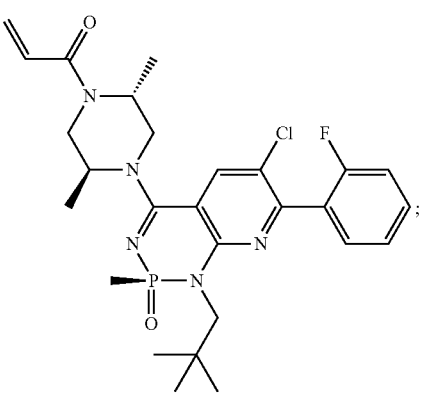
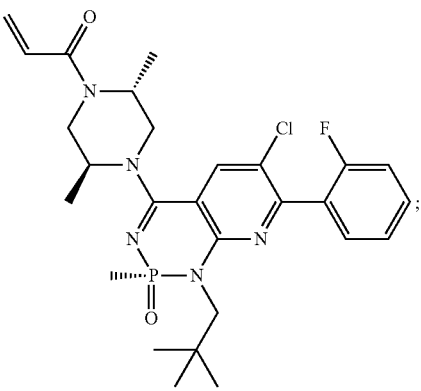

31
-continued
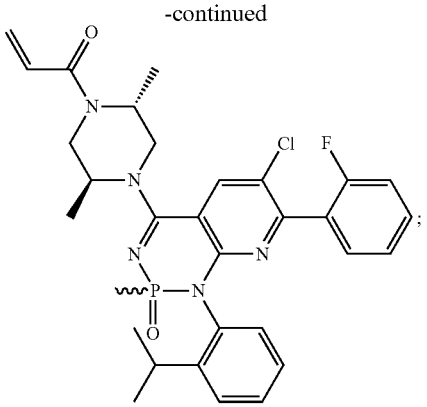
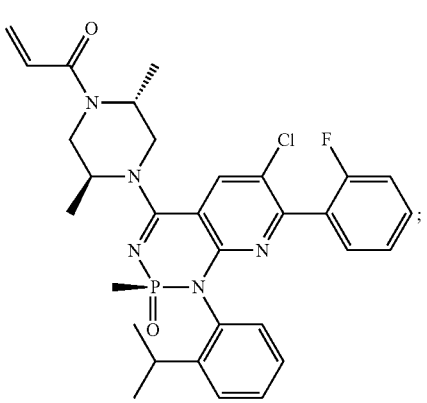
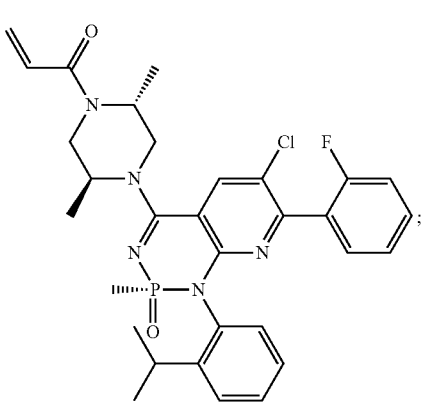
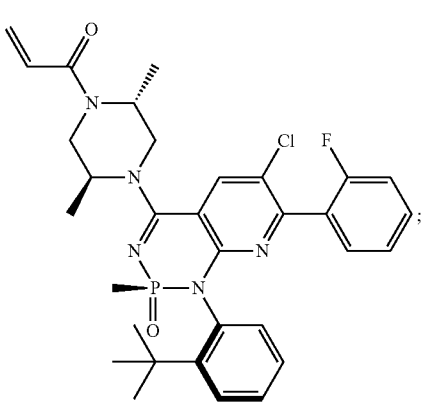
32
-continued
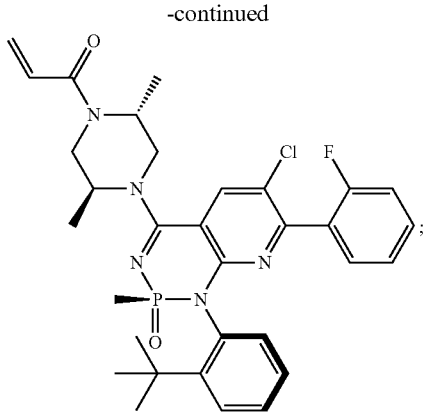
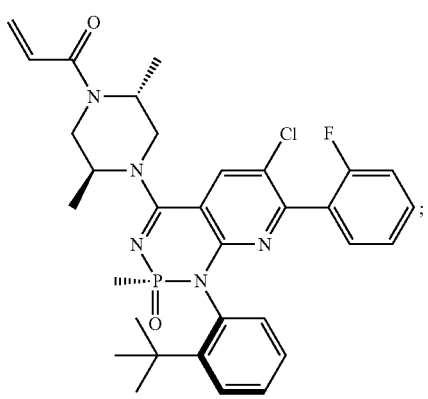
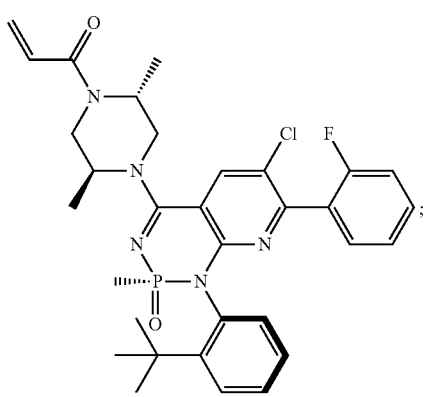
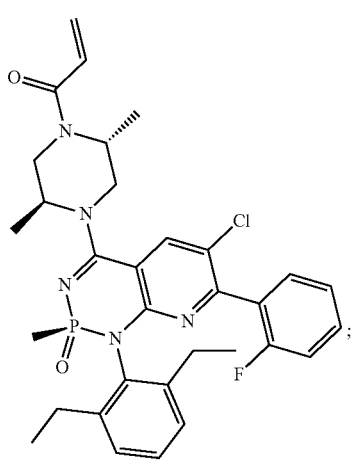

33
-continued
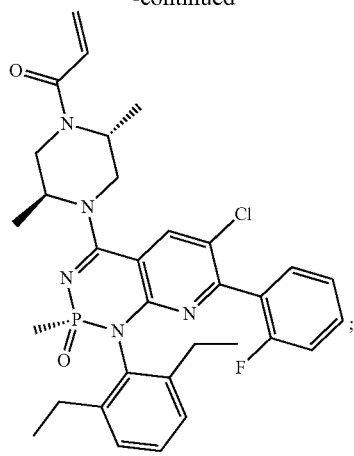
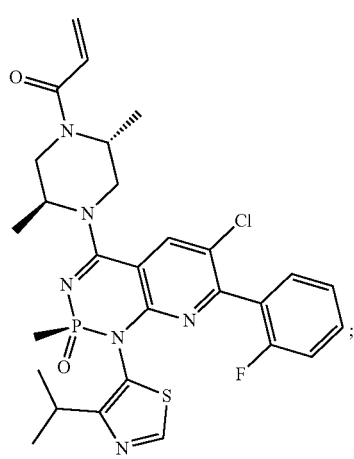
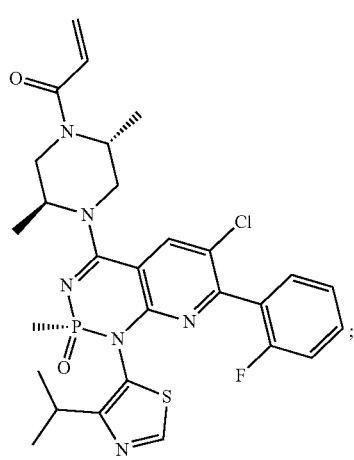
34
-continued
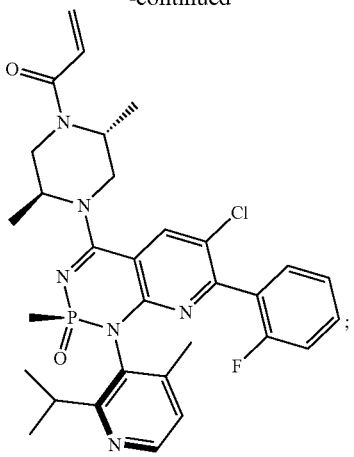
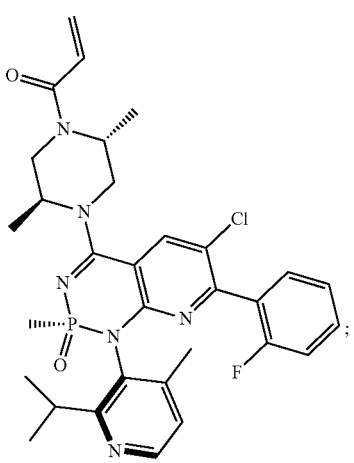
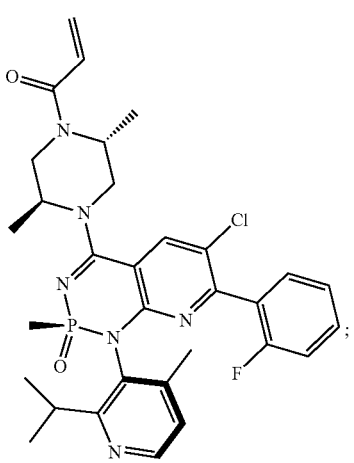

-continued

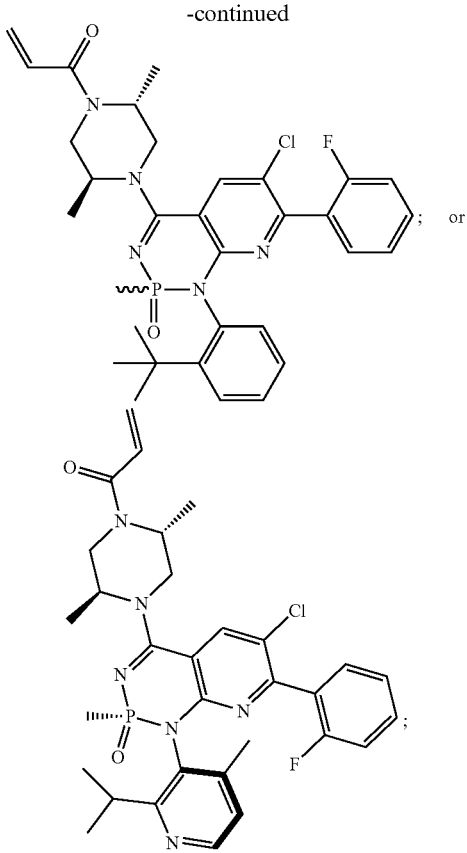

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 32

The compound of any one of embodiments 1-31 in the form of a pharmaceutically acceptable salt.

Embodiment 33

A pharmaceutical formulation comprising the compound of any one of embodiments 1-32 and a pharmaceutically acceptable excipient.

Embodiment 34

A method of inhibiting KRAS G12C in a cell, comprising contacting the cell with the compound of any one of embodiments 1-32 or the composition of embodiment 33.

Embodiment 35

A method of treating cancer in a subject comprising administering to the subject a therapeutically effective amount of the compound of any one of embodiments 1-32 or the composition of embodiment 33.

Embodiment 36

The method of embodiment 35, wherein the cancer is lung cancer, pancreatic cancer, or colorectal cancer.

Embodiment 37

The method of embodiment 36, wherein the cancer is lung cancer.

Embodiment 38

The method of embodiment 37, wherein the cancer is non-small cell lung cancer.

Embodiment 39

The method of embodiment 36, wherein the cancer is pancreatic cancer.

Embodiment 40

The method of embodiment 36, wherein the cancer is colorectal cancer.

Embodiment 41

The method of embodiment 35, further comprising administering to the patient in need thereof a therapeutically effective amount of an additional pharmaceutically active compound.

Embodiment 42

The method of embodiment 41, wherein the additional pharmaceutically active compound is an anti-PD-1 antibody.

Embodiment 43

The method of embodiment 42, wherein the additional pharmaceutically active compound is nivolumab.

Embodiment 44

The method of embodiment 42, wherein the additional pharmaceutically active compound is pembrolizumab.

Embodiment 45

The method of embodiment 42, wherein the additional pharmaceutically active compound is AMG 404.

Embodiment 46

The method of embodiment 41, wherein the additional pharmaceutically active compound is AMG-176.

Embodiment 47

The method of embodiment 41, wherein the additional pharmaceutically active compound is daratumumab.

Embodiment 48

The method of embodiment 41, wherein the additional pharmaceutically active compound is an IMiD.

Embodiment 49

Use of a compound according to any one of embodiments 1-32 for treating cancer in a subject.

Embodiment 50

A compound according to any one of embodiments 1-32 in the preparation of a medicament for treating cancer.

Embodiment 51

The compound according to embodiment 50, wherein the cancer is a solid tumor.

Synthesis of Disclosed Compounds

Compounds as disclosed herein can be synthesized via a number of specific methods. The examples which outline specific synthetic routes, and the generic schemes below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

Pharmaceutical Compositions, Dosing, and Routes of Administration

Also provided herein are pharmaceutical compositions that includes a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See. e.g., Remington's Pharmaceutical Sciences, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable e" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine. L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

While individual needs vary, determination of optimal ranges of effective amounts of the compound is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 1000 mg/day, about 5 mg/day to about 500 mg/day, about 10 mg/day to about 250 mg/day, about 3 mg/day to about 100 mg/day, or about 100 mg/day to about 250 mg/day. Such doses may be administered in a single dose or it may be divided into multiple doses.

Methods of Using KRAS G12C Inhibitors

The present disclosure provides a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The disclosure also provides methods of using the compounds or pharmaceutical compositions of the present disclosure to treat disease conditions, including but not limited to conditions implicated by G12C KRAS, HRAS or NRAS mutation (e.g., cancer).

In some embodiments, a method for treatment of cancer is provided, the method comprising administering an effective amount of any of the foregoing pharmaceutical compositions comprising a compound as disclosed herein to a subject in need thereof. In some embodiments, the cancer is mediated by a KRAS, HRAS or NRAS G12C mutation. In various embodiments, the cancer is pancreatic cancer, colorectal cancer or lung cancer. In some embodiments, the cancer is gall bladder cancer, thyroid cancer, and bile duct cancer.

In some embodiments the disclosure provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound as disclosed herein or a pharmaceutically acceptable salt thereof.

The disclosed compounds inhibit anchorage-independent cell growth and therefore have the potential to inhibit tumor metastasis. Accordingly, another embodiment the disclosure provides a method for inhibiting tumor metastasis, the method comprising administering an effective amount a compound disclosed herein.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g. Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of a compound as disclosed herein, or a pharmaceutically acceptable salt thereof. In some embodiments, said method relates to the treatment of a subject who suffers from a cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In some embodiments, the methods for treatment are directed to treating lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

The disclosure further provides methods of modulating a G12C Mutant KRAS, HRAS or NRAS protein activity by contacting the protein with an effective amount of a compound of the disclosure. Modulation can be inhibiting or activating protein activity. In some embodiments, the disclosure provides methods of inhibiting protein activity by contacting the G12C Mutant KRAS, HRAS or NRAS protein with an effective amount of a compound of the disclosure in solution. In some embodiments, the disclosure provides methods of inhibiting the G12C Mutant KRAS, HRAS or NRAS protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of a compound of the disclosure. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting KRAS, HRAS or NRAS G12C activity in a cell by contacting said cell with an amount of a compound of the disclosure sufficient to inhibit the activity of KRAS, HRAS or NRAS G12C in said cell. In some embodiments, the disclosure provides methods of inhibiting KRAS, HRAS or NRAS G12C activity in a tissue by contacting said tissue with an amount of a compound of the disclosure sufficient to inhibit the activity of KRAS, HRAS or NRAS G12C in said tissue. In some embodiments, the disclosure provides methods of inhibiting KRAS, HRAS or NRAS G12C activity in an organism by contacting said organism with an amount of a compound of the disclosure sufficient to inhibit the activity of KRAS, HRAS or NRAS G12C in said organism. In some embodiments, the disclosure provides methods of inhibiting KRAS, HRAS or NRAS G12C activity in an animal by contacting said animal with an amount of a compound of the disclosure sufficient to inhibit the activity of KRAS, HRAS or NRAS G12C in said animal. In some embodiments, the disclosure provides methods of inhibiting KRAS, HRAS or NRAS G12C activity in a mammal by contacting said mammal with an amount of a compound of the disclosure sufficient to inhibit the activity of KRAS, HRAS or NRAS G12C in said mammal. In some embodiments, the disclosure provides methods of inhibiting KRAS, HRAS or NRAS G12C activity in a human by contacting said human with an amount of a compound of the disclosure sufficient to inhibit the activity of KRAS, HRAS or NRAS G12C in said human. The present disclosure provides methods of treating a disease mediated by KRAS, HRAS or NRAS G12C activity in a subject in need of such treatment.

Combination Therapy:

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), Venclexta™ (venetoclax) and Adriamycin™, (docorubicin) as well as a host of chemotherapeutic agents. Non-limiting examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, chlorocyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins, capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylomithine (DMFO).

Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931 788, WO 90/05719, WO 99/52910, WO 99/52889, WO 99/29667, WO1999007675, European Patent Publication EP1786785, European Patent Publication No. EP1181017, United States Publication No. US20090012085, United States Publication U.S. Pat. No. 5,863,949, United States Publication U.S. Pat. No. 5,861, 510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-$_{n3}$, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRc Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vilro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxvestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto. Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genacra, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin A 1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 176; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as *vinca* alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNTO328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zamestra™), anti-CD138 (e.g., BT062), Torc1/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds of the present invention may also be used in combination with an additional pharmaceutically active compound that disrupts or inhibits RAS-RAF-ERK or PI3K-AKT-TOR signaling pathways. In other such combinations, the additional pharmaceutically active compound is a PD-I and PD-L1 antagonist. The compounds or pharmaceutical compositions of the disclosure can also be used in combination with an amount of one or more substances selected from EGFR inhibitors, MEK inhibitors, PI3K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., *Pharmacogenetics and Pharmacogenomics In Oncology Therapeutic Antibody Development*, BioTechniques 2005; 39(4); 565-8, and Paez J G, et. al., *EGFR Mutations In Lung Cancer Correlation With Clinical Response To Gefitinib Therapy*, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published Jan. 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12): 1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995. Clin. Cancer Res. 1:1311-1318; Huang, S. M., et al., 1999, Cancer Res. 15:59(8): 1935-40; and Yang, X., et al., 1999, Cancer Res. 59:1236-1243. Thus, the EGFR inhibitor can be monoclonal antibody Mab E7.6.3 (Yang, 1999 supra), or Mab $C_{225}$ (ATCC Accession No. HB-8508), or an antibody or antibody fragment having the binding specificity thereof.

MEK inhibitors include, but are not limited to, tremetinib (Mekinist®), CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Akt1) (Barnett et al. (2005) Biochem. J. 385 (Pt. 2), 399-408); Akt-1-1,2 (inhibits Ak1 and 2) (Barnett et al. (2005) Biochem. J. 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine (e.g., interferes with Akt membrane localization; Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); and triciribine (TCN or API-2 or NCI identifier: NSC 154020; Yang et al. (2004) Cancer Res. 64, 4394-9).

TOR inhibitors include, but are not limited to, AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl)rapamycin, 40-[3-hydroxy (hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

MCl-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

SHP inhibitors include, but are not limited to, SHP099.

Proteasome inhibitors include, but are not limited to, Kyprolis® (carfilzomib), Velcade® (bortezomib), and oprozomib.

Immune therapies include, but are not limited to, anti-PD-1 agents, anti-PDL-1 agents, anti-CTLA-4 agents, anti-LAG1 agents, and anti-OX40 agents.

Monoclonal antibodies include, but are not limited to, Darzalex® (daratumumab), Herceptin® (trastuzumab), Avastin® (bevacizumab), Rituxan® (rituximab), Lucentis® (ranibizumab), and Eylea® (aflibercept).

Immunomodulatory imide drugs (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., *Blood* 110(1): 186-192 (2007), Thompson et al., *Clin. Cancer Res.* 13(6): 1757-1761 (2007), and Korman et al., International Application No. PCT/JP2006/309606 (publication no. WO 2006/121168 A1), each of which are expressly incorporated by reference herein, include: pembrolizumab (Keytruda®), nivolumab (Opdivo®), Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG 404, AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

GITR agonists include, but are not limited to, GITR fusion proteins and anti-GITR antibodies (e.g., bivalent anti-GITR antibodies), such as, a GITR fusion protein described in U.S. Pat. No. 6,111,090box.c, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

EXAMPLES

Method 1

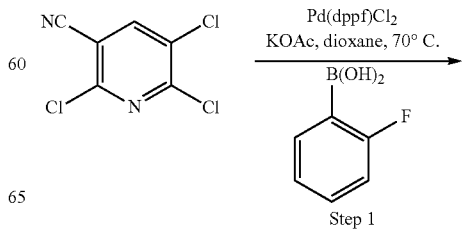

Step 1

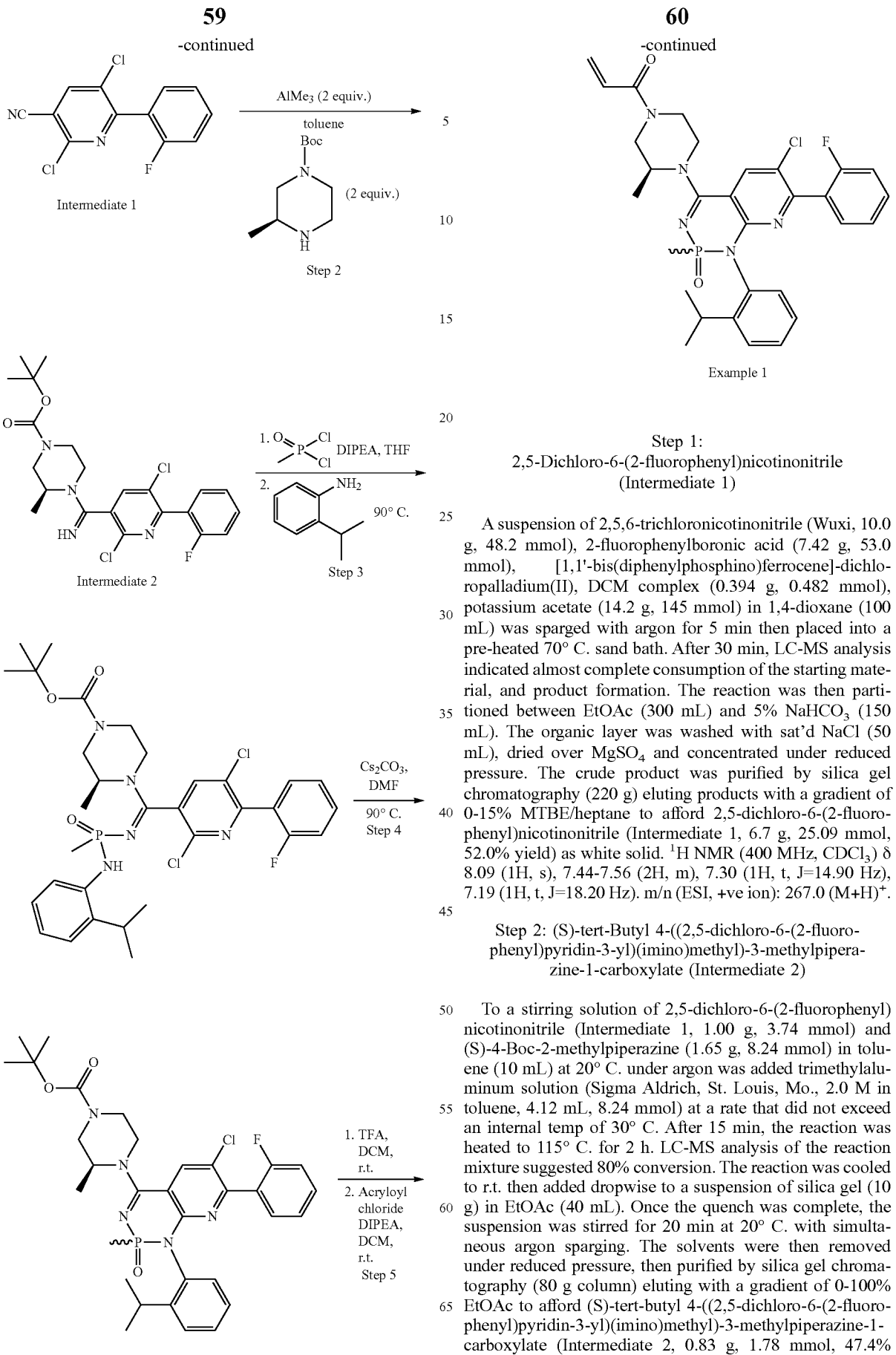

Example 1

Step 1:
2,5-Dichloro-6-(2-fluorophenyl)nicotinonitrile
(Intermediate 1)

A suspension of 2,5,6-trichloronicotinonitrile (Wuxi, 10.0 g, 48.2 mmol), 2-fluorophenylboronic acid (7.42 g, 53.0 mmol), [1,1'-bis(diphenylphosphino)ferrocene]-dichloropalladium(II), DCM complex (0.394 g, 0.482 mmol), potassium acetate (14.2 g, 145 mmol) in 1,4-dioxane (100 mL) was sparged with argon for 5 min then placed into a pre-heated 70° C. sand bath. After 30 min, LC-MS analysis indicated almost complete consumption of the starting material, and product formation. The reaction was then partitioned between EtOAc (300 mL) and 5% NaHCO$_3$ (150 mL). The organic layer was washed with sat'd NaCl (50 mL), dried over MgSO$_4$ and concentrated under reduced pressure. The crude product was purified by silica gel chromatography (220 g) eluting products with a gradient of 0-15% MTBE/heptane to afford 2,5-dichloro-6-(2-fluorophenyl)nicotinonitrile (Intermediate 1, 6.7 g, 25.09 mmol, 52.0% yield) as white solid. $^1$H NMR (400 MHz, CDCl$_3$) δ 8.09 (1H, s), 7.44-7.56 (2H, m), 7.30 (1H, t, J=14.90 Hz), 7.19 (1H, t, J=18.20 Hz). m/n (ESI, +ve ion): 267.0 (M+H)$^+$.

Step 2: (S)-tert-Butyl 4-((2,5-dichloro-6-(2-fluorophenyl)pyridin-3-yl)(imino)methyl)-3-methylpiperazine-1-carboxylate (Intermediate 2)

To a stirring solution of 2,5-dichloro-6-(2-fluorophenyl)nicotinonitrile (Intermediate 1, 1.00 g, 3.74 mmol) and (S)-4-Boc-2-methylpiperazine (1.65 g, 8.24 mmol) in toluene (10 mL) at 20° C. under argon was added trimethylaluminum solution (Sigma Aldrich, St. Louis, Mo., 2.0 M in toluene, 4.12 mL, 8.24 mmol) at a rate that did not exceed an internal temp of 30° C. After 15 min, the reaction was heated to 115° C. for 2 h. LC-MS analysis of the reaction mixture suggested 80% conversion. The reaction was cooled to r.t. then added dropwise to a suspension of silica gel (10 g) in EtOAc (40 mL). Once the quench was complete, the suspension was stirred for 20 min at 20° C. with simultaneous argon sparging. The solvents were then removed under reduced pressure, then purified by silica gel chromatography (80 g column) eluting with a gradient of 0-100% EtOAc to afford (S)-tert-butyl 4-((2,5-dichloro-6-(2-fluorophenyl)pyridin-3-yl)(imino)methyl)-3-methylpiperazine-1-carboxylate (Intermediate 2, 0.83 g, 1.78 mmol, 47.4% yield) as orange foam. $^1$H NMR (400 MHz, CDCl$_3$) δ 7.72 (1H, s), 7.45-7.52 (2H, m), 7.27-7.31 (1H, m), 7.14-7.22 (1H, m), 3.80-4.25 (3H, m), 2.75-3.50 (4H, m), 1.48 (9H, s), 1.27 (3H, d, J=7.05 Hz). $^{19}$F NMR (376 MHz, CDCl$_3$) δ −112.76 (1 F, s). m/z (ESI, +ve ion): 467.1 (M+H)$^+$.

Step 3: tert-Butyl (3S)-4-((Z)-(2,5-dichloro-6-(2-fluorophenyl)pyridin-3-yl)((((2-isopropylphenyl)amino)(methyl)phosphoryl)imino)methyl)-3-methylpiperazine-carboxylate To a solution of methylphosphonoyl dichloride (Sigma-Aldrich, St. Louis, Mo., 0.12 g, 0.94 mmol) in THF (3 mL) was added a solution of tert-butyl (S)-4-(2,5-dichloro-6-(2-fluorophenyl)pyridin-3-yl)(imino)methyl)-3-methylpiperazine-1-carboxylate (Intermediate 2, 0.40 g, 0.85 mmol) in THF (1 mL) at r.t. The reaction mixture was stirred for 12 h and 2-isopropylaniline (Sigma-Aldrich, St. Louis, Mo., 0.12 mL, 0.94 mmol) and DIPEA (0.11 g, 0.85 mmol) were added. The resulting mixture was heated to 90° C. for 12 h, concentrated and the crude residue was purified by silica gel chromatography eluting with 0-50% EtOAc/EtOH (3:1) in heptane to provide tert-butyl (3S)-4-((Z)-(2,5-dichloro-6-(2-fluorophenyl)pyridin-3-yl)((((2-isopropylphenyl)amino)(methyl)phosphoryl)imino)methyl)-3-methylpiperazine-1-carboxylate (0.07 g, 0.11 mmol, 12.3% yield). $^{19}$F NMR (376 MHz, CDCl$_3$) δ −112.35 (s, 1F). m/z (ESI, +ve ion): 662.3 (M+H)$^+$.

Step 4: tert-Butyl (3S)-4-(6-chloro-7-(2-fluorophenyl)-1-(2-isopropylphenyl)-2-methyl-2-oxido-1H-pyrido[2,3-d][1,3,2]diazaphosphinin-4-yl)-3-methylpiperazine-1-carboxylate A mixture of tert-butyl (3S)-4-((Z)-(2,5-dichloro-6-(2-fluorophenyl)pyridin-3-yl)((((2-isopropylphenyl)amino)(methyl)phosphoryl)imino)methyl)-3-methylpiperazine-1-carboxylate (0.034 g, 0.05 mmol) and cesium carbonate (0.084 g, 0.25 mmol) in DMF (0.5 mL) was heated to 90° C. for 2 h. The reaction mixture was then diluted with EtOAc and washed with brine. The organic layer was dried over Na$_2$SO$_4$, filtered, and concentrated in vacuo to provide crude tert-butyl (3S)-4-(6-chloro-7-(2-fluorophenyl)-1-(2-isopropylphenyl)-2-methyl-2-oxido-1H-pyrido[2,3-d][1,3,2]diazaphosphinin-4-yl)-3-methylpiperazine-1-carboxylate (0.02 g, 0.04 mmol, 78.0% yield) which was used in the next step without further purification. m/z (ESI, +ve ion): 626.3 (M+H)$^+$.

Step 5: 1-((3S)-4-(6-Chloro-7-(2-fluorophenyl)-1-(2-isopropylphenyl)-2-methyl-2-oxido-1H-pyrido[2,3-d][1,3,2]diazaphosphinin-4-yl)-3-methylpiperazin-1-yl)prop-2-en-1-one (3376047 Example 1)

TFA (0.06 mL, 0.79 mmol) was added to a solution of tert-butyl (3S)-4-(6-chloro-7-(2-fluorophenyl)-1-(2-isopropylphenyl)-2-methyl-2-oxido-1H-pyrido[2,3-d][1,3,2]diazaphosphinin-4-yl)-3-methylpiperazine-1-carboxylate (0.03 g, 0.04 mmol) in DCM (1 mL). The resulting mixture was stirred at r.t. for 1 h then concentrated under reduced pressure. The residue was suspended in DCM (1 mL), cooled to 0° C., and treated with DIPEA (0.02 mL, 0.08 mmol) followed by acryloyl chloride (0.07 mL, 0.08 mmol). The reaction was warmed to r.t. and stirred for 10 min. The mixture was quenched with a saturated aqueous solution of NaHCO$_3$ and extracted with DCM (2×). The combined organics were concentrated and the residue purified with ISCO using 0-60% EtOAc/EtOH (3:1) in heptane to provide 1-((3S)-4-(6-chloro-7-(2-fluorophenyl)-1-(2-isopropylphenyl)-2-methyl-2-oxido-1H-pyrido[2,3-d][1,3,2]diazaphos-phinin-4-yl)-3-methylpiperazin-1-yl)prop-2-en-1-one (Example 1, 0.01 g, 0.02 mmol, 51.8% yield) as a mixture of 2 isomers. $^{19}$F NMR (376 MHz, CDCl$_3$) δ −112.70 (s, 1F). m/z (ESI, +ve ion): 580.3 (M+H)$^+$.

Method 2

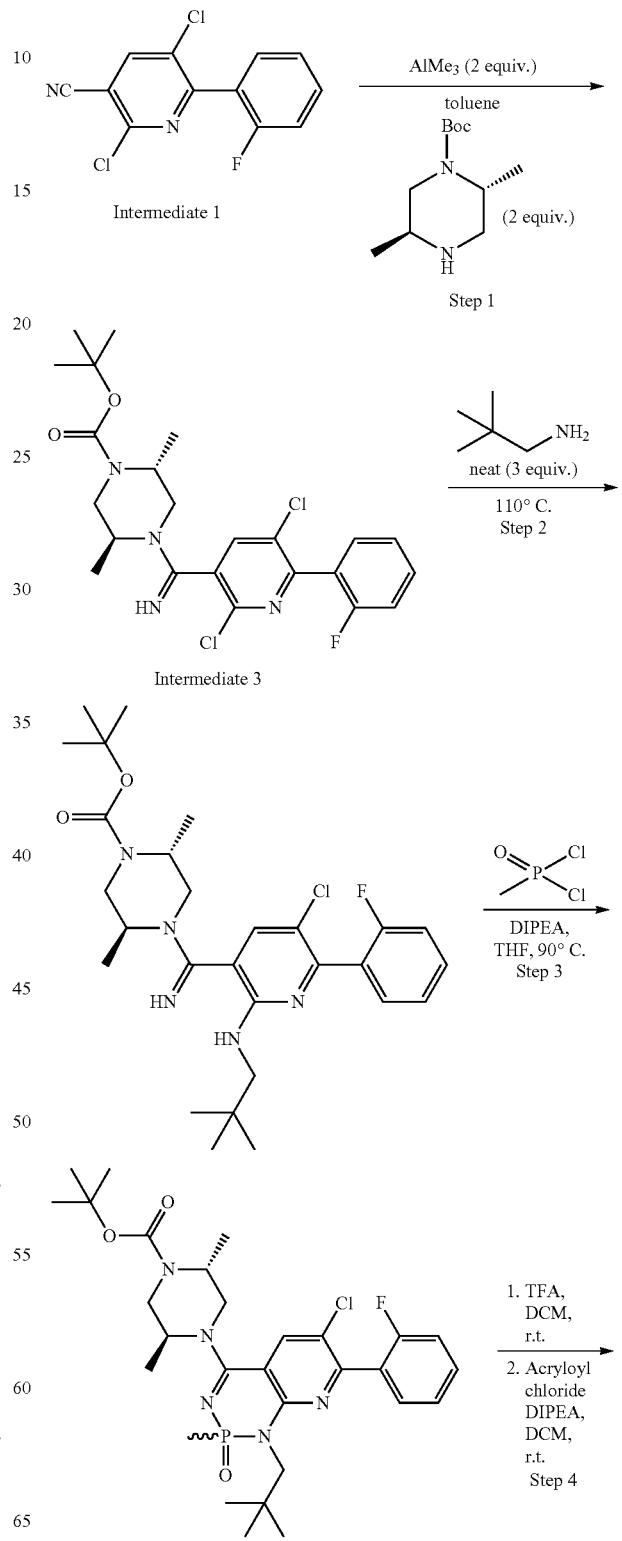

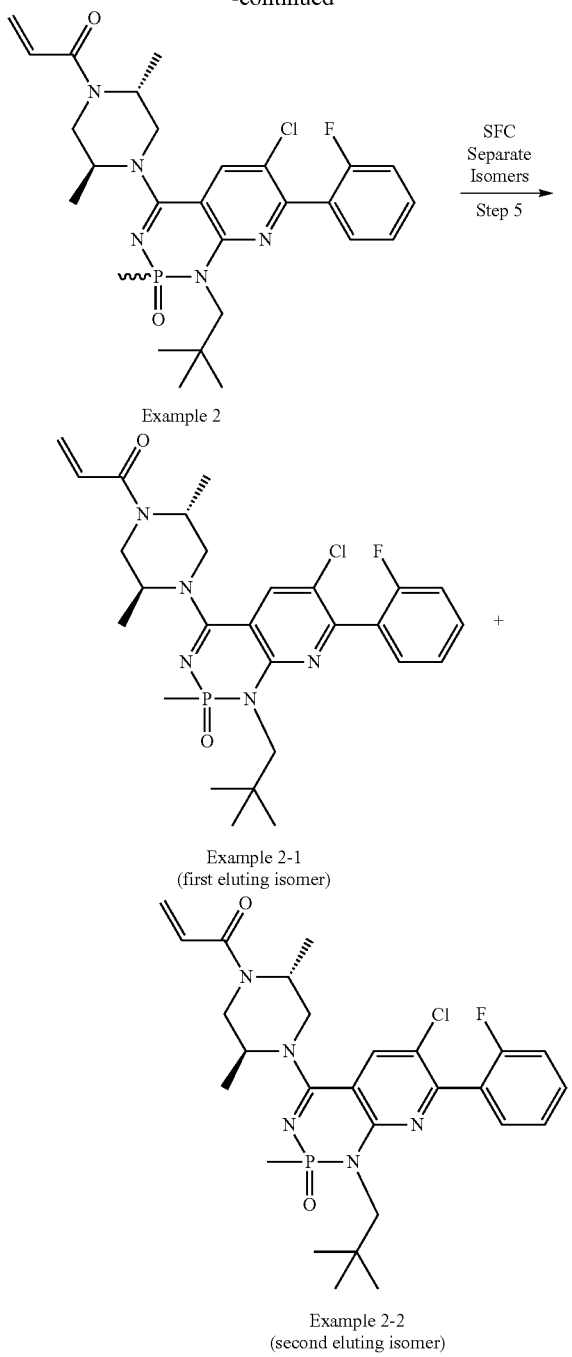

Example 2

Example 2-1
(first eluting isomer)

Example 2-2
(second eluting isomer)

Step 1: tert-butyl (2R,5S)-4-((2,5-dichloro-6-(2-fluorophenyl)pyridin-3-yl)(imino)methyl)-2,5-dimethylpiperazine-1-carboxylate (Intermediate 3)

A 3-necked 1-L flask equipped with an overhead stirrer, thermocouple and nitrogen inlet was charged with 2,5-dichloro-6-(2-fluorophenyl)nicotinonitrile (Intermediate 1, 30 g, 112 mmol), tert-butyl (2R,5S)-2,5-dimethylpiperazine-1-carboxylate (48.1 g, 225 mmol) and toluene (210 mL). The flask was degassed and purged with nitrogen then charged with trimethylaluminum (Sigma-Aldrich, 2M in toluene, 112 mL, 225 mmol) dropwise via addition funnel while maintaining an internal temperature below 30° C. The reaction mixture was stirred for 30 min and warmed to 110° C. for 1.5 h. Upon cooling to r.t., the reaction solution was transferred to an addition funnel via cannula and then slowly added to a slurry of ethyl acetate (500 mL) and silica gel (300 g) maintaining the internal temperature below 30° C. The slurry was stirred overnight then treated with 2-propanol (150 mL), filtered and washed with ethyl acetate. The filtrate was concentrated to dryness and redissolved in DCM resulting in the formation of a thick tar. Celite was added to the mixture and filtered through a medium frit rinsing with DCM and concentrating to minimal volume. The crude mixture was purified by chromatography on a 340 g silica gel column using a gradient of 0-100% EtOAc/heptane affording tert-butyl (2R,5S)-4-((2,5-dichloro-6-(2-fluorophenyl)pyridin-3-yl)(imino)methyl)-2,5-dimethylpiperazine-1-carboxylate (Intermediate 3, 27.7 g, 57.6 mmol, 51% yield) as pale yellow oil. $^1$H NMR (400 MHz, DMSO-$d_6$) δ 8.73-9.01 (m, 1H), 8.24-8.52 (m, 1H), 7.51-7.66 (m, 2H), 7.41 (br t, J=7.57 Hz, 2H), 4.30-4.86 (m, 1H), 4.09-4.26 (m, 1H), 3.28-3.87 (m, 3H), 2.91-3.28 (m, 1H), 1.42 (br s, 9H), 1.12-1.32 (m, 6H). $^{19}$F NMR (376 MHz, DMSO-$d_6$) δ −113.66 (s, 1F). m/z (ESI, +ve ion): 481.2 (M+H)$^+$.

Step 2: tert-Butyl (2R,5S)-4-((5-chloro-6-(2-fluorophenyl)-2-(neopentylamino)pyridin-3-yl)(imino)methyl)-2,5-dimethylpiperazine-1-carboxylate A mixture of tert-butyl (2R,5S)-4-((2,5-dichloro-6-(2-fluorophenyl)pyridin-3-yl)(imino)methyl)-2,5-dimethylpiperazine-1-carboxylate (Intermediate 3, 1.30 g, 2.70 mmol) and neopentylamine (1.27 mL, 10.80 mmol) was heated at 110° C. for 3 d. The reaction mixture was diluted with DCM (2 mL) and purified by silica gel chromatography using 0-5% MeOH in DCM to afford tert-butyl (2R,5S)-4-((5-chloro-6-(2-fluorophenyl)-2-(neopentylamino)pyridin-3-yl)(imino)methyl)-2,5-dimethylpiperazine-1-carboxylate (1.10 g, 2.07 mmol, 77.0% yield). m/z (ESI, +ve ion): 532.3 (M+H)$^+$.

Step 3: tert-Butyl (2R,5S)-4-(6-chloro-7-(2-fluorophenyl)-2-methyl-1-neopentyl-2-oxido-1H-pyrido[2,3-d][1,3,2]diazaphosphinin-4-yl)-2,5-dimethylpiperazine-1-carboxylate A solution of methylphosphonic dichloride (0.37 mL, 2.78 mmol) in THF (5 mL) was added to a mixture of tert-butyl (2R,5S)-4-((5-chloro-6-(2-fluorophenyl)-2-(neopentylamino)pyridin-3-yl)(imino)methyl)-2,5-dimethylpiperazine-1-carboxylate (0.37 g, 0.70 mmol) and DIPEA (0.60 mL, 3.48 mmol). The resulting solution was heated to 90° C. for 12 h, diluted with water and extracted with EtOAc (2×). The organic layers were combined, dried over MgSO$_4$, and concentrated to afford crude tert-butyl (2R,5S)-4-(6-chloro-7-(2-fluorophenyl)-2-methyl-1-neopentyl-2-oxido-1H-pyrido[2,3-d][1,3,2]diazaphosphinin-4-yl)-2,5-dimethylpiperazine-1-carboxylate (0.34 g, 0.57 mmol, 83.0% yield). m/z (ESI, +ve ion): 592.3 (M+H)$^+$. This material was used in the subsequent step without further purification.

Step 4: 1-((2R,5S)-4-(6-Chloro-7-(2-fluorophenyl)-2-methyl-1-neopentyl-2-oxido-1H-pyrido[2,3-d][1,3,2]diazaphosphinin-4-yl)-2,5-dimethylpiperazin-1-yl)prop-2-en-1-one (Example 2)

TFA (0.85 mL, 11.5 mmol) was added to a solution of tert-butyl-(2R,5S)-4-(6-chloro-7-(2-fluorophenyl)-2-methyl-1-neopentyl-2-oxido-1H-pyrido[2,3-d][1,3,2]diazaphosphinin-4-yl)-2,5-dimethylpiperazine-1-carboxylate (0.34 g, 0.57 mmol) in DCM (4 mL). The resulting mixture was stirred at r.t. for 1 h and then concentrated under reduced pressure. The residue was suspended in DCM (4 mL), cooled to 0° C., and treated with DIPEA (0.30 mL, 1.72 mmol) followed by acryloyl chloride (0.05 mL, 0.057 mmol). The reaction was warmed to r.t. and stirred for 10 min. The mixture was quenched with sat'd aqueous NaHCO$_3$ and extracted with DCM (2×) and the combined organic layers were concentrated and the residue purified on silica gel using 0-50% EtOAc/EtOH (3:1) in heptane to provide 1-((2R,5S)-4-(6-chloro-7-(2-fluorophenyl)-2-methyl-1-neopentyl-2-oxido-1H-pyrido[2,3-d][1,3,2]diazaphosphinin-4-yl)-2,5-dimethylpiperazin-1-yl)prop-2-en-1-one (Example 2, 0.26 g, 0.24 mmol, 41.5% yield) as a mixture of 2 stereoisomers. $^1$H NMR (400 MHz, DMSO-d$_6$) δ 7.96-8.19 (m, 1H), 7.48-7.61 (m, 2H), 7.34-7.41 (m, 2H), 6.76 (ddd, J=6.63, 10.31, 16.64 Hz, 1H), 6.15 (br d, J=16.79 Hz, 1H), 5.69-5.75 (m, 1H), 4.25-4.80 (m, 2H), 3.97-4.15 (m, 1H), 3.79-3.95 (m, 1H), 3.76 (br s, 1H), 3.40-3.70 (m, 2H), 3.17-3.25 (m, 1H), 1.19-1.29 (m, 6H), 0.96-1.16 (m, 3H), 0.83-0.86 (m, 9H). $^{19}$F NMR (376 MHz, DMSO-d$_6$) δ −113.42 (s, 1F). $^{31}$P NMR (162 MHz, DMSO-d$_6$) δ 25.55 (s, 1P). m/z (ESI, +ve ion): 546.2 (M+H)$^+$.

Step 5: 1-((2R,5S)-4-(6-chloro-7-(2-fluorophenyl)-2-methyl-1-neopentyl-2-oxido-1H-pyrido[2,3-d][1,3,2]diazaphosphinin-4-yl)-2,5-dimethylpiperazin-1-yl)prop-2-en-1-one First Eluting Isomer (Example 2-1) and Second Eluting Isomer (Example 2-2)

A mixture of isomers, Example 2 (260 mg) was purified by preparative SFC using an OX—H column 21×250 mm, 5 μm, a mobile phase of 50% methanol/CO$_2$, 7 mL/min to generate 46 mg of peak 1 with purity of 99.0% and D.E.>99.0%, 168 mg of peak 2 with purity of 99.0% and D.E. ~96.5%. D.E. determination by SFC: Chiralpak IC, 15% methanol.

First Eluting Isomer (Example 2-1)

$^1$H NMR (400 MHz, CD$_2$Cl$_2$) δ 7.69 (d, J=8.91 Hz, 1H), 7.39-7.47 (m, 2H), 7.19-7.26 (m, 1H), 7.12 (t, J=9.18 Hz, 1H), 6.42-6.59 (m, 1H), 6.13-6.23 (m, 1H), 5.60-5.68 (m, 1H), 4.84 (br s, 1H), 4.50 (br d, J=15.96 Hz, 1H), 4.14-4.29 (m, 1H), 3.72-4.11 (m, 2H), 3.51-3.66 (m, 2H), 3.47 (br d, J=13.68 Hz, 1H), 1.29 (br d, J=6.63 Hz, 9H), 0.83 (s, 9H). $^{19}$F NMR (376 MHz, CD$_2$Cl$_2$) δ −113.16 (s, 1F). $^{31}$P NMR (162 MHz, CD$_2$Cl$_2$) δ 25.36 (s, 1P). m/z (ESI, +ve ion): 546.2 (M+H)$^+$.

Second Eluting Isomer (Example 2-2)

$^1$H NMR (400 MHz, CD$_2$Cl$_2$) δ 7.60-7.66 (m, 1H), 7.39-7.46 (m, 2H), 7.22 (t, J=7.26 Hz, 1H), 7.12 (t, J=9.42 Hz, 1H), 6.42-6.56 (m, 1H), 6.18 (br t, J=16.48 Hz, 1H), 5.63 (br dd, J=3.42, 10.47 Hz, 1H), 5.25-5.28 (m, 1H), 4.71 (br s, 1H), 4.03-4.21 (m, 2H), 3.60-3.79 (m, 2H), 3.49-3.58 (m, 1H), 3.20-3.33 (m, 1H), 1.00-1.28 (m, 9H), 0.82 (s, 9H). $^{19}$F NMR (376 MHz, CD$_2$Cl$_2$) δ −113.16 (s, 1F). $^{31}$P NMR (162 MHz. CD$_2$Cl$_2$) δ 26.19 (s, 1P). m/z (ESI, +ve ion): 546.2 (M+H)$^+$.

Method 3:

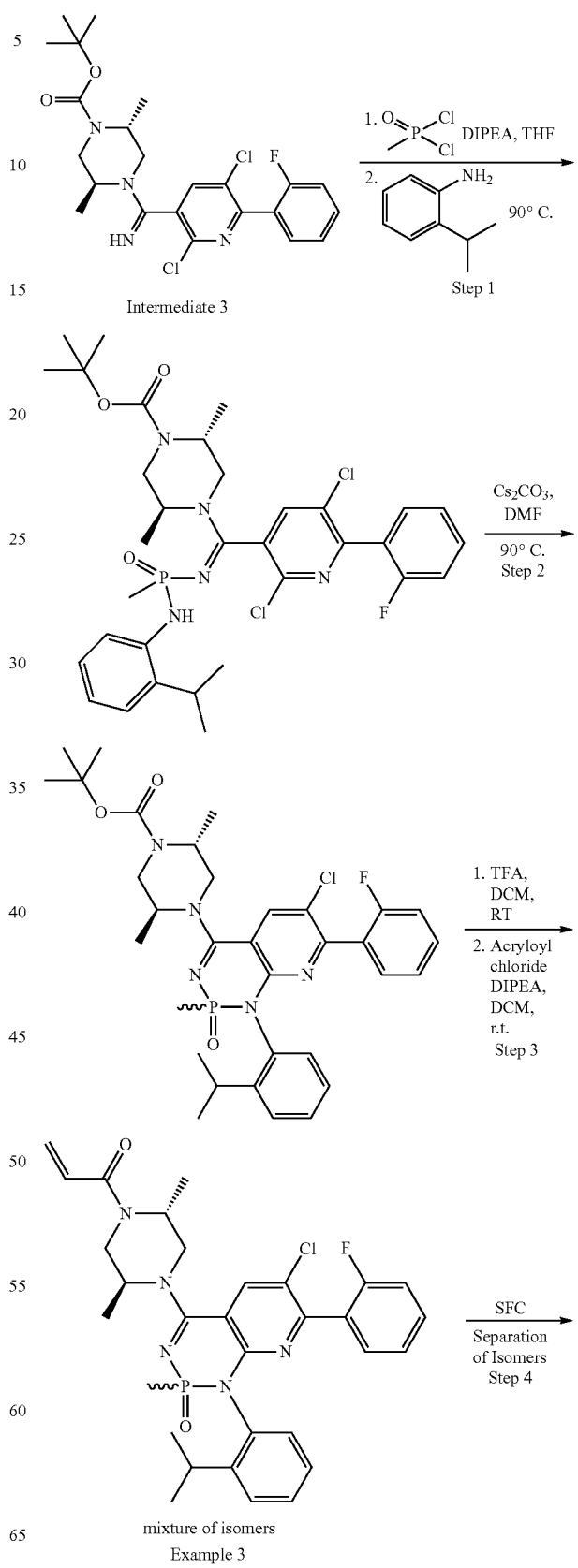

Example 3

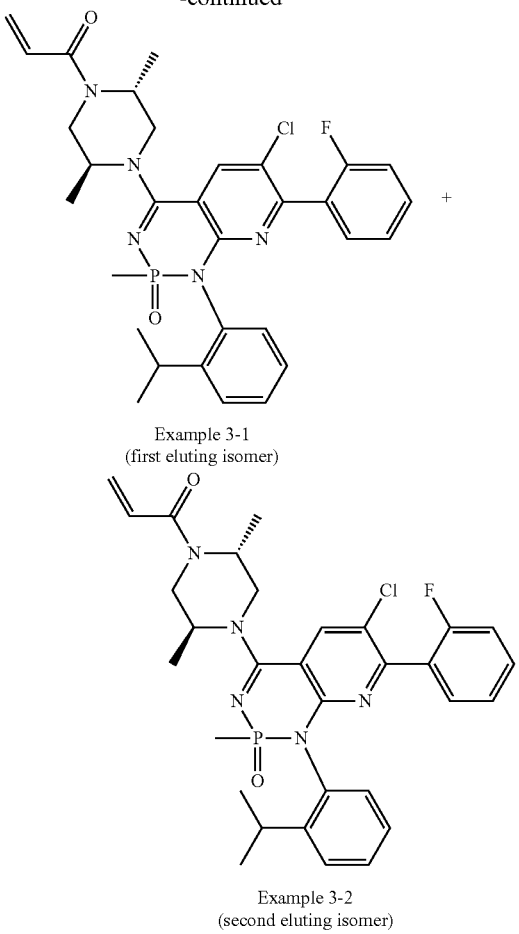

Example 3-1
(first eluting isomer)

Example 3-2
(second eluting isomer)

Steps 1-2: tert-Butyl (2R,5S)-4-(6-chloro-7-(2-fluorophenyl)-1-(2-isopropylphenyl)-2-methyl-2-oxido-1H-pyrido[2,3-d][1,3,2]diazaphosphinin-4-yl)-2,5-dimethylpiperazine-1-carboxylate A solution of methylphosphonic dichloride (0.20 g, 1.50 mmol) in THF (3 mL) was added to a solution of tert-butyl (2R,5S)-4-((2,5-dichloro-6-(2-fluorophenyl)pyridin-3-yl)(imino)methyl)-2,5-dimethylpiperazine-1-carboxylate (Intermediate 3, 0.65 g, 1.35 mmol) in THF (10 mL). The reaction mixture was stirred at r.t. for 30 min and DIPEA (0.70 mL, 4.05 mmol) and 2-isopropylaniline (0.21 mL, 1.48 mmol) were added. The reaction mixture was heated to 90° C. for 12 h then cooled to r.t., diluted with water, and extracted with EtOAc. The organic layer was dried over MgSO$_4$ and concentrated under reduced pressure. The crude residue was redissolved in DMF (5 mL) and cesium carbonate (1.32 g, 4.05 mmol) was added and the mixture was heated to 90° C. for 6 h. The reaction mixture was quenched with water and extracted with EtOAc (2x). The combined organic layers were concentrated and the residue was purified by chromatography on silica gel using 0-60% EtOAc/EtOH (3:1) in heptane to provide tert-butyl (2R,5S)-4-(6-chloro-7-(2-fluorophenyl)-1-(2-isopropylphenyl)-2-methyl-2-oxido-1H-pyrido[2,3-d][1,3,2]diazaphosphinin-4-yl)-2,5-dimethylpiperazine-1-carboxylate (0.43 g, 0.67 mmol, 49.7% yield). m/z (ESI, +ve ion): 640.2 (M+H)$^+$.

Step 3: 1-((2R,5S)-4-(6-Chloro-7-(2-fluorophenyl)-1-(2-isopropylphenyl)-2-methyl-2-oxido-1,2-dihydropyrido [2,3-d][1,3,2]diazaphosphinin-4-yl)-2,5-dimethylpiperazin-1-yl)prop-2-en-1-one (Example 3)

TFA (0.05 mL, 0.67 mmol) was added to a solution of tert-butyl (2R,5S)-4-(6-chloro-7-(2-fluorophenyl)-1-(2-isopropylphenyl)-2-methyl-2-oxido-1H-pyrido[2,3-d][1,3,2]diazaphosphinin-4-yl)-2,5-dimethylpiperazine-1-carboxylate (0.43 g, 0.67 mmol) in DCM (5 mL). The resulting mixture was stirred at r.t. for 1 h then concentrated under reduced pressure. The residue was suspended in DCM (5 mL), cooled to 0° C., and treated with DIPEA (0.47 mL, 2.69 mmol), followed by acryloyl chloride (0.09 mL, 1.07 mmol). The reaction was warmed to r.t. and stirred for 10 min. The mixture was quenched with water and extracted with DCM (2x). The combined organics were concentrated and the residue was purified by chromatography on silica gel using 0-80% EtOAc/EtOH (3:1) in heptane to provide 1-((2R,5S)-4-(6-chloro-7-(2-fluorophenyl)-1-(2-isopropylphenyl)-2-methyl-2-oxido-1,2-dihydropyrido[2,3-d][1,3,2]diazaphosphinin-4-yl)-2,5-dimethylpiperazin-1-yl)prop-2-en-1-one (Example 3, 0.20 g, 0.34 mmol, 5.6% yield) as a mixture of 2 isomers. m/z (ESI, +ve ion): 594.2 (M+H)$^+$.

Step 4: 1-((2R,5S)-4-(6-Chloro-7-(2-fluorophenyl)-1-(2-isopropylphenyl)-2-methyl-2-oxido-1H-pyrido [2,3-d][1,3,2]diazaphosphinin-4-yl)-2,5-dimethylpiperazin-1-yl)prop-2-en-1-one First Eluting Isomer (Example 3-1) and Second Eluting Isomer (Example 3-2)

A mixture of isomers of 1-((2R,5S)-4-(6-chloro-7-(2-fluorophenyl)-1-(2-isopropylphenyl)-2-methyl-2-oxido-1,2-dihydropyrido[2,3-d][1,3,2]diazaphosphinin-4-yl)-2,5-dimethylpiperazin-1-yl)prop-2-en-1-one (Example 3, 185 mg) was purified by preparative SFC using an OX—H column 21x250 mm, 5 µm, a mobile phase of 20% methanol with 0.2% TEA 80 mL/min to generate 25 mg of the first eluting isomer of (1-((2R,5S)-4-(6-chloro-7-(2-fluorophenyl)-1-(2-isopropylphenyl)-2-methyl-2-oxido-1H-pyrido[2,3-d][1,3,2]diazaphosphinin-4-yl)-2,5-dimethylpiperazin-1-yl)prop-2-en-1-one (Example 3-1), with purity of >95.0% and D.E.>95.0%, and 19 mg of the second eluting isomer of (1-((2R,5S)-4-(6-chloro-7-(2-fluorophenyl)-1-(2-isopropylphenyl)-2-methyl-2-oxido-1H-pyrido[2,3-d][1,3,2]diazaphosphinin-4-yl)-2,5-dimethylpiperazin-1-yl)prop-2-en-1-one (Example 3-2) with purity of 95.0% and D.E.>95.0%. D.E. determination by SFC: Chiralpak IC, 15% methanol.

First Eluting Isomer (Example 3-1)

$^1$H NMR (400 MHz, CD$_2$Cl$_2$) δ 7.71-7.93 (m, 1H), 7.49 (br d, J=7.67 Hz, 1H), 7.25-7.35 (m, 3H), 6.98-7.22 (m, 4H), 6.44-6.62 (m, 1H), 6.15-6.25 (m, 1H), 5.61-5.69 (m, 1H), 4.58-5.05 (m, 1H), 4.05-4.54 (m, 2H), 3.32-3.92 (m, 3H), 2.69-3.19 (m, 1H), 1.35-1.49 (m, 6H), 1.06 (d, J=6.84 Hz, 6H), 0.82-0.91 (m, 3H). $^{19}$F NMR (376 MHz, CD$_2$Cl$_2$) δ −113.52 (s, 1F). $^{31}$P NMR (162 MHz, CD$_2$Cl$_2$) δ 19.89 (s, 1P). m/z (ESI, +ve ion): 594.2 (M+H)$^+$.

Second Eluting Isomer (Example 3-2)

$^1$H NMR (400 MHz, CD$_2$Cl$_2$) δ 7.93 (d, J=11.82 Hz, 1H), 7.65 (d, J=7.44 Hz, 1H), 7.38-7.47 (m, 3H), 7.11-7.36 (m, 4H), 6.56-6.71 (m, 1H), 6.32 (br t J=14.93 Hz, 1H), 5.76 (br d, J=10.57 Hz, 1H), 4.69-5.07 (m, 2H), 4.23-4.37 (m, 1H), 3.52-4.05 (m, 3H), 2.81 (qd, J=6.84, 13.68 Hz, 1H), 1.49-1.59 (m, 3H), 1.21-1.47 (m, 6H), 1.13-1.16 (m, 3H), 0.95 (d, J=6.84 Hz, 3H). $^{19}$F NMR (376 MHz, CD$_2$Cl$_2$) δ −113.53 (s, 1F). $^{31}$P NMR (162 MHz, CD$_2$Cl$_2$) δ 20.27 (s, 1P). m/z (ESI, +ve ion): 594.2 (M+H)$^+$.

TABLE 1

Separated Compound Examples, including isomers and some atropisomers

| Ex.# | Chemical Structure | Name | Racemic SM/ separation conditions |
|---|---|---|---|
| 4-1 | 1$^{st}$-eluting isomer | 1-((2R,5S)-4-(1-(2-(tert-butyl)phenyl)-6-chloro-7-(2-fluorophenyl)-2-methyl-2-oxido-1H-pyrido[2,3-d][1,3,2]diazaphosphinin-4-yl)-2,5-dimethylpiperazin-1-yl)prop-2-en-1-one | SFC Step 1: OD-H, 21 x 250 mm, 5 μm, 20% MeOH/CO$_2$, 64 g/min, 128 bar. Step 2: (separation of peaks 2 and 3) OX-H, 21 x 250 mm, 5 μm, 25% MeOH/CO$_2$, 60 g/min, 105 bar |
| 4-2 | 2$^{nd}$-eluting isomer | 1-((2R,5S)-4-(1-(2-(tert-butyl)phenyl)-6-chloro-7-(2-fluorophenyl)-2-methyl-2-oxido-1H-pyrido[2,3-d][1,3,2]diazaphosphinin-4-yl)-2,5-dimethylpiperain-1-yl)prop-2-en-1-one | SFC Step 1: OD-H, 21 x 250 mm, 5 μm, 20% MeOH/CO$_2$, 64 g/min, 128 bar. Step 2: (separation of peaks 2 and 3) OX-H, 21 x 250 mm, 5 μm, 25% MeOH/CO$_2$, 60 g/min, 105 bar |
| 4-3 | 3$^{rd}$-eluting isomer | 1-((2R,5S)-4-(1-(2-(tert-butyl)phenyl)-6-chloro-7-(2-fluorophenyl)-2-methyl-2-oxido-1H-pyrido[2,3-d][1,3,2]diazaphosphinin-4-yl)-2,5-dimethylpiperain-1-yl)prop-2-en-1-one | SFC Step 1: OD-H, 21 x 250 mm, 5 μm, 20% MeOH/CO$_2$, 64 g/min, 128 bar. Step 2: (separation of peaks 2 and 3) OX-H, 21 x 250 mm, 5 μm, 25% MeOH/CO$_2$, 60 g/min, 105 bar |

TABLE 1-continued

Separated Compound Examples, including isomers and some atropisomers

| Ex.# | Chemical Structure | Name | Racemic SM/ separation conditions |
|---|---|---|---|
| 4-4 | 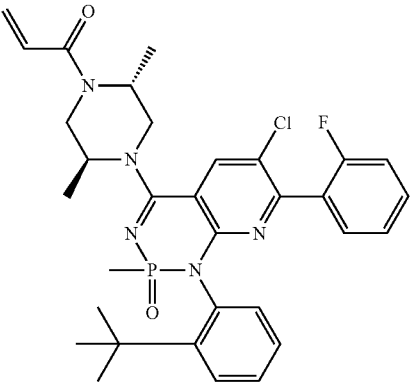<br>4th-eluting isomer | 1-((2R,5S)-4-(1-(2-(tert-butyl)phenyl)-6-chloro-7-(2-fluorophenyl)-2-methyl-2-oxido-1H-pyrido[2,3-d][1,3,2]diazaphosphinin-4-yl)-2,5-dimethylpiperain-1-yl)prop-2-en-1-one | SFC Step 1: OD-H, 21 x 250 mm, 5 μm, 20% MeOH/CO$_2$, 64 g/min, 128 bar. Step 2: (separation of peaks 2 and 3) OX-H, 21 x 250 mm, 5 μm, 25% MeOH/CO$_2$, 60 g/min, 105 bar |
| 5-1 | 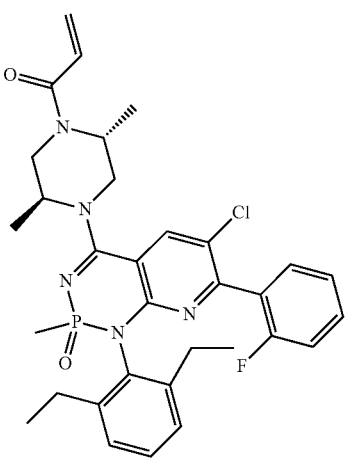<br>1st-eluting isomer | 1-((2R,5S)-4-(6-chloro-1-(2,6-diethylphenyl)-7-(2-fluorophenyl)-2-methyl-2-oxido-1H-pyrido[2,3-d][1,3,2]diazaphospinin-4-yl)-2,5-dimethylpiperazin-1-yl)prop-2-en-1-one | SFC OX-H, 21 x 250 mm, 5 μm, 30% MeOH/CO$_2$, 56 g/min, 106 bar |
| 5-2 | 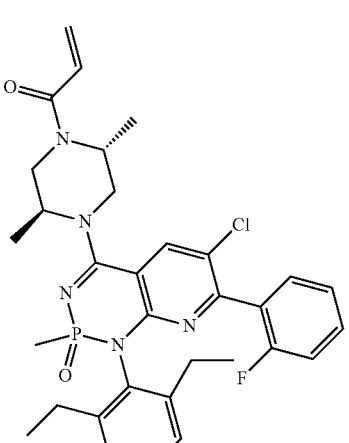<br>2nd-eluting isomer | 1-((2R,5S)-4-(6-chloro-1-(2,6-diethylphenyl)-7-(2-fluorophenyl)-2-methyl-2-oxido-1H-pyrido[2,3-d][1,3,2]diazaphospinin-4-yl)-2,5-dimethylpiperazin-1-yl)prop-2-en-1-one | SFC OX-H, 21 x 250 mm, 5 μm, 30% MeOH/CO$_2$, 56 g/min, 106 bar |

TABLE 1-continued

Separated Compound Examples, including isomers and some atropisomers

| Ex.# | Chemical Structure | Name | Racemic SM/ separation conditions |
|---|---|---|---|
| 6-1 | 1st-eluting isomer | 1-((2R,5S)-4-(6-chloro-7-(2-fluorophenyl)-1-(4-isopropylthiazol-5-yl)-2-methyl-2-oxido-1H-pyrido[2,3-d][1,3,2]diazaphosphinin-4-yl)-2,5-dimethylpiperazin-1-yl)prop-2-en-1-one | SFC OX-H, 21 x 250 mm, 5 μm, 40% MeOH/CO$_2$, 48 g/min, 109 bar |
| 6-2 | 2nd-eluting isomer | 1-((2R,5S)-4-(6-chloro-7-(2-fluorophenyl)-1-(4-isopropylthiazol-5-yl)-2-methyl-2-oxido-1H-pyrido[2,3-d][1,3,2]diazaphosphinin-4-yl)-2,5-dimethylpiperazin-1-yl)prop-2-en-1-one | SFC OX-H, 21 x 250 mm, 5 μm, 40% MeOH/CO$_2$, 48 g/min, 109 bar |
| 7-1 | 1st-eluting isomer | 1-((2R,5S)-4-(6-chloro-7-(2-fluorophenyl)-1-(2-isopropyl-4-methylpyridin-3-yl)-2-methyl-2-oxido-1H-pyrido[2,3-d][1,3,2]diazaphosphinin-4-yl)-2,5-dimethylpiperazin-1-yl)prop-2-en-1-one | SFC OX-H, 21 x 250 mm, 5 μm, 40% MeOH/CO$_2$, 70 g/min, 102 bar |

TABLE 1-continued

Separated Compound Examples, including isomers and some atropisomers

| Ex.# | Chemical Structure | Name | Racemic SM/ separation conditions |
|---|---|---|---|
| 7-2 | 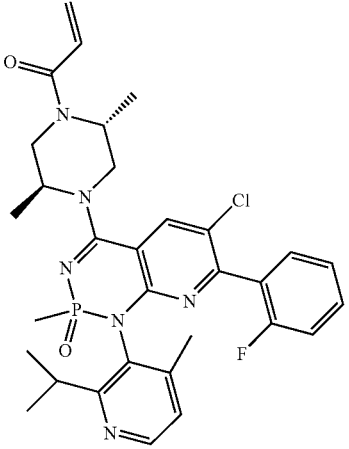<br>2nd-eluting isomer | 1-((2R,5S)-4-(6-chloro-7-(2-fluorophenyl)-1-(2-isopropyl-4-methylpyridin-3-yl)-2-methyl-2-oxido-1H-pyrido[2,3-d][1,3,2]diazaphosphinin-4-yl)-2,5-dimethylpiperazin-1-yl)prop-2-en-1-one | SFC OX-H, 21 × 250 mm, 5 μm, 40% MeOH/CO$_2$, 70 g/min, 102 bar |
| 7-3 | 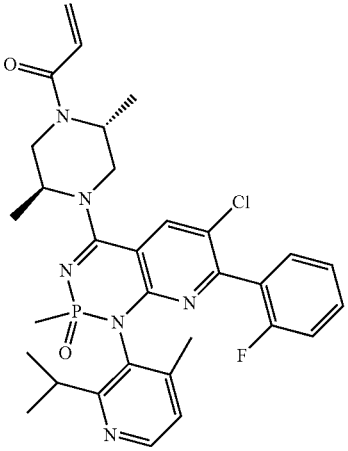<br>3rd-eluting isomer<br>(mixture of 2 isomers) | 1-((2R,5S)-4-(6-chloro-7-(2-fluorophenyl)-1-(2-isopropyl-4-methylpyridin-3-yl)-2-methyl-2-oxido-1H-pyrido[2,3-d][1,3,2]diazaphosphinin-4-yl)-2,5-dimethylpiperazin-1-yl)prop-2-en-1-one | SFC OX-H, 21 × 250 mm, 5 μm, 40% MeOH/CO$_2$, 70 g/min, 102 bar |

TABLE 2

The compounds, isomers and some atropisomers, in the table were prepared following the procedure described in Method 3, Steps 1-4 above as follows:

| Ex..# | Chemical Structure | Name | Reagents | |
|---|---|---|---|---|
| 4 | Obtained as a mixture of 4-isomers | 1-((2R,5S)-4-(1-(2-(tert-butyl)phenyl)-6-chloro-7-(2-fluorophenyl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 2-tert-butylaniline (Sigma-Aldrich, St. Louis, MO) | $^1$H NMR (400 MHz, CDCl$_3$) δ 7.72-7.85 (m, 1H), 7.67 (d, J = 6.83 Hz, 1H), 7.48 (dd, J = 2.07, 7.46 Hz, 1H), 7.24-7.36 (m, 3H), 7.15-7.22 (m, 1H), 7.00-7.11 (m, 2H), 6.49-6.65 (m, 1H), 6.30-6.41 (m, 1H), 5.72-5.80 (m, 1H), 4.92 (br s, 1H), 4.19-4.46 (m, 1H), 3.43-3.98 (m, 4H), 1.64 (d, J = 16.38 Hz, 3H), 1.20-1.32 (m, 6H), 1.17 (d, J = 2.70 Hz, 9H). $^{19}$F NMR (376 MHz, CDCl$_3$) δ −112.36 (s, 1F). $^{31}$P NMR (162 MHz, CDCl$_3$) δ 24.88 (q, J = 16.95 Hz, 1P). m/z (ESI, +ve ion): 608.2 (M + H)$^+$. |
| 4-1 | 1$^{st}$-eluting isomer | 1-((2R,5S)-4-(1-(2-(tert-butyl)phenyl)-6-chloro-7-(2-fluorophenyl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 2-tert-butylaniline (Sigma-Aldrich, St. Louis, MO) | $^1$H NMR (400 MHz, CD$_2$Cl$_2$) δ 7.83-8.04 (m, 1H), 7.55-7.68 (m, 2H), 7.27-7.47 (m, 4H), 7.11-7.23 (m, 2H), 6.51-6.79 (m, 1H), 6.32 (br dd, J = 12.54, 16.69 Hz, 1H), 5.74-5.82 (m, 1H), 5.35-5.37 (m, 0.5H), 5.03-5.10 (m, 0.5H), 4.25-4.66 (m, 3H), 3.71 (br d, J = 14.10 Hz, 0.5H), 3.45-3.56 (m, 1H), 3.01 (br dd, J = 3.21, 13.58 Hz, 0.5H), 1.48-1.60 (m, 6H), 1.46 (br dd, J = 3.21, 6.32 Hz, 3H), 1.23 (d, J = 3.73 Hz, 9H). $^{19}$F NMR (376 MHz, CD$_2$Cl$_2$) δ −113.35 (s, 1F). $^{31}$P NMR (162 MHz, CD$_2$Cl$_2$) δ 23.03 (s, 1P), 22.99 (s, 1P). m/z (ESI, +ve ion): 608.3 (M + H)$^+$. |

TABLE 2-continued

The compounds, isomers and some atropisomers, in the table were prepared following the procedure described in Method 3, Steps 1-4 above as follows:

| Ex..# | Chemical Structure | Name | Reagents | |
|---|---|---|---|---|
| 4-2 | 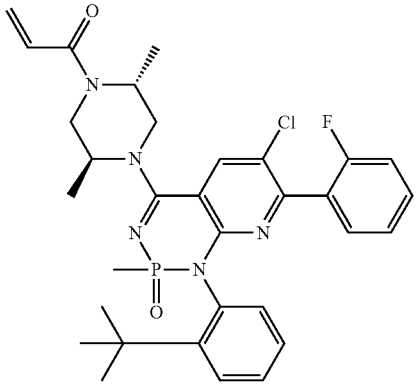<br>2nd-eluting isomer | 1-((2R,5S)-4-(1-(2-(tert-butyl)phenyl)-6-chloro-7-(2-fluorophenyl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 2-tert-butylaniline (Sigma-Aldrich, St. Louis, MO) | $^1$H NMR (400 MHz, CD$_2$Cl$_2$) δ 7.89-7.98 (m, 1H), 7.66 (d, J = 7.46 Hz, 1H), 7.59 (d, J = 7.79 Hz, 1H), 7.25-7.47 (m, 4H), 7.11-7.22 (m, 2H), 6.57-6.72 (m, 1H), 6.28-6.38 (m, 1H), 5.74-5.81 (m, 1H), 4.88 (br s, 1H), 4.31 (br d, J = 10.78 Hz, 1H), 3.52-4.03 (m, 4H), 1.62 (d, J = 16.38 Hz, 3H), 1.18-1.39 (m, 15H). $^{19}$F NMR (376 MHz, CD$_2$Cl$_2$) δ −113.22 (s, 1F). $^{31}$P NMR (162 MHz, CD$_2$Cl$_2$) δ 24.04 (s, 1P), 23.93 (s, 1P). mz (ESI, +ve ion): 608.3 (M + H)$^+$. |
| 4-3 | 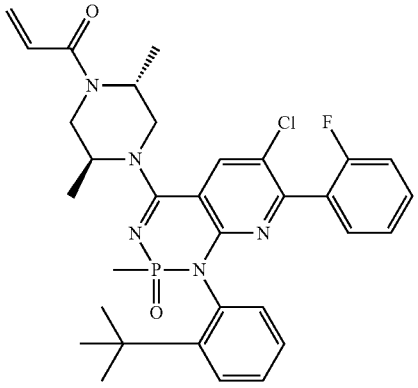<br>3rd-eluting isomer | 1-((2R,5S)-4-(1-(2-(tert-butyl)phenyl)-6-chloro-7-(2-fluorophenyl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 2-tert-butylaniline (Sigma-Aldrich, St. Louis, MO) | $^1$H NMR (400 MHz, CD$_2$Cl$_2$) δ 7.80-7.94 (m, 1H), 7.63 (dd, J = 1.55, 7.98 Hz, 1H), 7.41-7.51 (m, 1H), 7.13-7.38 (m, 5H), 7.07 (br d, J = 7.67 Hz, 1H), 6.50-6.80 (m, 1H), 6.33 (br dd, J = 9.64, 16.69 Hz, 1H), 5.74-5.82 (m, 1H), 5.02-5.10 (m, 0.5H), 4.18-4.63 (m, 3H), 3.44-3.78 (m, 2H), 3.08 (br dd, J = 3.11, 13.89 Hz, 0.5H), 1.46-1.60 (m, 9H), 1.37 (d, J = 2.90 Hz, 9H). $^{19}$F NMR (376 MHz, CD$_2$Cl$_2$) δ −112.77 (s, 1F). $^{31}$P NMR (162 MHz, CD$_2$Cl$_2$) δ 22.92 (s, 1P), 22.78 (s, 1P). m/z (ESI, +ve ion): 608.3 (M + H)$^+$. |

TABLE 2-continued

The compounds, isomers and some atropisomers, in the table were prepared following the procedure described in Method 3, Steps 1-4 above as follows:

| Ex..# | Chemical Structure | Name | Reagents | |
|---|---|---|---|---|
| 4-4 | 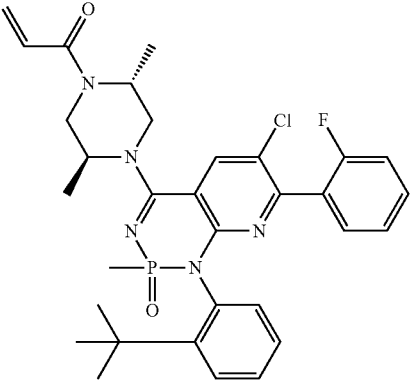<br>4th-eluting isomer | 1-((2R,5S)-4-(1-(2-(tert-butyl)phenyl)-6-chloro-7-(2-fluorophenyl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 2-tert-butylaniline (Sigma-Aldrich, St. Louis, MO) | $^1$H NMR (400 MHz, CD$_2$Cl$_2$) δ 7.77-7.92 (m, 1H), 7.63 (dd, J = 1.45, 8.09 Hz, 1H), 7.26-7.49 (m, 4H), 7.19-7.24 (m, 1H), 7.15 (t, J = 9.10 Hz, 1H), 7.06 (d, J = 7.67 Hz, 1H), 6.55-6.72 (m, 1H), 6.33 (br t, J = 16.48 Hz, 1H), 5.72-5.83 (m, 1H), 5.00 (br s, 0.5H), 4.87 (br s, 1H), 4.16-4.37 (m, 1H), 3.85-4.03 (m, 1.5H), 3.61-3.84 (m, 2H), 1.60 (d, J = 14.72 Hz, 3H), 1.37 (s, 15H). $^{19}$F NMR (376 MHz, CD$_2$Cl$_2$) δ −112.64 (s, 1F). $^{31}$P NMR (162 MHz, CD$_2$Cl$_2$) δ 23.68 (s, 1P), 23.53 (s, 1P). m/z (ESI, +ve ion): 608.3 (M + H)$^+$. |
| 5 | 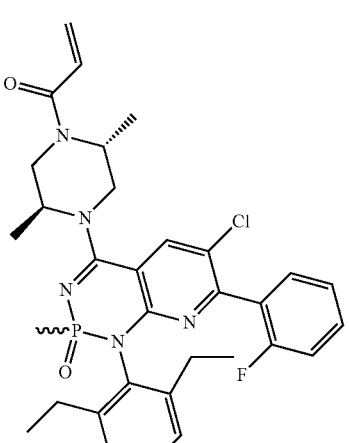<br>Obtained as a mixture of 2 isomers | 1-((2R,5S)-4-(6-chloro-1-(2,6-diethylphenyl)-7-(2-fluorophenyl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 2,6-diethylaniline (Sigma-Aldrich; St. Louis, MO); Step 2: omit | |

TABLE 2-continued

The compounds, isomers and some atropisomers, in the table were prepared following the procedure described in Method 3, Steps 1-4 above as follows:

| Ex..# | Chemical Structure | Name | Reagents | |
|---|---|---|---|---|
| 5-1 | 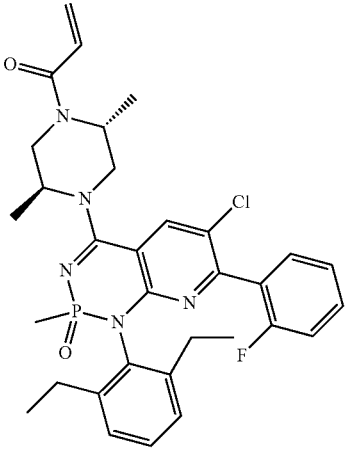<br>1st-eluting isomer | 1-((2R,5S)-4-(6-chloro-1-(2,6-diethylphenyl)-7-(2-fluorophenyl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 2,6-diethylaniline (Sigma-Aldrich; St. Louis, MO); Step 2: omit | $^1$H NMR (400 MHz, CDCl$_3$) δ 7.77-7.89 (m, 1H), 7.31-7.41 (m, 1H), 7.22-7.27 (m, 3H), 7.01-7.18 (m, 3H), 6.48-6.68 (m, 1H), 6.37 (br t, J = 15.13 Hz, 1H), 5.70-5.83 (m, 1H), 4.73-4.95 (m, 1H), 4.18-4.41 (m, 1H), 3.54-3.97 (m, 3H), 2.82-3.04 (m, 2H), 2.2-2.39 (m, 2H), 1.48 (d, J = 16.4 Hz, 3H), 1.30-1.31-1.34 (m, 3H), 1.13-1.28 (m, 6H), 0.85-0.92 (m, 3H).<br><br>$^{19}$F NMR (376 MHz, CDCl$_3$) δ −112.73- −112.79 (d, 1F, J = 2.4 Hz). |
| 5-2 | 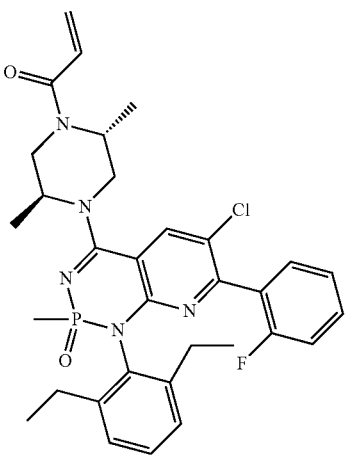<br>2nd-eluting isomer | 1-((2R,5S)-4-(6-chloro-1-(2,6-diethylphenyl)-7-(2-fluorophenyl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 2,6-diethylaniline (Sigma-Aldrich; St. Louis, MO); Step 2: omit | $^1$H NMR (400 MHz, CDCl$_3$) δ 7.87 (d, J = 14.10 Hz, 1H), 7.30-7.42 (m, 1H), 7.19-7.25 (m, 3H), 6.99-7.17 (m, 3H), 6.47-6.67 (m, 1H), 6.28-6.47 (m, 1H), 5.65-5.84 (m, 1H), 5.06 (br d, J = 5.18 Hz, 1H), 4.58-5.11 (m, 1H), 4.03-4.57 (m, 2H), 3.50-3.71 (m, 2H), 2.74-3.01 (m, 2H), 2.21-2.43 (m, 2H), 1.41-1.50 (m 9H), 1.20 (br d, J 6.8 Hz, 3H), 0.96 (td, J = 7.5, 3.0 Hz, 3H).<br><br>$^{19}$F NMR (377 MHz, CDCl$_3$) δ −112.65 (br d, J = 4.33 Hz, 1F). |

TABLE 2-continued

The compounds, isomers and some atropisomers, in the table were prepared following the procedure described in Method 3, Steps 1-4 above as follows:

| Ex..# | Chemical Structure | Name | Reagents | |
|---|---|---|---|---|
| 6 | 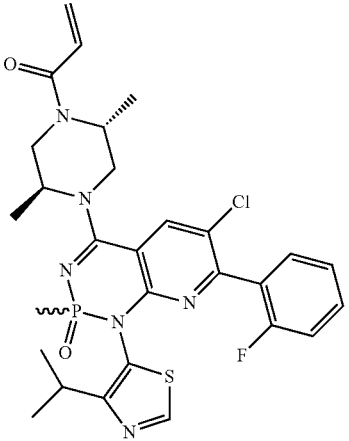<br>Obtained as a mixture of 2 isomers | 1-((2R,5S)-4-(6-chloro-7-(2-fluorophenyl)-1-(4-isopropylthiazol-5-yl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 4-(propan-2-yl)-1,3-thiazol-5-amine (Enamine); Step 2: omit | |
| 6-1 | 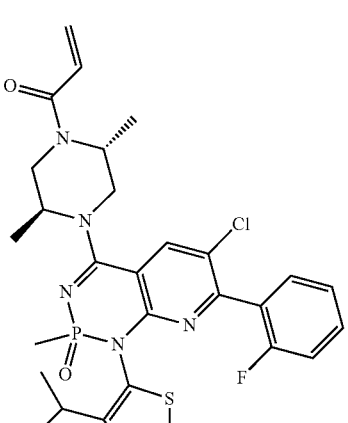<br>1st-eluting isomer | 1-((2R,5S)-4-(6-chloro-7-(2-fluorophenyl)-1-(4-isopropylthiazol-5-yl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 4-(propan-2-yl)-1,3-thiazol-5-amine (Enamine); Step 2: omit | $^1$H NMR (CDCl$_3$) δ: 8.64-8.86 (m, 1H), 7.75-7.88 (m, 1H), 7.36-7.48 (m, 1H), 7.27-7.34 (m, 1H), 7.06-7.22 (m, 2H), 6.48-6.67 (m, 1H), 6.38 (br t, J = 15.8 Hz, 1H), 5.79 (br dd, J = 10.2, 3.7 Hz, 1H), 4.70-5.07 (m, 1H), 4.19-4.44 (m, 1H), 3.43-3.97 (m, 4H), 2.68-2.83 (m, 1H), 1.71 (d, J = 16.4 Hz, 3H), 1.36 (br t, J = 6.1 Hz, 3H), 1.24 (d, J = 6.8 Hz, 3H), 1.12-1.17 (m, 3H), 1.00 (d, J = 6.8 Hz, 3H). $^{19}$F NMR (CDCl$_3$) δ: −112.35- −112.17 (m, 1F). |

TABLE 2-continued

The compounds, isomers and some atropisomers, in the table were prepared following the procedure described in Method 3, Steps 1-4 above as follows:

| Ex..# | Chemical Structure | Name | Reagents | |
|---|---|---|---|---|
| 6-2 | 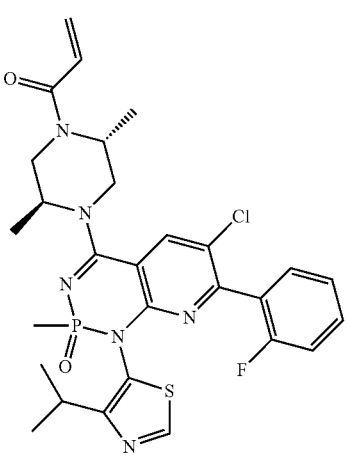<br>2nd-eluting isomer | 1-((2R,5S)-4-(6-chloro-7-(2-fluorophenyl)-1-(4-isopropylthiazol-5-yl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 4-(propan-2-yl)-1,3-thiazol-5-amine (Enamine); Step 2: omit | $^1$H NMR (CDCl$_3$) δ: 8.74-8.80 (m, 1H), 7.81-7.98 (m, 1H), 7.37-7.47 (m, 1H), 7.27-7.36 (m, 1H), 7.04-7.22 (m, 2H), 6.46-6.71 (m, 1H), 6.28-6.46 (m, 1H), 5.72-5.85 (m, 1H), 4.15-5.14 (m, 3H), 3.44-3.94 (m, 2H), 3.07-3.41 (m, 1H), 2.85 (quin, J = 6.8 Hz, 1H), 1.61-1.74 (m, 3H), 1.38-1.54 (m, 6H), 1.23-1.29 (m, 3H), 1.01-1.11 (m, 3H). $^{19}$F NMR (CDCl$_3$) δ: −112.40 (d, J = 7.8 Hz, 1F). |
| 7 | 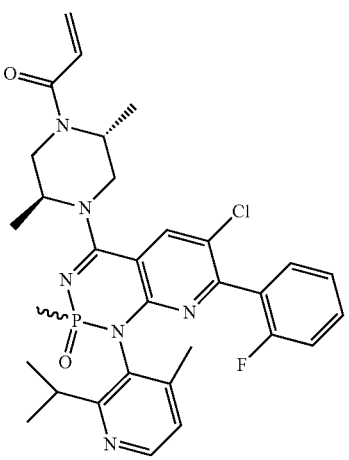<br>Obtained as a mixture of 4 isomers | 1-((2R,5S)-4-(6-chloro-7-(2-fluorophenyl)-1-(2-isopropyl-4-methylpyridin-3-yl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 4-(2-isopropyl-4-methylpyridin-3-amine (Syngene); Step 2: omit | |

TABLE 2-continued

The compounds, isomers and some atropisomers, in the table were prepared following the procedure described in Method 3, Steps 1-4 above as follows:

| Ex..# | Chemical Structure | Name | Reagents | |
|---|---|---|---|---|
| 7-1 | 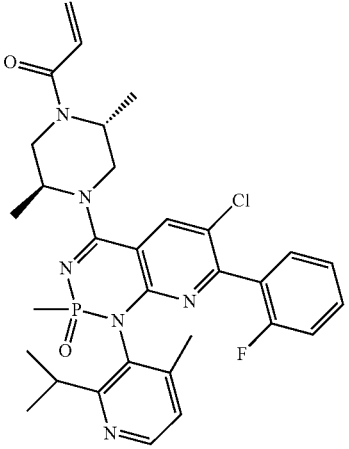<br>1st-eluting isomer | 1-((2R,5S)-4-(6-chloro-7-(2-fluorophenyl)-1-(2-isopropyl-4-methylpyridin-3-yl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 4-(2-isopropyl-4-methylpyridin-3-amine (Syngene); Step 2: omit | $^1$H NMR (CDCl$_3$) δ: 8.53 (d, J = 4.8 Hz, 1H), 7.85-7.97 (m, 1H), 7.36-7.48 (m, 1H), 7.27 (br s, 1H), 7.01-7.24 (m, 3H), 6.53-6.74 (m, 1H), 6.42 (br t, J = 15.4 Hz, 1H), 5.82 (br dd, J = 10.4, 5.0 Hz, 1H), 4.66-5.05 (m, 1H), 4.65-4.80 (m, 1H), 4.25-4.45 (m, 1H), 3.50-4.00 (m, 5H), 2.04 (s, 3H), 1.56 (d, J = 16.2 Hz, 3H), 1.42 (d, J = 6.6 Hz, 3H), 1.21-1.40 (m, 6H), 1.17 (d, J = 6.8 Hz, 3H). $^{19}$F NMR (CDCl$_3$) δ: −113.37−−113.02 (m, 1F). |
| 7-2 | 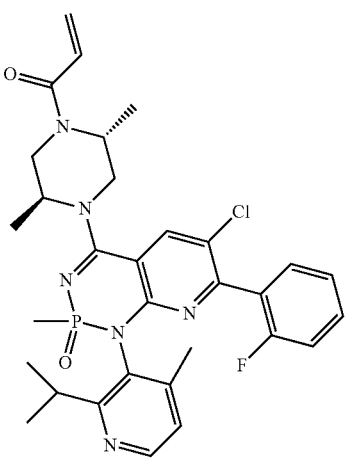<br>2nd-eluting isomer | 1-((2R,5S)-4-(6-chloro-7-(2-fluorophenyl)-1-(2-isopropyl-4-methylpyridin-3-yl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 4-(2-isopropyl-4-methylpyridin-3-amine (Syngene); Step 2: omit | $^1$H NMR (CDCl$_3$) δ: 8.47 (d, J = 5.0 Hz, 1H), 7.97 (d, J = 16.6 Hz, 1H), 7.39-7.52 (m, 1H), 7.10-7.29 (m, 3H), 6.54-6.78 (m, 1H), 6.33-6.51 (m, 1H), 5.85 (br t, J = 9.2 Hz, 1H), 3.18-5.15 (m, 6H), 2.90-3.04 (m, 1H), 2.51 (d, J = 9.7 Hz, 3H), 1.52-1.66 (m, 9H), 1.27-1.38 (m, 3H), 0.82-0.95 (m, 3H). $^{19}$F NMR (CDCl$_3$) δ: −112.93 (br d, J = 15.6 Hz, 1F). |

TABLE 2-continued

The compounds, isomers and some atropisomers, in the table were prepared following the procedure described in Method 3, Steps 1-4 above as follows:

| Ex..# | Chemical Structure | Name | Reagents | $^1$H NMR |
|---|---|---|---|---|
| 7-3 | 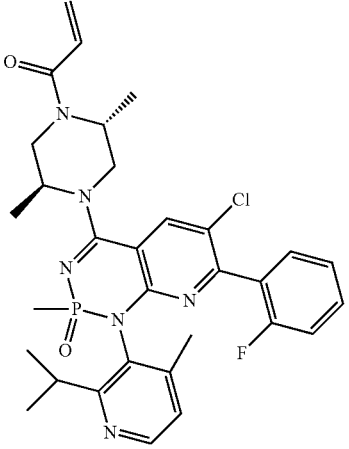<br>3$^{rd}$-eluting isomer<br>(mixture of 2-isomers) | 1-((2R,5S)-4-(6-chloro-7-(2-fluorophenyl)-1-(2-isopropyl-4-methylpyridin-3-yl)-2-methyl-2-oxido-1H-pyrido[2,3-d][1,3,2]diazaphosphinin-4-yl)-2,5-dimethylpiperazin-1-yl)prop-2-en-1-one | Method 3 Step 1: 4-(2-isopropyl-4-methylpyridin-3-amine (Syngene); Step 2: omit | $^1$H NMR (CDCl$_3$) δ: 8.46 (d, J = 4.8 Hz, 1H), 7.91 (d, J = 4.1 Hz, 1H), 7.37-7.47 (m, 1H), 6.98-7.24 (m, 3H), 6.51-6.74 (m, 1H), 6.41 (br t, J = 15.3 Hz, 1H), 5.8 (br t, J = 8.6 Hz, 1H), 3.24-5.15 (m, 7H), 2.10 (d, J = 5.8 Hz, 3H), 1.47-1.49 (m, 3H), 1.45-1.47 (m, 3H), 1.38-1.42 (m, 3H), 1.07 (br dd, J = 12.6, 6.6 Hz, 3H). $^{19}$F NMR (CDCl$_3$) δ: −112.98 (br d, J = 7.8 Hz, 1F). |

Biological Analysis

For compounds in Table 3, in which a mixture of atropisomers and phosphorus isomers are listed, the following assay conditions were employed:

Coupled Nucleotide Exchange Assay: Purified GDP-bound KRAS protein (aa 1-169), containing both G12C and C$_{118}$A amino acid substitutions and an N-terminal His-tag, was pre-incubated in assay buffer (25 mM HEPES pH 7.4, 10 mM MgCl$_2$, and 0.01% Triton X-100) with a compound dose-response titration for either 5 min or 2 hours (see Table 15). Following compound pre-incubation, purified SOS protein (aa 564-1049) and GTP (Roche 10106399001) were added to the assay wells and incubated for an additional 30 min (for 5 min compound pre-incubation) or 1 hour (for 2 hour compound pre-incubation). To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 10 minutes. The assay plates were then read on a PerkinElmer EnVision Multilabel Reader, using AlphaScreen® technology, and data were analyzed using a 4-parameter logistic model to calculate IC$_{50}$ values.

Phospho-ERK1/2 MSD Assay: MIA PaCa-2 (ATCC® CRL-1420™)-cells were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, MIA PaCa-2 cells were seeded in 96-well cell culture plates at a density of 25,000 cells/well and incubated at 37° C., 5% CO$_2$. A compound dose-response titration was diluted in growth media, added to appropriate wells of a cell culture plate, and then incubated at 37° C., 5% CO$_2$ for 2 or 4 hours. Following compound treatment, cells were stimulated with 10 ng/mL EGF (Roche 11376454001) for 10 min, washed with ice-cold Dulbecco's phosphate-buffered saline, no Ca$^{2+}$ or Mg$^{2+}$ (ThermoFisher Scientific 14190144), and then lysed in RIPA buffer (50 mM Tris-HCl pH 7.5, 1% Igepal, 0.5% sodium deoxycholate, 150 mM NaCl, and 0.5% sodium dodecyl sulfate) containing protease inhibitors (Roche 4693132001) and phosphatase inhibitors (Roche 4906837001). Phosphorylation of ERK1/2 in compound-treated lysates was assayed using Phospho-ERK 1/2 Whole Cell Lysate kits (Meso Scale Discovery K 151DWD) according to the manufacturer's protocol. Assay plates were read on a Meso Scale Discovery Sector Imager 6000, and data were analyzed using a 4-parameter logistic model to calculate IC$_{50}$ values.

Viability CTG Assay MIA PaCa-2 (ATCC® CRL-1420™) cells were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, MIA PaCa-2 cells were seeded in 384-well cell culture plates at a density of 500 cells/well and incubated at 37° C., 5% CO$_2$. A compound dose-response titration was diluted in growth media, added to appropriate wells of a cell culture plate, and then assay plates were incubated at 37° C., 5% CO$_2$. After 72 hours of compound treatment, cell viability was measured using a CellTiter-Glo® Luminescent Cell Viability Assay kit (Promega G7571) according to the manufacturer's protocol. Assay plates were read on a Perkin Elmer EnVision® Multilabel Reader, and data were analyzed using a 4-parameter logistic model to calculate IC$_{50}$ values.

TABLE 3

| | Mixture of atropisomers and Phosphorus isomers | | |
|---|---|---|---|
| Ex# | Coupled Exchange (5 min, μM) | p-ERK (MiaPaCa-2, μM) | Viability CTG (MiaPaCa-2, μM) |
| 1 | 0.31 | 0.79 | 0.029 |
| 2 | 2.0 | — | — |
| 2-1 | 0.54 | — | — |
| 2-2 | 4.41 | — | — |
| 3 | 0.35 | — | — |
| 3-1 | 0.022 | 0.23 | 0.016 |
| 3-2 | 0.38 | — | — |
| 4 | 3.28 | — | — |
| 4-1 | 0.033 | 0.21 | 0.023 |
| 4-2 | NC | — | — |
| 4-3 | 0.21 | 0.20 | 0.023 |
| 4-4 | 2.3 | — | — |
| 5 | 2.09 | — | — |
| 5-1 | 3.9 | — | — |
| 5-2 | 0.98 | — | — |
| 6 | 0.11 | 0.11 | 0.006 |
| 6-1 | 0.54 | — | — |
| 6-2 | 0.10 | 0.070 | 0.005 |
| 7 | 0.39 | — | — |
| 7-1 | 0.31 | — | — |
| 7-2 | 0.082 | 0.061 | 0.006 |
| 7-3 | 2.52 | — | — |

(—) denotes not tested

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:
1. A compound having a structure of formula (I)

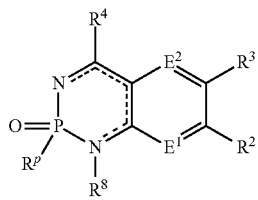

wherein
E$^1$ and E$^2$ are each independently N or CR$^1$;
⇌ is a single or double bond as necessary to give every atom its normal valence;
R$^p$ is independently H, hydroxy, —C$_{1-6}$alkyl, halo, —C$_{1-4}$haloalkyl, —C$_{1-4}$alkoxy, —NH—C$_{1-4}$alkyl, —N(C$_{1-4}$alkyl)$_2$, cyano, —C$_{2-3}$alkenyl, —C$_{2-3}$alkynyl, —C$_{3-14}$cycloalkyl, —C$_{2-14}$heterocycloalkyl, aryl, or heteroaryl;
R$^1$ is independently H, hydroxy, —C$_{1-6}$alkyl, —C$_{1-6}$haloalkyl, —C$_{1-6}$alkoxy, —NH—C$_{1-6}$alkyl, —N(C$_{1-4}$alkyl)$_2$, cyano, or halo;
R$^2$ is halo, —C$_{1-6}$alkyl, —C$_{1-6}$haloalkyl, —OR$^{2a}$, —N(R$^{2a}$)$_2$, —C$_{2-6}$alkenyl, —C$_{2-6}$alkynyl, —C$_{0-3}$alkylene-C$_{3-14}$cycloalkyl, —C$_{0-3}$alkylene-C$_{2-14}$heterocycloalkyl, aryl, heteroaryl, —C$_{0-3}$alkylene-C$_{6-14}$aryl, or —C$_{0-3}$alkylene-C$_{2-14}$heteroaryl, and each R$^{2a}$ is independently H, —C$_{1-6}$alkyl, —C$_{1-6}$haloalkyl, —C$_{3-14}$cycloalkyl, —C$_{2-14}$heterocycloalkyl, —C$_{2-6}$alkenyl, —C$_{2-6}$alkynyl, aryl, or heteroaryl, or two R$^{2a}$ substituents, together with the nitrogen atom to which they are attached, form a 3-7-membered ring;
R$^3$ is halo, —C$_{1-6}$alkyl, —C$_{1-6}$haloalkyl, —C$_{1-6}$alkoxy, C$_{3-6}$cycloalkyl, —C$_{2-14}$heterocycloalkyl, —C$_{2-6}$alkenyl, —C$_{2-6}$alkynyl, aryl, or heteroaryl;

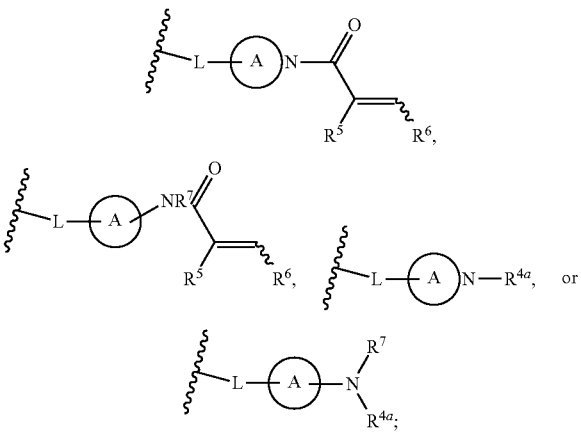

ring A is a monocyclic 4-7 membered ring or a bicyclic, bridged, fused, or spiro 6-11 membered ring;
L is a bond, —C$_{1-6}$alkylene, —O—C$_{0-6}$alkylene, —S—C$_{0-6}$alkylene, or —NH—C$_{0-6}$alkylene, and for —C$_{2-6}$alkylene, —O—C$_{2-6}$alkylene, —S—C$_{2-6}$alkylene, and NH—C$_{2-6}$ alkylene, one carbon atom of the alkylene group can optionally be replaced with O, S, or NH;
R$^{4a}$ is H, C$_{1-6}$alkyl, C$_{2-6}$alkynyl, C$_{1-6}$alkylene-O—C$_{1-4}$alkyl, C$_{1-6}$alkylene-OH, C$_{1-6}$ haloalkyl, cycloalkyl, heterocycloalkyl, C$_{0-3}$alkylene-C$_{3-14}$cycloalkyl, C$_{0-3}$alkylene-C$_{2-14}$ heterocycloalkyl, aryl, heteroaryl, C$_{0-3}$alkylene-C$_{6-14}$aryl, or selected from

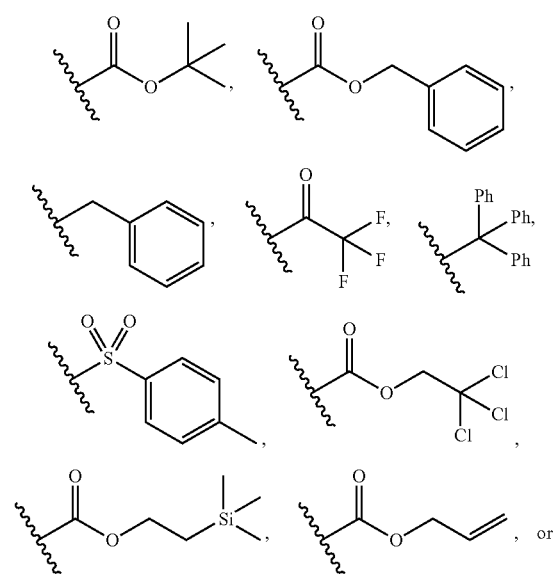

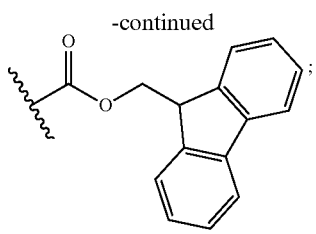

$R^5$ and $R^6$ are each independently H, halo, —$C_{1-6}$alkyl, —$C_{2-6}$alkynyl, —$C_{1-6}$ alkylene-O—$C_{1-4}$alkyl, —$C_{1-6}$ alkylene-OH, —$C_{1-6}$haloalkyl, —$C_{1-6}$alkyleneamine, —$C_{0-6}$ alkylene-amide, —$C_{0-3}$alkylene-C(O)OH, —$C_{0-3}$alkylene-C(O)O$C_{1-4}$alkyl, —$C_{1-6}$ alkylene-O-aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, —$C_{0-3}$alkylene-$C_{2-14}$heteroaryl, or cyano, or $R^5$ and $R^6$, together with the atoms to which they are attached, form a 4-6 membered ring;

$R^7$ is H or $C_{1-6}$alkyl, or $R^7$ and $R^5$, together with the atoms to which they are attached, form a 4-6 membered ring;

$R^8$ is —$C_{1-6}$alkyl, —$C_{0-3}$alkylene-$C_{6-14}$aryl, —$C_{0-3}$alkylene-$C_{3-14}$heteroaryl, —$C_{0-3}$ alkylene-$C_{3-14}$cycloalkyl, —$C_{0-3}$alkylene-$C_{2-14}$heterocycloalkyl, —$C_{1-6}$alkoxy, —O—$C_{0-3}$ alkylene-$C_{6-14}$aryl, —O—$C_{0-3}$alkylene-$C_{3-14}$heteroaryl, —O—$C_{0-3}$alkylene-$C_{3-14}$cycloalkyl, —O—$C_{0-3}$ alkylene-$C_{2-14}$heterocycloalkyl, —NH—$C_{1-8}$alkyl, —N($C_{1-8}$alkyl)$_2$, —NH—$C_{0-3}$alkylene-$C_{6-14}$aryl, —NH—$C_{0-3}$alkylene-$C_{2-14}$heteroaryl, —NH—$C_{0-3}$alkylene-$C_{3-14}$cycloalkyl, —NH—$C_{0-3}$ alkylene-$C_{2-14}$heterocycloalkyl, halo, cyano, or $C_{1-6}$alkylene-amine;

wherein the heteroaryl, spiroheterocycloalkyl and heterocycloalkyl groups of any of the $R^p$, $R^2$, $R^{2a}$, $R^3$, $R^4$, $R^{4a}$, $R^5$, $R^6$, $R^7$, and $R^8$ substituents have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or SO$_2$;

wherein the —$C_{1-6}$alkyl, —$C_{2-6}$alkenyl, —$C_{2-6}$alkynyl and the —O$C_{1-6}$alkyl of any of the $R^p$, $R^1$, $R^2$, $R^{2a}$, $R^3$, $R^4$, $R^{4a}$, L, $R^5$, $R^6$, $R^7$, and $R^8$ substituents is unsubstituted or substituted by 1, 2 or 3 $R^9$ substituents independently selected from OH, —O$C_{1-6}$alkyl, —$C_{1-6}$alkyl-O—$C_{1-6}$alkyl, halo, —O-halo$C_{1-6}$alkyl, —CN, —NR$^a$R$^b$, —(NR$^a$R$^b$R$^c$)$_n$, —OSO$_2$R$^a$, —SO$_2$R$^a$, —(CH$_2$CH$_2$O)$_n$CH$_3$, —(=O), —C(=O), —C(=O)R$^a$, —OC(=O)R$^a$, —C(=O)OR$^a$, —C(=O)NR$^a$R$^b$, —O—SiR$^a$R$^b$R$^c$, —SiR$^a$R$^b$R$^c$, —O-(3- to 10-membered heterocycloakyl), a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or SO$_2$;

wherein the aryl, heteroaryl, cycloalkyl, and heterocycloalkyl group of any of the $R^p$, $R^1$, $R^2$, $R^{2a}$, $R^3$, $R^4$, $R^{4a}$, $R^5$, $R^6$, $R^7$, $R^8$ and $R^9$ substituents can be unsubstituted or substituted with 1, 2, 3 or 4 $R^{10}$ substituents independently selected from OH, halo, —NR$^c$R$^d$, —$C_{1-6}$alkyl, —O$C_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —SO$_2$R$^c$, —CN, —C(=O)NR$^c$R$^d$, —C(=O)R$^c$, —OC(=O)R$^a$, —C(=O)OR$^c$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups of $R^{10}$ have 1, 2, 3 or 4 heteroatoms independently selected from O, N or S, wherein the cycloalkyl, spirocycloalkyl, and spiroheterocycloalkyl groups of $R^{10}$ or the heterocycloalkyl group of $R^{10}$ may include a C=O group, and further wherein the spiroheterocycloalkyl and heterocycloalkyl groups may include a S=O or SO$_2$;

wherein each R$^a$, R$^b$, R$^c$ and R$^d$ is independently hydrogen, OH, —$C_{1-6}$alkyl, —(CH$_2$CH$_2$O)$_n$CH$_3$, —NR$^{11}$R$^{11}$, —$C_{1-6}$alkyl-NR$^{11}$R$^{11}$, phenyl, —$C_{1-6}$alkyl-C(=O)OH, —$C_{1-6}$alkyl-C(=O)—O—$C_{1-6}$alkyl, —$C_{1-6}$alkyl-3- to 12-membered cycloalkyl, —$C_{1-6}$alkyl-3- to 12-membered heterocycloalkyl, —$C_{1-6}$alkyl-6- to 12-membered heteroaryl, a 6- to 12-membered aryl or heteroaryl, a 3- to 12-membered monocyclic or bicyclic cycloalkyl, or a 3- to 12-membered monocyclic or bicyclic heterocycloalkyl group, wherein the heteroaryl group, heterocycloalkyl group of R$^a$, R$^b$, R$^c$, and R$^d$ or the heterocycloalkyl group of the —$C_{1-6}$alkyl-heterocycloalkyl group of R$^a$, R$^b$, R$^c$, and R$^d$ has from 1, 2, 3, or 4 heteroatoms independently selected from O, N or S, wherein the cycloalkyl and heterocycloalkyl groups of R$^a$, R$^b$, R$^c$, and R$^d$ and the heterocycloalkyl group of the —$C_{1-6}$alkyl-heterocycloalkyl groups of R$^a$, R$^b$, R$^c$, and R$^d$ may include a double bond, and further wherein the cycloalkyl and heterocycloalkyl groups of R$^a$, R$^b$, R$^c$, and R$^d$ and the heterocycloalkyl group of the —$C_{1-6}$alkyl-heterocycloalkyl groups of R$^a$, R$^b$, R$^c$, and R$^d$ may contain a C=O group; and the alkyl, aryl, heteroaryl, cycloalkyl, heterocycloalkyl groups of R$^a$, R$^b$, R$^c$, and R$^d$ or the heterocycloalkyl groups of the —$C_{1-6}$alkyl-heterocycloalkyl groups of R$^a$, R$^b$, R$^c$, and R$^d$ can be unsubstituted or substituted with from 1, 2, 3, or 4 $R^{12}$ substituents, wherein each $R^{12}$ is independently selected from H, OH, halo, —$C_{1-6}$alkyl, N(CH$_3$)$_2$, —$C_{1-6}$haloalkyl, C(=O)CH$_3$, —C(=O)OCH$_3$, or —$C_{1-6}$alkyl-O—$C_{1-6}$alkyl; or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

2. The compound of claim 1 wherein $R^p$ is —$C_{1-6}$alkyl.

3. The compound of claim 2 wherein $R^p$ is —CH$_3$.

4. The compound of claim 1 wherein $R^1$ is H.

5. The compound of claim 1 wherein $R^2$ is an unsubstituted or substituted aryl.

6. The compound of claim 5 wherein $R^2$ is a substituted aryl.

7. The compound of claim 6 wherein $R^2$ is a fluorinated phenyl.

8. The compound of claim 1 wherein $R^3$ is halo.

9. The compound of claim 8 wherein $R^3$ is Cl.

10. The compound of claim 1 wherein $R^4$ is

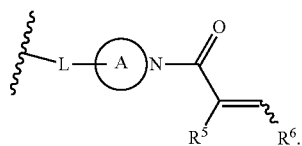

11. The compound of claim 10 wherein L is a bond.

12. The compound of claim 10 wherein ring A is a monocyclic 4-7 membered ring.

13. The compound of claim 12 wherein A is an unsubstituted or substituted heterocycle.

14. The compound of claim 1, wherein $R^4$ is selected from the group consisting of

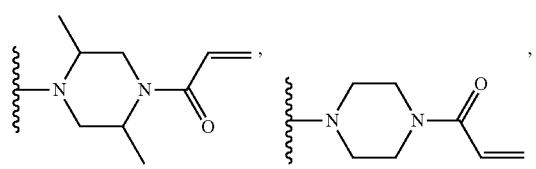

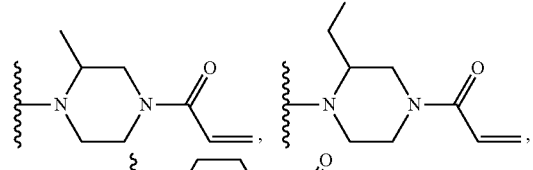

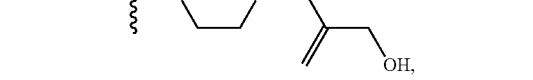

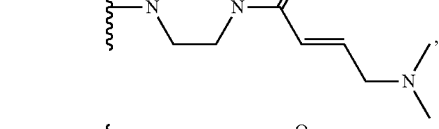

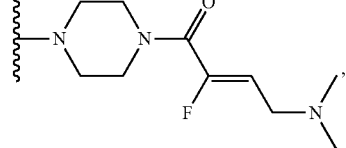

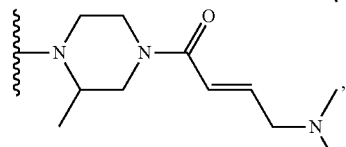

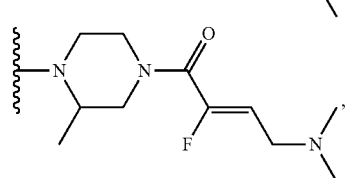

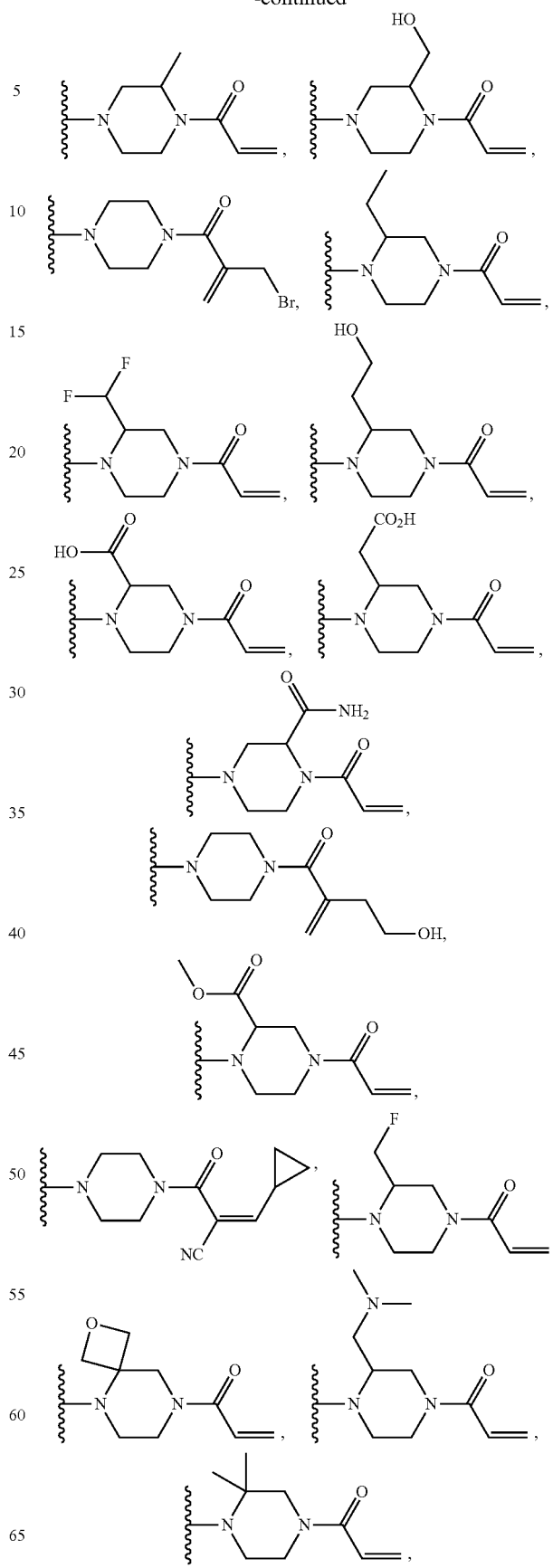

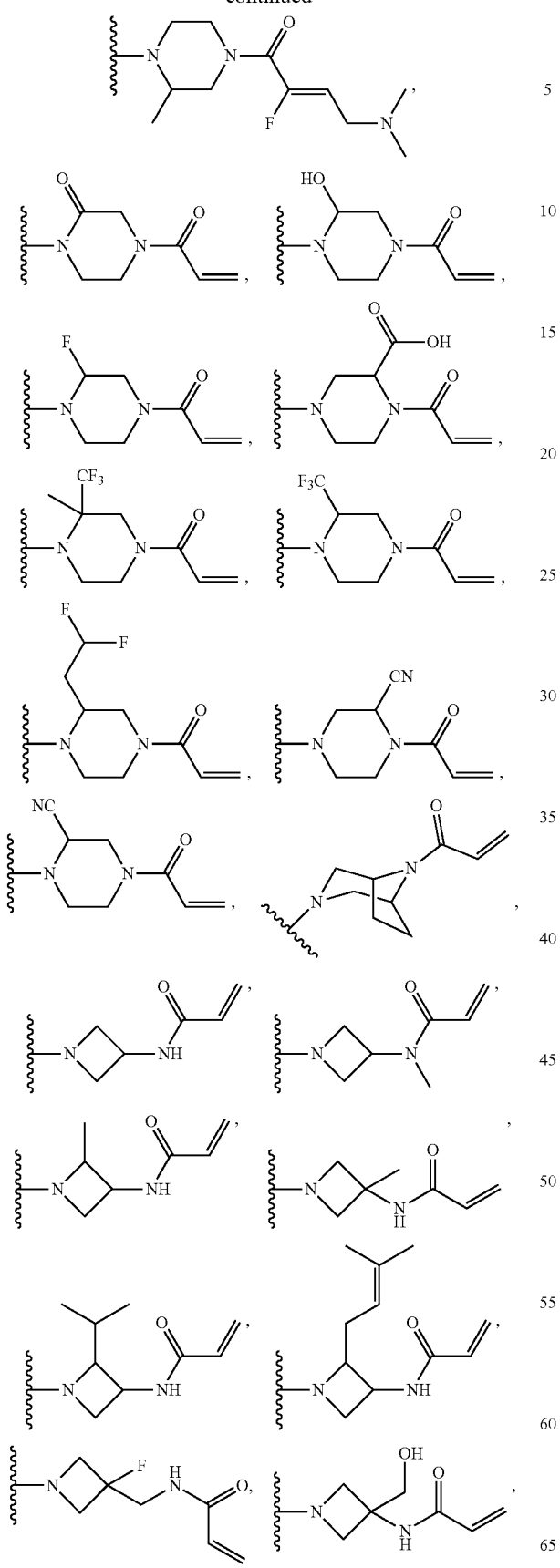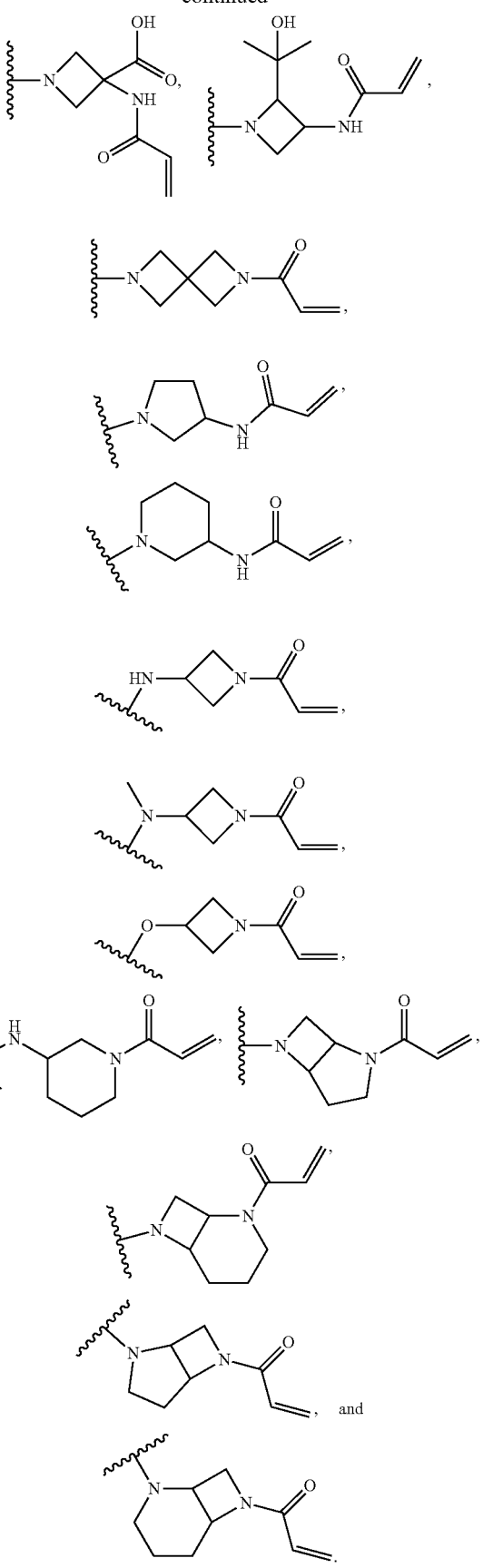

15. The compound of claim 14, wherein R⁴ is

[structure: 2,5-dimethylpiperazine with acryloyl group]

16. The compound of claim 9 wherein R⁵ is H.

17. The compound of claim 9 wherein R⁶ is H.

18. The compound of claim 1 wherein R⁸ is —C$_{1-6}$alkyl, —C$_{0-3}$alkylene-C$_{6-14}$aryl, or —C$_{0-3}$alkylene-C$_{3-14}$heteroaryl.

19. The compound of claim 18 wherein R⁸ is —C$_{1-6}$alkyl.

20. The compound of claim 18 wherein R⁸ is —C$_{6-14}$aryl.

21. The compound of claim 18 wherein R⁸ is —C$_{3-14}$heteroaryl.

22. The compound of claim 1, wherein R⁸ is selected from the group consisting of i-Pr, t-Bu, phenyl, benzyl, OCH₃, Cl, cyclopropyl, cyclobutyl, cyclopentyl, cyclohexyl,

[numerous chemical structures shown]

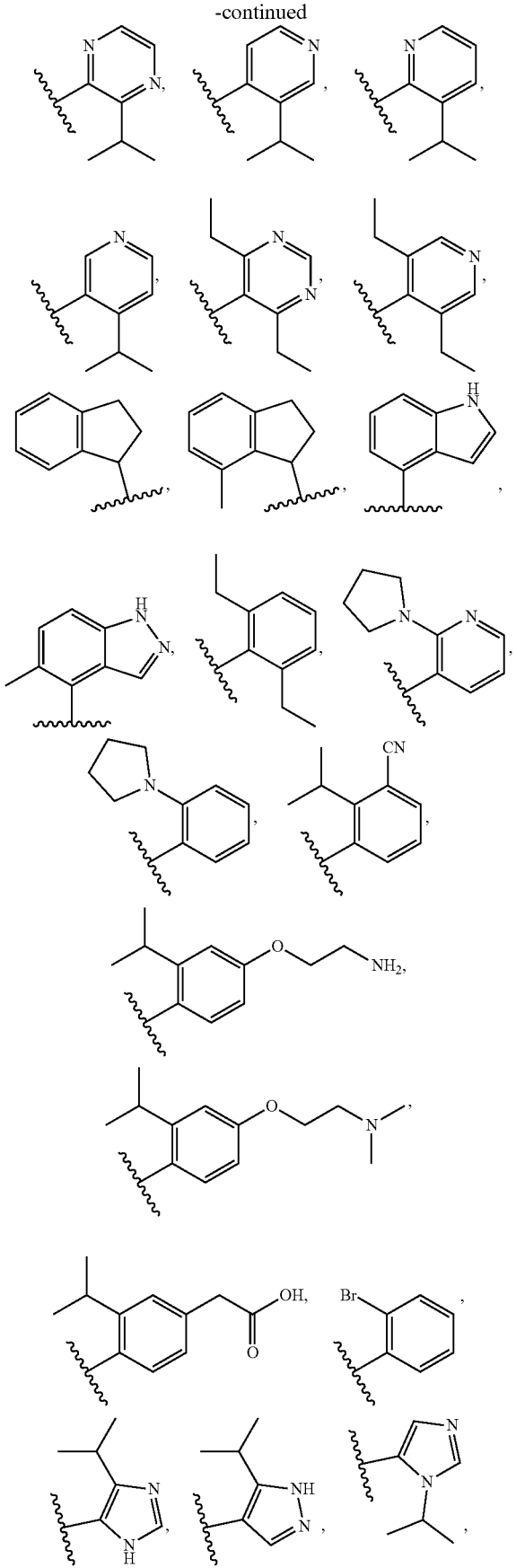
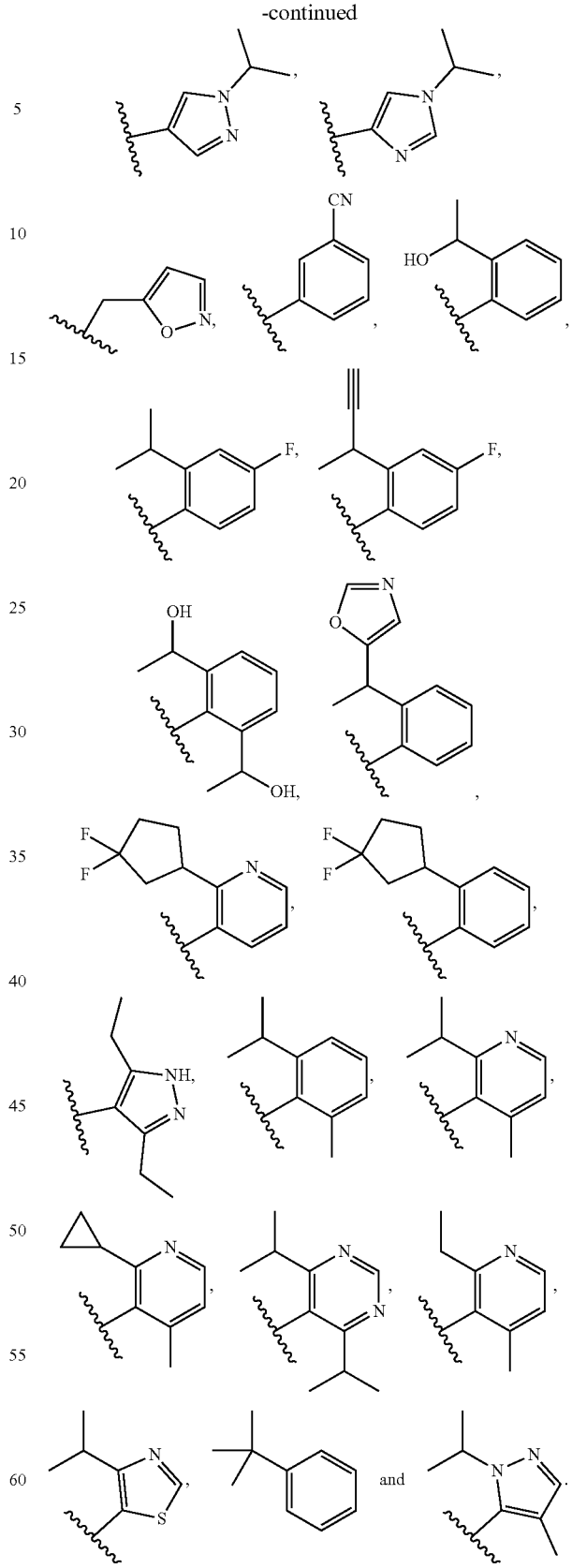
23. The compound of claim 22, wherein $R^8$ is selected from the group consisting of

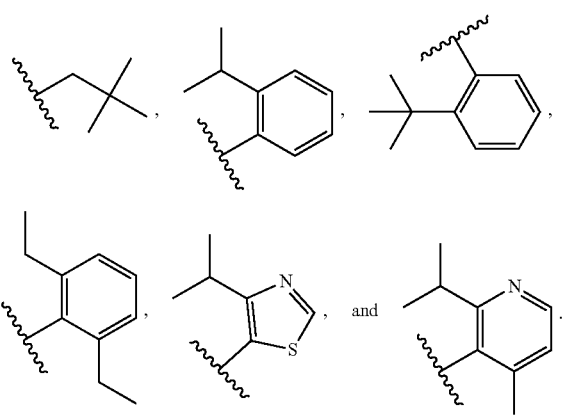
24. The compound of claim 22, wherein $R^8$ is
25. The compound of claim 22, wherein $R^8$ is
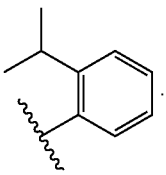 [SMILES: *c1ccccc1C(C)C]
26. The compound of claim 22, wherein $R^8$ is
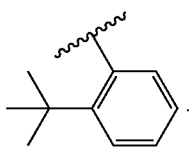
27. The compound of claim 22, wherein $R^8$ is
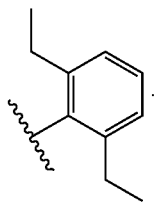
28. The compound of claim 22, wherein $R^8$ is
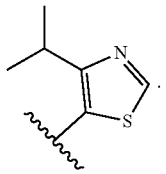 [SMILES: *c1scnc1C(C)C]
29. The compound of claim 22, wherein $R^8$ is
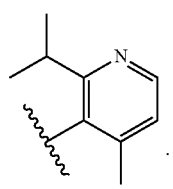
30. A compound having a structure selected from the formula
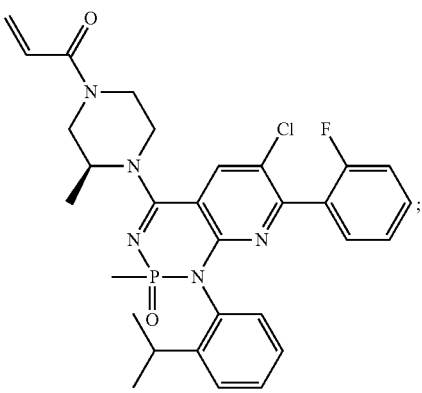
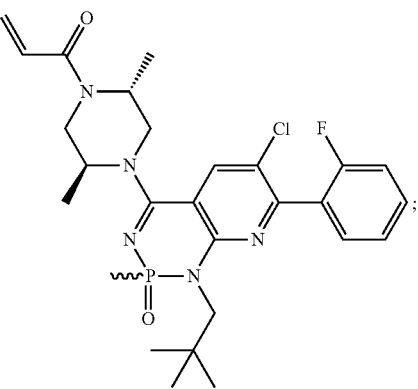
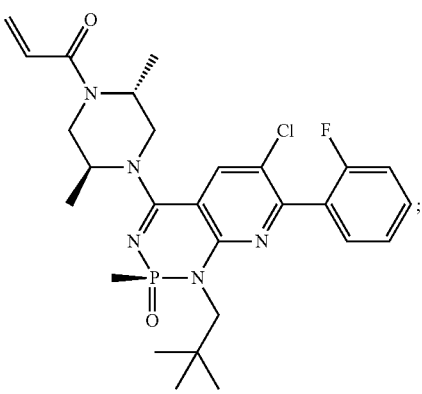

107
-continued
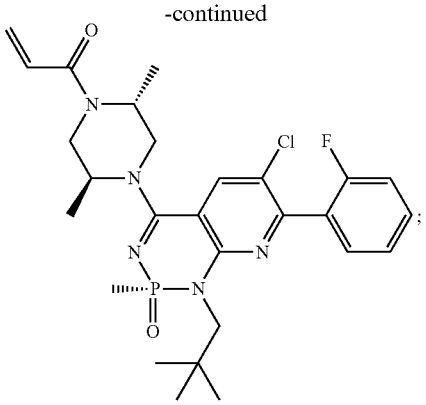
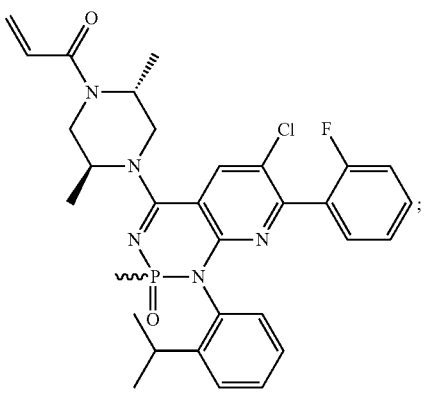
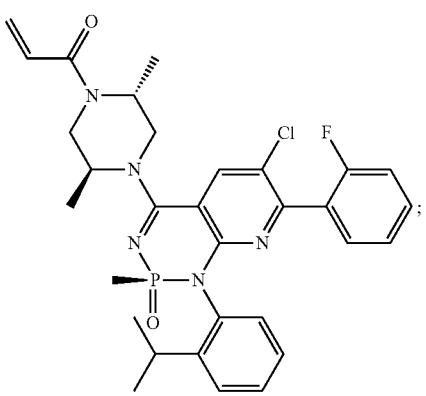
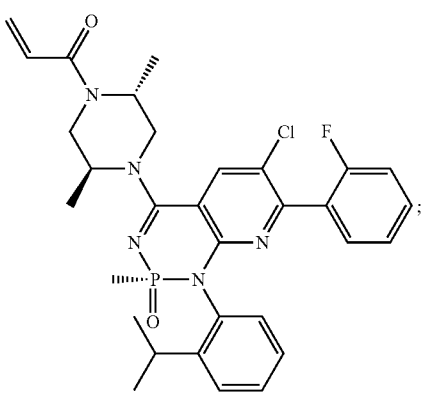
108
-continued
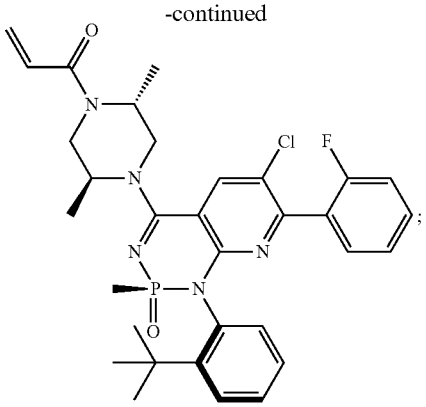
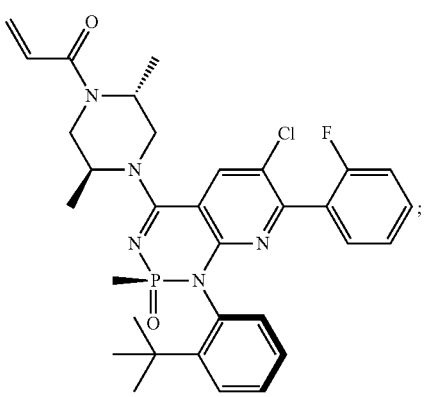
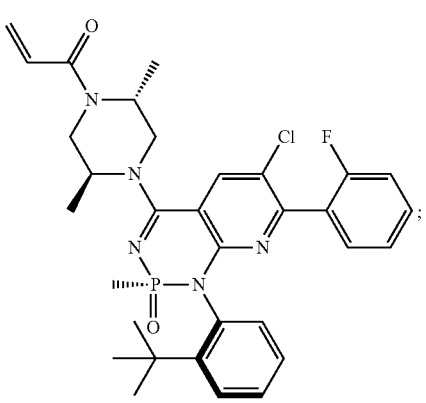
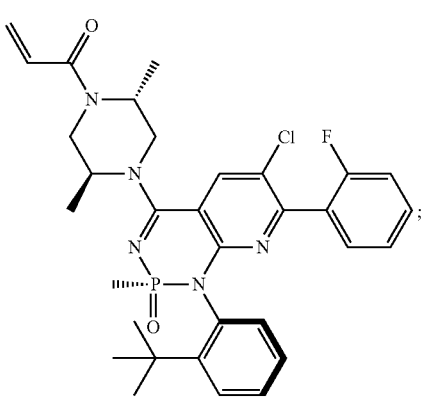

109
-continued
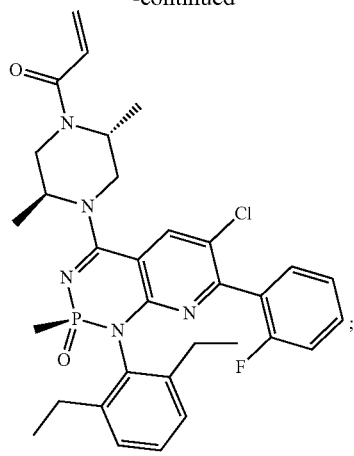
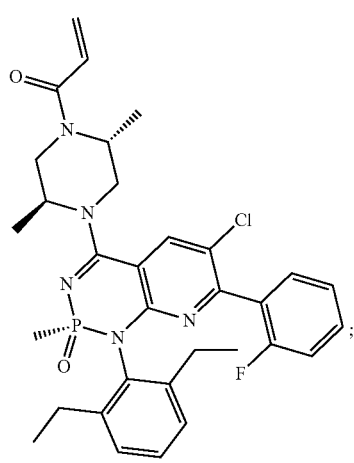
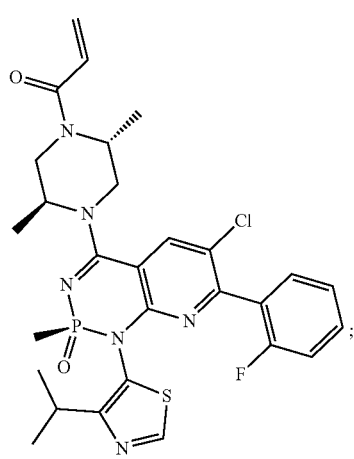
110
-continued
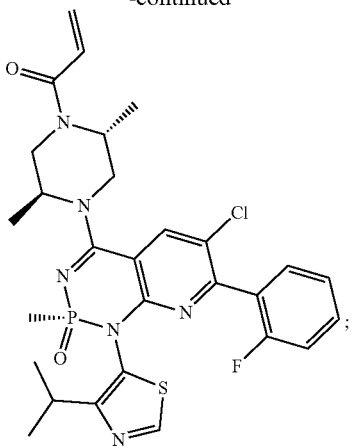
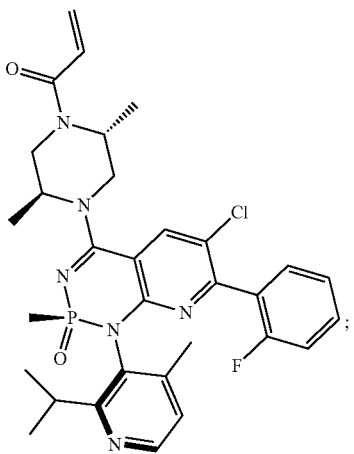
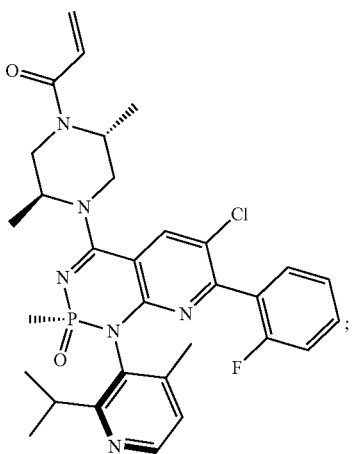

111
-continued

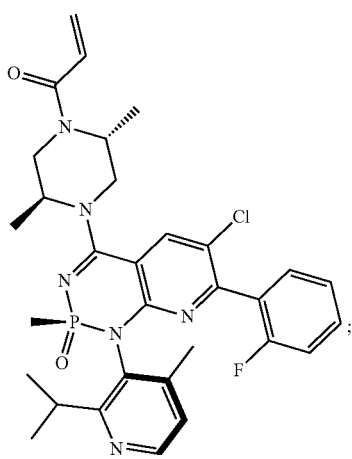

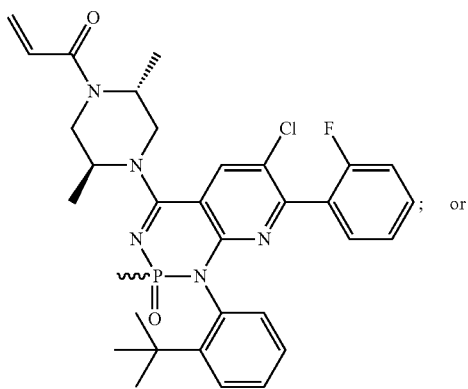

112
-continued

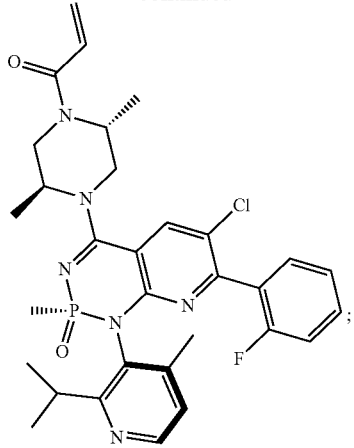

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

31. The compound of claim 1 in the form of a pharmaceutically acceptable salt.

32. A pharmaceutical formulation comprising the compound of claim 1 and a pharmaceutically acceptable excipient.

33. A method of inhibiting KRAS G12C in a cell, comprising contacting the cell with the compound of claim 1.

34. A method of treating non-small cell lung cancer in a subject comprising administering to the subject a therapeutically effective amount of the compound of claim 1.

\* \* \* \* \*